US012685740B2

(12) United States Patent
Lämmermann et al.

(10) Patent No.: US 12,685,740 B2
(45) Date of Patent: Jul. 21, 2026

(54) COMPOSITIONS FOR THE ELIMINATION OF SENESCENT CELLS

(71) Applicants: Universität für Bodenkultur Wien, Vienna (AT); Medizinische Universität Wien, Vienna (AT)

(72) Inventors: Ingo Lämmermann, Vienna (AT); Johannes Grillari, Vienna (AT); Vera Pils, Vienna (AT); Florian Gruber, Vienna (AT); Marie-Sophie Narzt, Vienna (AT)

(73) Assignees: UNIVERSITÄT FÜR BODENKULTUR WIEN, Vienna (AT); MEDIZINISCHE UNIVERSITÄT WIEN, Vienna (AT)

( * ) Notice: Subject to any disclaimer, the term of this patent is extended or adjusted under 35 U.S.C. 154(b) by 905 days.

(21) Appl. No.: 17/288,508

(22) PCT Filed: Oct. 25, 2019

(86) PCT No.: PCT/EP2019/079133
§ 371 (c)(1),
(2) Date: Apr. 23, 2021

(87) PCT Pub. No.: WO2020/084105
PCT Pub. Date: Apr. 30, 2020

(65) Prior Publication Data
US 2021/0379087 A1      Dec. 9, 2021

(30) Foreign Application Priority Data
Oct. 25, 2018     (EP) .................................... 18202657

(51) Int. Cl.
| | |
|---|---|
| *A61K 31/661* | (2006.01) |
| *A61K 31/196* | (2006.01) |
| *A61K 31/403* | (2006.01) |
| *A61K 31/405* | (2006.01) |
| *A61K 31/415* | (2006.01) |
| *A61K 31/616* | (2006.01) |
| *A61K 45/06* | (2006.01) |
| *A61P 35/00* | (2006.01) |
| *G01N 33/53* | (2006.01) |
| *G01N 33/569* | (2006.01) |

(52) U.S. Cl.
CPC ............ *A61K 31/661* (2013.01); *A61K 45/06* (2013.01); *G01N 33/5308* (2013.01); *G01N 33/56966* (2013.01); *G01N 2500/10* (2013.01); *G01N 2510/00* (2013.01); *G01N 2800/7042* (2013.01)

(58) Field of Classification Search
CPC .. A61K 31/661; A61K 45/06; G01N 33/5308; G01N 2510/00; G01N 2800/7042
See application file for complete search history.

(56) References Cited

U.S. PATENT DOCUMENTS

2012/0178782 A1     7/2012   Podesta

FOREIGN PATENT DOCUMENTS

| | | |
|---|---|---|
| CN | 106687602 A | 5/2017 |
| CN | 110564852 A | 12/2019 |
| WO | 2007023306 A1 | 3/2007 |
| WO | 2011144761 A1 | 11/2011 |
| WO | 2013155085 A1 | 10/2013 |
| WO | 2015116735 A1 | 8/2015 |
| WO | 2019070407 A1 | 4/2019 |

OTHER PUBLICATIONS

Lorenzini A, Hrelia S, Bordoni A, Biagi P, Frisoni L, Marinucci T, Cristofalo VJ. Is increased arachidonic acid release a cause or a consequence of replicative senescence? Exp Gerontol. Jan. 2001;36(1):65-78. doi: 10.1016/s0531-5565(00)00192-3. PMID: 11162912. (Year: 2001).*
Tallima H, El Ridi R. Arachidonic acid: Physiological roles and potential health benefits—A review. J Adv Res. Nov. 24, 2017;11:33-41. doi: 10.1016/j.jare.2017.11.004. PMID: 30034874; PMCID: PMC6052655. (Year: 2017).*
Hanna VS, Hafez EAA. Synopsis of arachidonic acid metabolism: A review. J Adv Res. Mar. 13, 2018;11:23-32. doi: 10.1016/j.jare.2018.03.005. PMID: 30034873; PMCID: PMC6052663. (Year: 2018).*
Sharpless NE, Sherr CJ. Forging a signature of in vivo senescence. Nat Rev Cancer. Jul. 2015;15(7):397-408. doi: 10.1038/nrc3960. Erratum in: Nat Rev Cancer. Aug. 2015;15(8):509. PMID: 26105537. (Year: 2015).*
Kirkland JL, Tchkonia T. Senolytic drugs: from discovery to translation. J Intern Med. Nov. 2020;288(5):518-536. doi: 10.1111/joim.13141. Epub Aug. 4, 2020. PMID: 32686219; PMCID: PMC7405395. (Year: 2020).*
He S, Sharpless NE. Senescence in Health and Disease. Cell. Jun. 1, 2017;169(6):1000-1011. doi: 10.1016/j.cell.2017.05.015. PMID: 28575665; PMCID: PMC5643029. (Year: 2017).*
Jeon OH et al. Local clearance of senescent cells attenuates the development of post-traumatic osteoarthritis and creates a pro-regenerative environment. Nat Med. 2017, 23, 6, 775-781 (Year: 2017).*

(Continued)

*Primary Examiner* — Bruck Kifle
*Assistant Examiner* — Kevin S Martin
(74) *Attorney, Agent, or Firm* — LOZA & LOZA, LLP; Michael F. Fedrick

(57) ABSTRACT

The invention relates to a composition comprising one or more inhibitors capable of inhibiting at least two of cyclooxygenase-1 (COX-1), cyclooxygenase-2 (COX-2) and lipoxygenase or a composition comprising one or more inhibitors capable of inhibiting an enzyme with arachidonate-Co A ligase activity, specifically long-chain-fatty-acid-Co A ligase (ACSL) 1, ACSL3, ACSL4, ACSL5, ACSL6, SLC27A2 or ACSBG2, or a combination thereof for use in selectively eliminating senescent cells. The invention further relates to an in vitro method of identifying senescent cells in a subject and to a method of identifying candidate compounds for the selective elimination of senescent cells.

11 Claims, 16 Drawing Sheets

(56)　　　　　　　References Cited

OTHER PUBLICATIONS

Figure 1:
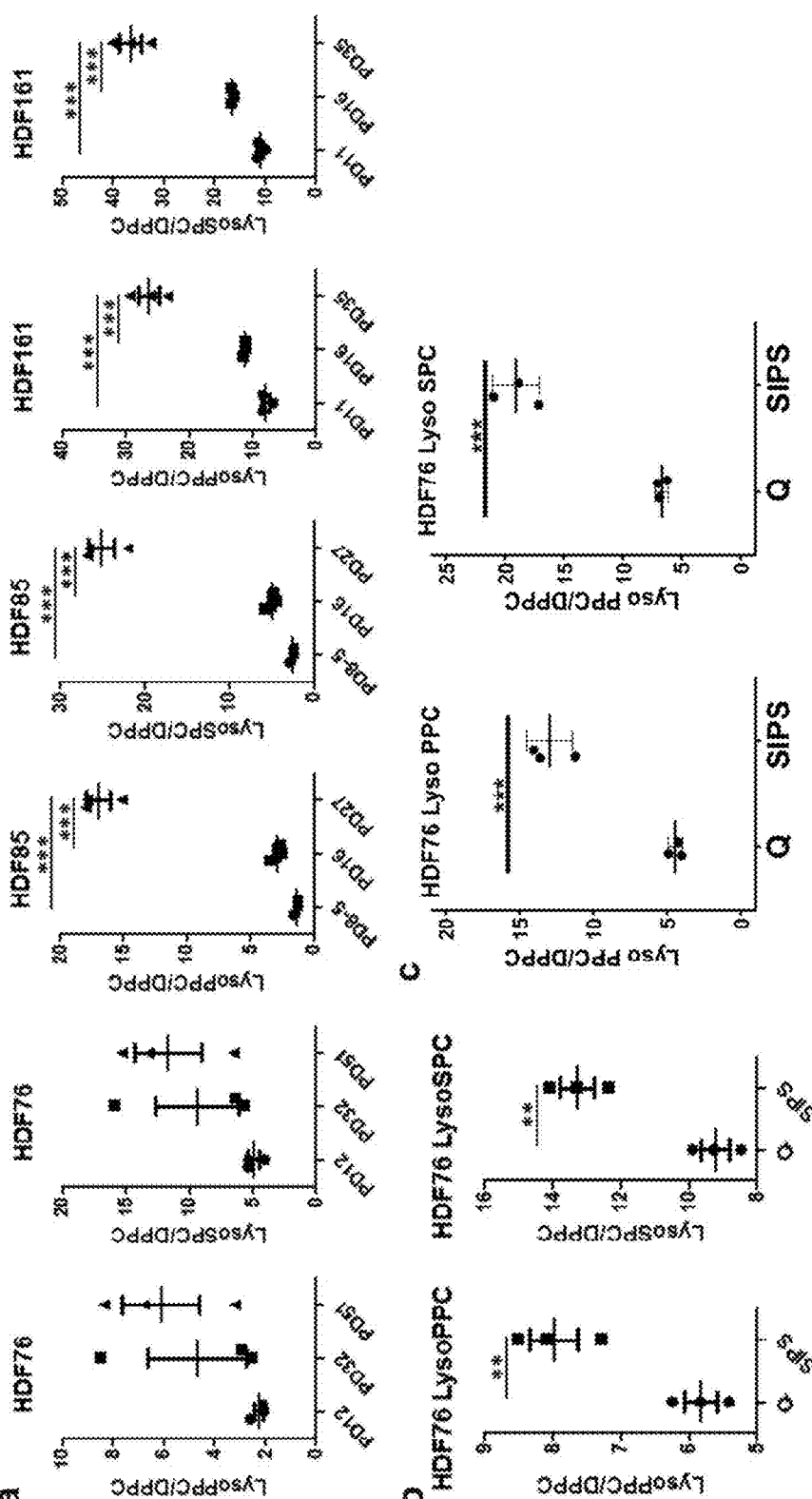

Childs BG, Gluscevic M, Baker DJ, Laberge RM, Marquess D, Dananberg J, van Deursen JM. Senescent cells: an emerging target for diseases of ageing. Nat Rev Drug Discov. Oct. 2017;16(10):718-735. (Year: 2017).*

Childs BG, Baker DJ, Wijshake T, Conover CA, Campisi J, van Deursen JM. Senescent intimal foam cells are deleterious at all stages of atherosclerosis. Science. Oct. 28, 2016;354(6311):472-477. (Year: 2016).*

Castillo et al., New inhibitor targeting Acyl-CoA synthetase 4 reduces breast and prostate tumor growth, therapeutic resistance and steroidogenesis. Cell Mol Life Sci. Mar. 2021;78(6):2893-2910 (Year: 2021).*

Levey AS, Coresh J. Chronic kidney disease. Lancet. Jan. 14, 2012;379(9811):165-80. doi: 10.1016/S0140-6736(11)60178-5. Epub Aug. 15, 2011. PMID: 21840587. (Year: 2011).*

Matsuda D, Namatame I, Ohshiro T, Ishibashi S, Omura S, Tomoda H. Anti-atherosclerotic activity of triacsin C, an acyl-CoA synthetase inhibitor. J Antibiot (Tokyo). May 2008;61(5):318-21. doi: 10.1038/ja.2008.45. PMID: 18653998. (Year: 2008).*

Jawien J, Gajda M, Rudling M, Mateuszuk L, Olszanecki R, Guzik TJ, Cichocki T, Chlopicki S, Korbut R. Inhibition of five lipoxygenase activating protein (FLAP) by MK-886 decreases atherosclerosis in apoE/LDLR-double knockout mice. Eur J Clin Invest. Mar. 2006;36(3):141-6. (Year: 2006).*

Vidal C. et al. Licofelone, a balanced inhibitor of cyclooxygenase and 5-lipoxygenase, reduces inflammation in a rabbit model of atherosclerosis. J Pharmacol Exp Ther. Jan. 2007;320(1):108-16. doi: 10.1124/jpet.106.110361. Epub Oct. 2, 2006. PMID: 17015640. (Year: 2007).*

Sandoval, A et al. "Identification and characterization of small compound inhibitors of human FATP2", Biochem. Pharmacol., 2010, 79(7): 990, 28 pgs.

Schafer, M J et al. "Cellular senescence mediates fibrotic pulmonary disease" Nature Communications, 2017, 8:14532, 11 pgs.

Schmitt, R et al. "Molecular mechanisms of renal aging", Kidney Int., 2017, vol. 92, No. 3, pp. 569-579.

Scott, G A et al. "sPLA2-X Stimulates Cutaneous Melanocyte Dendricity and Pigmentation Through a Lysophosphatidylcholine-Dependent Mechanism, Mechanism", J. Invest. Dermatol., 2006, vol. 126, No. 4, pp. 855-861.

Six, D A et al. "The expanding superfamily of phospholipase A2 enzymes: classification and characterization", Biochim. Biophys. Acta., 2000, vol. 1488, No. 1-2, pp. 1-19 pgs.

Terlecki-Zaniewics, L et al. "Small extracellular vesicles and their miRNA cargo are anti-apoptotic members of the senescence-associated secretory phenotype", Aging (Albany. NY), 2018, vol. 10, No. 5, pp. 1103-1132.

Trapnell, C et al. "Differential gene and transcript expression analysis of RNA-seq experiments with TopHat and Cufflinks", Nat. Protoc., 2012, vol. 7, No. 3, pp. 562-578.

Valentijn, F A et al. "Cellular senescence in the aging and diseased kidney", J. Cell Commun. Signal., 2018, vol. 12, No. 1, pp. 69-82.

Wang, Y et al. "MiR-133a in Human Circulating Monocytes: A Potential Biomarker Associated with Postmenopausal Osteoporosis", PlosOne, 2012, vol. 7, No. 4, e34641, 7 pgs.

Wang, Y et al. "Discovery of piperlongumine as a potential novel lead for the development of senolytic agents", Aging (Albany. NY), 2016, vol. 8, No. 11, pp. 2915-2926.

Wang, X-F et al. "Photo-protective activity of pogostone against UV-induced skin premature aging in mice", Accepted Manuscript, Gerontol., 2016, vol. 77, doi: 10.1016/j.exger.2016.02.017, 43 pgs.

Wang H et al. "Cyclooxygenase active bioflavonoids from Balaton™ tart cherry and their structure activity relationships", Phytomedicine, 2000, vol. 7, No. 1, pp. 15-19.

Weilner, S et al. "Differentially circulating miRNAs after recent osteoporotic fractures can influence osteogenic differentiation", Bone, 2015, vol. 79, pp. 43-51.

Xu, M et al. "Targeting senescent cells enhances adipogenesis and metabolic function in old age", Elife, 2015, vol. 4, e12997, 19 pgs.

Yiu, G K et al. "NFAT Induces Breast Cancer Cell Invasion by Promoting the Induction of Cyclooxygenase-2", J. Biol. Chem., May 5, 2006, vol. 281, No. 18, pp. 12210-12217.

Yosef, R et al. "Directed elimination of senescent cells by inhibition of BCL-W and BCL-XL", Nature Communications, 2016, 7:11190, 11 pgs.

Zdanov, S et al. "Normal or stress-induced fibroblast senescence involves COX-2 activity", Experimental Cell Res., 2007, vol. 313, No. 14, pp. 3046-3056.

Zhang, X et al. "Oxidation resistance 1 is a novel senolytic target", Aging Cell., 2018, vol. 17, No. 4, e12780, 14 pgs.

Zhu, Y et al. "The Achilles' heel of senescent cells: from transcriptome to senolytic drugs", Aging Cell., 2015, vol. 14, No. 4, pp. 644-658.

Zhu, Y et al. "Identification of a novel senolytic agent, navitoclax, targeting the Bcl-2 family of anti-apoptotic factors", Aging Cell., 2016, vol. 15, No. 3, pp. 428-435.

Zhu, Y et al. "New agents that target senescent cells: the flavone, fisetin, and the BCL-XL inhibitors, A1331852 and A1155463", Aging (Albany. NY), 2017, vol. 9, No. 3, pp. 955-963.

Alvaro-Gracia J M, Rheumatology, 2004, vol. 43, Suppl 1, pp. 21-25.

Gugliucci A et al., J of Biol Chem, 2002, vol. 227, No. 35, pp. 31789-31795.

Hundley T R et al., J of Pharmacol and Exp Therapeutics., 1998, vol. 284, No. 3, pp. 847-857.

Singapore Search Report, corresponding Singapore Patent Application No. 111202103736U, Dec. 9, 2022, 4 pgs.

Singapore Written Opinion, corresponding Singapore Patent Application No. 111202103736U, Dec. 12, 2022, 8 pgs.

Hongyu, Dong et al. "Montelukast inhibits inflammatory response in rheumatoid arthritis fibroblast-like synoviocytes", Int. Immunopharmacology, 2018, vol. 61, pp. 215-221.

Choi, Dong Kug et al. "Recent developments in the inhibitors of neuroinflammation and neurodegeneration: inflammatory oxidative enzymes as a drug target", Expert Opin. Ther. Patents, 2010, vol. 20, No. 11, pp. 1531-1546.

Hölzl, Katja et al. "Gelatin methacryloyl as environment for chondrocytes and cell delivery to superficial cartilage defects", Journal of Tissue Engineering and Regenerative Medicine, 2022, vol. 16, No. 2, pp. 207.

Khan, Mohammed Naseer A. et al. "Cyclooxygenase Inhibitors: Scope of Their Use and Development in Cancer Chemotherapy", Medicinal Research Reviews, 2011, vol. 31, No. 2, pp. 161-201.

Nash, P, "Psoriatic arthritis therapy: NSAIDs and traditional DMARDs", Annals of the Rheumatic Diseases, 2005, vol. 64, Suppl. II, pp: ii74-ii77.

Salomon, Salvatore, "Pleiotropic effects of glitazones: a double edge sword?", Frontiers in Pharmacol., 2011, vol. 2, Article 14, 6 pgs.

Sturm, Lisa et al. "In Vitro Evaluation of a Nanoparticle-Based mRNA Delivery System for Cells in the Joint", Biomedicines, 2021, vol. 9, No. 794, 17 pgs.

Das, Undurti N, "Ageing: Is there a role for arachidonic acid and other bioactive lipids? A review", J Adv Res., 2018, vol. 15, No. 11, pp. 67-79.

Wahlmueller, Marlene et al. "Establishment of In Vitro Models by Stress-Induced Premature Senescence for Characterizing the Stromal Vascular Niche in Human Adipose Tissue", Life, 2022, vol. 12, No. 1459, 20 pgs.

Wong, Siu Ling et al. "Prostaglandins in Action: Indispensable Roles of Cyclooxygenase-I and -2 Endothelium-Dependent Contractions", Adv. In Pharmacol., 2010, vol. 60, pp. 61-83.

Acosta, J C et al. "A complex secretory program orchestrated by the inflammasome controls paracrine senescence", Nat. Cell Biol., 2013, vol. 15, No. 8, pp. 978-990.

Briot, Anais et al. "Senescence Alters PPARγ (Peroxisome Proliferator-Activated Receptor Gamma)-Dependent Fatty Acid Handling in Human Adipose Tissue Microvascular Endothelial Cells and Favors InflammationArteriosclerosis Thromb and Vascular", Biol., 2018, vol. 38, No. 5, pp. 1134-1146.

(56)

References Cited

OTHER PUBLICATIONS

Askari, B. et al. "Rosiglitazone Inhibits Acyl-CoA Synthetase Activity and Fatty Acid Partitioning to Diacylglycerol and Triacylglycerol via a Peroxisome Proliferator-Activated Receptor-γ-Independent Mechanism in Human Arterial Smooth Muscle Cells and Macrophages", Diabetes. NIH Public Access, Apr. 2007, vol. 56, No. 4, pp. 1143-1152.

Augert, A. et al. "The M-type receptor PLA2R regulates senescence through the p53 pathway", EMBO Rep. European Molecular Biology Organization, 2009, vol. 10, No. 3, pp. 271-277.

Baar, M P et al. "Targeted Apoptosis of Senescent Cells Restores Tissue Homeostasis in Response to Chemotoxicity and Aging", Cell, 2017, vol. 169, No. 1, pp. 132-147.

Baker, D J et al. "Clearance of p16Ink4a-positive senescent cells delays ageing associated disorders", Nature, 2012, vol. 479, No. 7372, pp. 232-236.

Baker, D J et al. "Naturally occurring p16Ink4a-positive cells shorten healthy lifespan", Nature, 2016, vol. 530, No. 7589, pp. 184-189.

Braun, H. et al. "Cellular Senescence Limits Regenerative Capacity and Allograft Survival", J. Am. Soc. Nephrol., 2012, vol. 23, No. 9, pp. 1467-1473.

Brideau, C. et al. "A human whole blood assay for clinical evaluation of biochemical efficacy of cyclooxygenase Inhibitors", Inflamm. Res., 1996, vol. 45, No. 2, pp. 68-74.

Bussian, T J et al. "Clearance of senescent glial cells prevents tau-dependent pathology and cognitive decline", Nature, 2018, vol. 562, No. 7728, pp. 578-582.

Campisi, J. et al. "Cellular senescence: when bad things happen to good cells", Nat. Rev. Mol. Cell Biol., 2007, vol. 8, No. 9, pp. 729-740.

Chang, J. et al. "Clearance of senescent cells by ABT263 rejuvenates aged hematopoietic stem cells in mice", Nat. Med. Nature Publishing Group, 2016, vol. 22, No. 1, pp. 78-83.

Childs, B G et al. "Senescent intimal foam cells are deleterious at all stages of atherosclerosis", Science, 2016, vol. 354, No. 6311, pp. 472-477.

Choi, J et al. "Lysophosphatidylcholine is Generated by Spontaneous Deacylation of Oxidized Phospholipids", Chem. Res. Toxicol., 2011, vol. 24, No. 1, pp. 111-118.

Coppé, J-P et al. "The Senescence-Associated Secretory Phenotype: The Dark Side of Tumor Suppression", Annu Rev Pathol., 2010, vol. 5, pp. 99-118.

Currais, A et al. "Amyloid proteotoxicity initiates an inflammatory response blocked by cannabinoids", npj Aging Mech. Dis., 2016, vol. 2, No. 1, 16012, 8 pgs.

Demaria, M et al. "An Essential Role for Senescent Cells in Optimal Wound Healing through Secretion of PDGF-AA", Dev. Cell., 2014, 31(6): 722-733.

Dörr, J R et al. "Synthetic lethal metabolic targeting of cellular senescence in cancer therapy", Nature, 2013, vol. 501, No. 7467, doi: 10.1038/nature12437, 8 pgs.

Farr, J N et al. "Targeting cellular senescence prevents age-related bone loss in mice", Nat. Med., 2017, 23(9): 1072-1079.

Fonteh, A N et al. "Secretory Phospholipase A2 Receptor-Mediated Activation of Cytosolic Phospholipase A2 in Murine Bone Marrow-Derived Mast Cells", J. Immunol., 2000, vol. 165, No. 5, pp. 2773-2782.

Furhrmann-Stroissnigg, H et al. "Identification of HSP90 inhibitors as a novel class of senolytics", Nat. Commun., 2017, vol. 8, No. 422, DOI: 10.1038/s41467-017-00314-z, 14 pgs.

Gruber, F et al. "Nrf2 deficiency causes lipid oxidation, inflammation and matrix-protease expression in DHA supplemented and UVA irradiated skin fibroblasts", Free Radic. Biol. Med., 2015, vol. 88 (Pt B), DOI: http://dx.doi.org/10.1016/j.freeradbiomed.2015.05.006, 28 pgs.

Hernández, G L et al. "Selective Inhibition of Vascular Endothelial Growth Factor-mediated Angiogenesis by Cyclosporin A: Roles of the Nuclear Factor of Activated T Cells and Cyclooxygenase 2", J. Exp. Med., 2001, vol. 193, No. 5, pp. 607-620.

Hiubackova, S et al. "Selective elimination of senescent cells by mitochondrial targeting is regulated by ANT2", Cell Death Differ, 2019, vol. 26, No. 2, pp. 276-290.

Hutchinson, J H et al."5-Lipoxygenase-Activating Protein Inhibitors: Development of 3-[3-tert-Butylsulfanyl-1-[4-(6-methoxy-pyridin-3-yl)-benzyl]-5-(pyridin-2-ylmethoxy)-1H-indol-2-yl]-2,2-dimethyl-propionic Acid (AM103)", J. Med. Chem., 2009, vol. 52, No. 19, pp. 5803-5815.

Hwang, H W et al. "Investigation of quercetin and hyperoside as senolytics in adult human endothelial cells", PLoS One, 2018, vol. 13, No. 1, DOI: https://doi.org/10.1371/journal.pone.0190374, 14 pgs.

Jeon, O H et al. "Local clearance of senescent cells attenuates the development of post-traumatic osteoarthritis and creates a pro-regenerative environment", Nat. Med., 2017, 23(6): 775-781.

Jeschek, D et al. "A versatile, quantitative analytical method for pharmaceuticalrelevant lipids in drug delivery systems", J. Pharm. Biomed. Anal., 2016, vol. 119, pp. 37-44.

Kabir, T et al. "A miR-335/COX-2/PTEN axis regulates the secretory phenotype of senescent cancer-associated fibroblasts", Aging (Albany. NY), 2016, vol. 8, No. 8, pp. 1608-1635.

Kim, J-H et al. "Expression and Characterization of Recombinant Rat Acyl-CoA Synthetases 1, 4, and 5", J. Biol. Chem., 2001, vol. 276, No. 27, pp. 24667-24673.

Kim, Y et al. "Novel Triacsin C Analogs as Potential Antivirals against Rotavirus Infections", Eur. J. Med. Chem., 2012, vol. 50, pp. 311-318.

Krtolica, A et al. "Senescent fibroblasts promote epithelial cell growth and tumorigenesis: A link between cancer and aging", PNAS, 2001, vol. 98, No. 21, pp. 12072-12077.

Lämmermann, I et al. "Blocking negative effects of senescence in human skin fibroblasts with a plant extract", npj Aging Mech. Dis., 2018, vol. 4, No. 1, doi:10.1038/s41514-018-0023-5, 10 pgs.

Lehmann, M et al. "Senolytic drugs target alveolar epithelial cell function and attenuate experimental lung fibrosis ex vivo", Eur. Respir. J., 2017, vol. 50, No. 2, 1602367, 15 pgs.

Lewis, D A et al. "Reversing the aging stromal phenotype prevents carcinoma initiation", Aging (Albany. NY), 2011, vol. 3, No. 4, pp. 407-416.

Li, Y et al. "Age-associated increase of skin fibroblast-derived prostaglandin E2 contributes to reduced collagen levels in elderly human skin", J. Invest. Dermatol., 2015, 135(9): 2181-2188.

Lorenzini, A et al. "Is increased arachidonic acid release a cause or a consequence of replicative senescence?", Experimental Gernotology, 2001, vol. 36, No. 1, pp. 65-78.

Lötzer, K et al. "5-Lipoxygenase/cyclooxygenase-2 cross-talk through cysteinyl leukotriene receptor 2 in endothelial cell", Prostaglandins Other Lipid Mediat., 2007, vol. 84, No. 3-4, pp. 108-115.

Milanovic, M et al. "Senescence-associated reprogramming promotes cancer stemness", Nature, 2018, vol. 553, vol. 7686, pp. 96-100.

Muñoz-Espin, D et al. "Programmed Cell Senescence during Mammalian Embryonic Development", Cell Press, 2013, vol. 155, No. 5, pp. 1104-1118.

Murphy, R C et al. "Lysophospholipid acyltransferases and leukotriene biosynthesis: intersection of the Lands cycle and the arachidonate PI cycle", J. Lipid Res., 2019, vol. 60, No. 2, pp. 219-226.

Nishikiori, M et al. "Determination of Free Fatty Acids in Human Serum by HPLC with Fluorescence Detection", J. Chromatogr. Sci., 2015, vol. 53, No. 4, pp. 537-541.

Pablo, G-E et al. "Analysis of the Bone MicroRNome in Osteoporotic Fractures", Calcif Tissue Int, 2015, vol. 96, No. 1, pp. 30-37.

Pan, Y et al. "Inhibition of Bcl-2/xl With ABT-263 Selectively Kills Senescent Type II Pneumocytes and Reverses Persistent Pulmonary Fibrosis Induced by Ionizing Radiation in Mice", Int J Radiat Oncol Biol Phys. 2017, vol. 99, No. 1, pp. 353-361.

Pan, J et al. "sPLA2 IB induces human podocyte apoptosis via the M-type phospholipase A2 receptor", Sci. Rep., 2014, vol. 4, No. 1, pp. 6660, 15 pgs.

Panach, L et al. "Serum Circulating MicroRNAs as Biomarkers of Osteoporotic Fracture", Calcif Tissue Int., 2015, vol. 97, No. 5, pp. 495-505.

(56) References Cited

OTHER PUBLICATIONS

Penzo, D et al. "Arachidonic Acid Released by Phospholipase A2 Activation Triggers Ca2+-dependent Apoptosis through the Mitochondrial Pathway", J. Biol. Chem., 2004, vol. 279, No. 24, pp. 25219-25225.

Prior, A M et al. Inhibition of Long Chain Fatty Acyl-CoA Synthetase (ACSL) and Ischemia Reperfusion Injury, Bioorg. Med. Chem. Lett., 2014, vol. 24, No. 4, pp. 1057-1061.

Ressler, S et al. "p16 INK4A is a robust in vivo biomarker of cellular aging in human skin", Aging Cell., 2006, vol. 5, No. 5, pp. 379-389.

Roos, C M et al. "Chronic senolytic treatment alleviates established vasomotor dysfunction in aged or atherosclerotic mice Aging Cell.", 2016, vol. 15, No., 5, pp. 973-977.

Baer, Philip A. et al., "Treatment of Osteoarthritis of the Knee with a Topical Diclofenac Solution: A Randomised Controlled, 6-Week Trial", BMC Musculoskeletal Disorders, 6:44; Aug. 8, 2005; https://bmcmusculoskeletdisord.biomedcentral.com/articles/10.1186/1471-2474-6-44; 9 pages.

Flor, Amy C. et al., "A Signature of Enhanced Lipid Metabolism, Lipid Peroxidation and Aldehyde Stress in Therapy-Induced Senescence", Cell Death Discovery, 3:17075; Oct. 30, 2017; https://www.nature.com/articles/cddiscovery201775; 12 pages.

Flaherty, Kevin R., "Zileuton for the Treatment of Idiopathic Pulmonary Fibrosis", NIH: National Library of Medicine; University of Michigan; ClinicalTrials.gov ID NCT00262405; Dec. 3, 2015; https://ctv.veeva.com/study/zileuton-for-the-treatment-of-idiopathic-pulmonary-fibrosis; 7 pages.

Office Action in corresponding Singapore Patent Application No. 11202103736U, dated Oct. 21, 2024, 10 pages.

Aoki et al., "Pioglitazone, a Peroxisome Proliferator-Activated Receptor Gamma Ligand, Suppresses Bleomycin-Induced Acute Lung Injury and Fibrosis", Respiration, Oct. 31, 2008, vol. 77, No. 3, pp. 311-319.

Milam et al., "PPAR-y agonists inhibit profibrotic phenotypes in human lung fibroblasts and bleomycin-induced pulmonary fibrosis", Am J Physiol Lung Cell Mol Physiol., Dec. 27, 2007, vol. 294, No. 5, pp. 891-901.

Shen et al., "Pioglitazone attenuates aging-related disorders in aged apolipoprotein E deficient mice", Experimental Gerontology, Dec. 6, 2017, vol. 102, pp. 101-108.

Yang et al., "The PPARy Agonist Pioglitazone Ameliorates Aging-Related Progressive Renal Injury", J Am Soc Nephrol., 2009, vol. 20, No. 11, pp. 2380-2388.

Written Opinion in corresponding Singapore Patent Application No. 11202103736U, dated Mar. 5, 2025, 8 pages.

* cited by examiner a

ACSL1

ACSL4 b

MBOAT7

COMPOSITIONS FOR THE ELIMINATION OF SENESCENT CELLS

CROSS-REFERENCE TO RELATED APPLICATIONS

This application is the U.S. national stage of International Patent Application No. PCT/EP2019/079133, filed on Oct. 25, 2019 and entitled COMPOSITIONS FOR THE ELIMINATION OF SENESCENT CELLS, which claims the benefit of priority under 35 U.S.C. § 119 from European Patent Application No. 18202657.5, filed Oct. 25, 2018. The disclosures of the foregoing applications are incorporated herein by reference in their entirety.

FIELD OF THE INVENTION

The present invention relates to the field of senolytics and provides a composition useful for the selective elimination of senescent cells and a method of screening for senolytic compounds.

BACKGROUND OF THE INVENTION

Senescent cells were found to accumulate in tissues and organs during the aging process at close proximity of age-related pathologies where they play a critical role in the development and progression of age-related diseases and disorders. Clearance of senescent cells in mouse models using either genetic or pharmacological approaches was shown to extend the health span, to prevent or delay the occurrence of senescence-associated diseases and disorders and the development of frailty. Since then several pharmacological compounds have been identified which were able to selectively eliminate senescent cells and are generally referred to as "senolytics".

Although cellular senescence is a tumor suppressive mechanism which plays an important role in embryonic development (Muñoz-Espin et al. 2013) and wound healing (Demaria et al. 2014), the chronic accumulation of senescent cells in organs and tissue during the aging process is believed to be a major driving force for the development and progression of age-related diseases and disorders. Senescent cells are terminally growth arrested either via the p53-p21$^{CIP1}$ or via the p16$^{INK4a}$-Rb axis, accumulate senescence-associated β-galactosidase activity (SA-β-gal) and display a typical morphology (Campisi and d'Adda di Fagagna 2007). When chronically present, they negatively affect the surrounding tissue by secreting a pro-tumorigenic and pro-inflammatory mixture of cytokines, growth factors and proteases (Acosta et al. 2013; Coppé et al. 2010; Krtolica et al. 2001) termed the senescence-associated secretory phenotype (SASP).

It has been previously described that senescent cells have decreased intracellular levels of arachidonic acid compared to young cells, due to an increase in the release of arachidonic acid into the extracellular medium (Lorenzini et al. 2000).

In contrast to these findings, WO2019070407A1 discloses a method of identifying elevated levels of senescent cells in a mammal by determining an indicator of senescent cells such as e.g. eicosanoids, or the eicosanoid precursor arachidonic acid.

Genetic mouse models using the p16$^{INK4a}$ promoter to visualize and selectively eliminate p16$^{INK4a}$ positive cells convincingly demonstrated that senescent cells accumulate during the aging process in vivo and that the clearance of p16$^{INK4a}$ positive cells increases the health span and impairs the development and progression of senescence-associated diseases and disorders (Baker et al. 2016; Baker et al. 2011). There is compelling evidence for a causal relationship between senescent cells and several age-related diseases and disorders, such as atherosclerosis (Childs et al. 2016; Roos et al. 2016), idiopathic pulmonary fibrosis (Lehmann et al. 2017; Schafer et al. 2017), osteoporosis (Farr et al. 2017; Zhu et al. 2015), post-traumatic osteoarthritis (Jeon et al. 2017), renal aging (Schmitt and Melk 2017; Valentijn et al. 2018), skin aging (Baar et al. 2017; Lammermann et al. 2018; Lewis et al. 2011; Ressler et al. 2006; Yosef et al. 2016), neurodegenerative diseases (Bussian et al. 2018) and impaired adipogenesis (Xu et al. 2015). Furthermore, it was shown that clearance of senescent cells attenuates the negative effects of irradiation- and chemotherapy-induced senescence and restores tissue functionality (Baar et al. 2017; Chang et al. 2016; Dörr et al. 2013; Pan et al. 2017). In addition to age-related diseases and disorders, cellular senescence is also associated with tumor relapse following chemotherapy (Milanovic et al. 2017) and the performance of transplant organs (Braun et al. 2012) highlighting the potential of senolytic therapies.

The list of senolytic compounds and targets comprises inhibitors of the Bcl-2 family (Chang et al. 2016; Pan et al. 2017; Yosef et al. 2016; Zhu et al. 2017; Zhu et al. 2016), Hsp90 inhibitors (Fuhrmann-Stroissnigg et al. 2017), dasatinib (Roos et al. 2016; Schafer et al. 2017; Zhu et al. 2015), FOXO4 (Baar et al. 2017), OXR1 (Zhang et al. 2018), glucose metabolism (Dörr et al. 2013), mitochondria-targeted tamoxifen (MitoTam) or reduction of ATP synthase activity with oligomycin A (Hubackova et al. 2018) and several plant derived compounds, such as quercetin (Roos et al. 2016; Schafer et al. 2017; Zhu et al. 2015), fisetin (Zhu et al. 2017), piperlongumine (Wang et al. 2016a) and an alcoholic extract of solidago virgaurea (Larnmermann et al. 2018).

Combinations of compounds targeting senescent cells have been described. WO2015116735A1 describes methods for treatment of senescent cell associated diseases or disorders by administering a senolytic combination comprising for example dasatinib and quercetin.

However, many of the reported senolytics like navitoclax and dasatinib have serious side effects and most senolytics are not universally effective in all cell types.

Therefore, there is a strong need in the field for improved senolytics with less severe side effects and broad range of applications.

SUMMARY OF THE INVENTION

It is the objective of the present invention, to provide a composition capable of efficiently eliminating senescent cells. It is a further objective of the present invention to provide a method to screen for compounds useful for the selective elimination of senescent cells.

The problem is solved by the present invention.

The inventors have shown that senescent cells comprise an altered lipid metabolism, which can be exploited to selectively eliminate senescent cells. In particular, lyso PC is upregulated in senescent cells, indicating an increased formation of arachidonic acid. In order to prevent cell death due to intracellular accumulation of arachidonic acid, arachidonic acid is metabolized. For example, arachidonic acid is metabolized to eicosanoids by lipoxygenases and cyclooxygenases, or to arachidonyl-CoA, a precursor for enzymatic recycling and degradation processes, by enzymes with arachidonate-CoA ligase activity, such as ACSL4. Thereby cell death due to high intracellular levels of arachidonic acid is prevented. Accordingly, inhibition of lipoxygenases or cyclooxygenases leads to an increase in arachidonic acid in senescent cells and, thus, to selective elimination of senescent cells.

According to the invention there is provided a composition comprising one or more inhibitors capable of inhibiting at least two of cyclooxygenase-1 (COX-1), cyclooxygenase-2 (COX-2) and lipoxygenase, for use in selectively eliminating senescent cells.

Specifically, the one or more inhibitors are specific inhibitors of COX-1 and/or COX-2.

Specifically, the composition provided herein comprises one or more inhibitors and is capable of inhibiting the enzymatic activity of at least two enzymes selected from the group consisting of COX-1, COX-2 and lipoxygenase.

According to a specific embodiment, the composition provided herein comprises at least two inhibitors. Specifically, the composition provided herein comprises at least one COX-1 or COX-2 inhibitor and at least one lipoxygenase inhibitor. Specifically, the composition comprises at least one COX-1 inhibitor and at least one COX-2 inhibitor. Specifically, the composition provided comprises a cyclooxygenase inhibitor, selected from the group consisting of COX-1 inhibitor, COX-2 inhibitor and COX-1/COX-2 inhibitor, and a lipoxygenase inhibitor. Specifically, the composition provided herein comprises at least one COX-1 inhibitor and at least one lipoxygenase inhibitor, or at least one COX-2 inhibitor and at least one lipoxygenase inhibitor, or at least one COX-1/COX-2 inhibitor and at least one lipoxygenase inhibitor.

According to a further specific embodiment, the composition provided herein comprises at least one dual cyclooxygenase and/or lipoxygenase inhibitor. Specifically, said composition comprises one dual cyclooxygenase and/or lipoxygenase inhibitor and optionally at least one cyclooxygenase or lipoxygenase inhibitor. Specifically, the composition provided herein comprises at least one cyclooxygenase and at least one lipoxygenase inhibitor as combination treatment or it comprises at least one dual inhibitor of cyclooxygenase and lipoxygenase, or any combination thereof.

According to a further specific embodiment, the composition provided herein comprises one or more inhibitors capable of inhibiting COX-1 and COX-2. Specifically, the composition provided herein comprises at least one COX-1/COX-2 inhibitor or at least one COX-1 inhibitor and at least one COX-2 inhibitor.

According to the invention there is further provided a composition comprising one or more inhibitors capable of inhibiting an enzyme with arachidonate-CoA ligase activity for use in selectively eliminating senescent cells. Specifically, said enzyme with arachidonate-CoA ligase activity is any one or more of long-chain-fatty-acid-CoA ligase (ACSL), specifically ACSL1, ACSL3, ACSL4, ACSL5, ACSL6, or SLC27A2 or ACSBG2.

Specifically, the inhibitor capable of inhibiting an enzyme with arachidonate-CoA ligase activity is an ACSL inhibitor, specifically it is an inhibitor capable of inhibiting at least ACSL4. Specifically, the composition described herein comprises one or more ACSL inhibitors. Specifically, the composition described herein comprises an ACSL4 inhibitor.

Specifically, the one or more ACSL inhibitors are triacsin A, triacsin B, triacsin C, triacsin D, analogs of triacsin C, such as e.g. those disclosed in Kim et al. 2012 or Prior et al.

2014, N-ethylmaleimide, 2-fluoropalmitic acid, troglitazone, ciglitazone, pioglitazone or rosiglitazone.

Specifically, the composition described herein comprises one or more SLC27A2 inhibitors, which are preferably selected from triacsin C, 5-bromo-5'-phenylspiro[3H-1,3,4-thiadiazole-2,3'-indoline]-2-one, CB2, CB5, CB6, CB16, NCI-3 and analogs of CB2, CB5, CB6 and CB16. Specifically, inhibitors of SLC27A2 are disclosed in Sandoval et al. 2010.

Specifically, the composition described herein comprises one or more ACSBG2 inhibitors, preferably said inhibitor is 2-(6-HYDROXY-1,3-BENZOTHIAZOL-2-YL)-1,3-THIAZOL-4(5H)-ONE.

According to a specific embodiment of the invention, there is provided a composition comprising one or more inhibitors capable of inhibiting an enzyme with arachidonate CoA ligase activity, specifically long-chain-fatty-acid-CoA ligase (ACSL) 1, ACSL3, ACSL4, ACSL5, ACSL6, SLC27A2 or ACSBG2, and at least one of COX-1, COX-2 or lipoxygenase, for use in selectively eliminating senescent cells.

Specifically, the composition provided herein comprises one or more inhibitors and is capable of inhibiting the enzymatic activity of an enzyme with arachidonate-CoA ligase activity, specifically ACSL1, ACSL3, ACSL4, ACSL5, ACSL6, SLC27A2 and/or ACSBG2, and an enzyme with cyclooxygenase activity, specifically COX-1 and/or COX-2.

Specifically, the composition provided herein comprises at least an ACSL inhibitor and a cyclooxygenase inhibitor. Specifically, the composition provided herein comprises an inhibitor capable of inhibiting at least one of ACSL1, ACSL3, ACSL4, ACSL5, and ACSL6 and an inhibitor capable of inhibiting at least one of COX-1 and COX-2.

Specifically, the composition provided herein comprises one or more inhibitors and is capable of inhibiting the enzymatic activity of an enzyme with arachidonate-CoA ligase activity, specifically ACSL1, ACSL3, ACSL4, ACSL5, ACSL6, SLC27A2 and/or ACSBG2, and an enzyme with lipoxygenase activity.

Specifically, the composition provided herein comprises at least an ACSL inhibitor and a lipoxygenase inhibitor. Specifically, the composition provided herein comprises an inhibitor capable of inhibiting at least one of ACSL1, ACSL3, ACSL4, ACSL5, and ACSL6 and an inhibitor capable of inhibiting at least ALOX5.

Specifically, the senescent cells are characterized by increased intracellular levels of at least one of lysophosphatidylcholine, arachidonic acid and phospholipase A2 activity.

Specifically, the lysophosphatidylcholine is selected from the group consisting of 1-steraroyl-2-hydroxy-sn-glycero-3-phosphocholine (LysoSPC) or 1-palmitoyl-2-hydroxy-sn-glycero-3-phosphocholine (LysoPPC).

Specifically, one or more inhibitors comprised in the composition provided herein are COX-1 and/or COX-2 inhibitors, selected from the group consisting of acetylsalicylic acid, diclofenac, celecoxib, cyclosporin A, ibuprofen, acetaminophen, indomethacin, nabumetone, ketorolac, tenoxicam, tolmetin, piroxicam, fenoprofen, etodolac, naproxen, diflunisal, suprofen, bromfenac, ketoprofen, dihomo-gamma-linolenic acid, icosapent, fluriprofen, mefenamic acid, salsalate, sulindac, salicylic acid, lumiracoxib, O-acetyl-L-serine, phenacetin, fluriprofen methyl ester, metamizole, nitroaspirin, meloxicam, flufenamic acid, oxaprozin, tiaprofenic acid, magnesium salicylate, diethylcarbamazine, lornoxicam, carprofen, phenylbutazone, nepafenac, antipyrine, antrafenine, choline magnesium trisalicylate, triflusal, niflumic acid, dexibuprofen, aceclofenac, acemetacin, droxicam, loxoprofen, tolfenamic acid, dexketoprofen, talniflumate, propacetamol, trolamine salicylate, phenyl salicylate, bufexamac, glycol salicylate, menthyl salicylate, FK-506, lenalidomide, rofecoxib, valdecoxib, cimicoxib, chlorphenesin, clodronic acid, seliciclib, drospirenone, triamcinolone, pomalidomide, parecoxib, firocoxib, aclofenac, adapalene, thalidomide, etoricoxib, robenacoxib, asaraldehyde, zaltoprofen, deracoxib, dexamethasone, pranoprofen, amfenac sodium monohydrate, ampiroxicam, NS-398, bismuth subsalicylate, diclofenac diethylamine, trometamol, rutaecarpine, salicin, fenbufen, xanthohumol, flunixin meglumin and nimesulide. Preferably, the composition described herein does not comprise quercetin.

Specifically, quercetin is not a cyclooxygenase inhibitor as it is not capable of inhibiting cyclooxygenase activity at an $IC_{50}$ of less than 100 μM (Wang et al. 2000). Specifically, quercetin is not a lipoxygenase inhibitor since it is not able to inhibit lipoxygenase activity at an $IC_{50}$ of less than 3 μM.

Specifically, one or more inhibitors comprised in the composition provided herein are lipoxygenase and/or FLAP (ALOX5AP) inhibitors selected from the group consisting of MK886, zileuton, masoprocol, diethylcarbamazine, azelastine, benoxaprofen, nordihydroguaiaretic acid, abietic acid, esculetin, montelukast, minocycline, MLN-977, rhein, diacerein, nabiximols, fostamatinib, AM103, DG031, fiboflapon, AA-861 and atreleuton.

According to a preferred embodiment, the composition provided herein comprises at least one cyclooxygenase inhibitor selected from the group consisting of acetylsalicylic acid, diclofenac, celecoxib, cyclosporin A and ibuprofen and at least one lipoxygenase inhibitor selected from the group consisting of MK886 and zileuton. Specifically, the composition provided herein comprises acetylsalicylic acid and MK886. Specifically, the composition provided herein comprises diclofenac and MK886. Specifically, the composition provided herein comprises celecoxib and MK886. Specifically, the composition provided herein comprises acetylsalicylic acid, diclofenac or celecoxib and cyclosporin A and MK886.

Specifically, one or more inhibitors comprised in the composition provided herein are dual cyclooxygenase and lipoxygenase inhibitors, preferably selected from the group consisting of licofelone, darbufelone, CI-987, S-2474, KME-4, Chebulagic acid, balsalazide, mesalazine, sulfasalazine, aminosalicylic acid, meclofenamic acid, morniflumate diarylpyrazole derivatives, thieno[2,3-b]pyridine derivatives, N-substituted 5-aminosalicylicylamides, flavocoxid, indolizine derivatives, LQFM-091, hyperforin, celastrol, BW755C, tepoxalin, b-boswellic acid, D-002, 2,3-diarylxanthones, phenidone and ER-34122.

According to a further specific embodiment, the composition provided herein comprises an additional compound capable of inhibiting intracellular conversion of arachidonic acid. Specifically, said additional compound leads to an increase of arachidonic acid levels. Specifically, said additional compound is any one of a natural compound, an inhibitor of cytochrome P450, an inhibitor of long-chain-fatty-acid-CoA ligase 4 (ACSL4), an inhibitor of a lysophosphatidylcholine acyltransferase or an inhibitor of a fatty acid elongase or any combination thereof.

Specifically, the additional compound is a natural compound, preferably selected from the group consisting of turmeric, rosemary, ginger, oregano, resveratrol, curcumin, cannabinoids, ginseng, saponins, terpenoids, flavonoids, polyphenols, ginkgo biloba, capsaicin, genistein and kaempferol.

Specifically, the additional compound is an inhibitor of cytochrome P450 (CYP2J, CYP2C, CYP4A, CYP4F), preferably selected from the group consisting of sulfaphenazole, avasimibe, benzbromarone, rosiglitazone, troglitazone, cervistatin, warfarin, pioglitazone, lapatinib, trimethoprim, zafirlukast, amodiaquine, nicardipine, simvastatin, fluvastatin, loratadine, ethinylestradiol, irbesartan, quinine, sorafenib, eltrombopag, losartan, licofelone, amitriptyline, atorvastatin, mefenamic acid, meloxicam, piroxicam, erlotinib, pazopanib, diethylstilbestrol, enzalutamide, ponatinib, dabrafenib, enasidenib, lovastatin, montekulast, ketoconazole, felodipine, candesartan cilexetil, clotrimazole, mometasone, salmeterol, raloxifene, fenofibrate, levothyroxine, tamoxifen, oxybutynin, medroxyprogesterone acetate, nifedipine, liotrix, amlodipine, bezafibrate, chloramphenicol, cyclosporin, cimetidine, clopidogrel, cholecalciferol, delavirdine, dextropropoxyphene, etoposide, isoniazid, ketoprofen, metronidazole, nilutamide, nilvadipine, paroxetine, phenelzine, pravastatin, propafenone, pyrimethamine, rofecoxib, rutin, saquinavir, sulfamethoxazole, sulfinpyrazone, tegaserod, terfenadine, thioridazine, ticlopidine, tioconazole, triazolam, troleandomycin, valproic acid, abiraterone, vismodegib, regorafenib, trametinib, idelalisib, lopinavir, celecoxib, efavirenz, rabeprazole, teriflunomide, crisaborole, belinostat, topiroxostat, candesartan, letermovir, rucaparib, opicapone, nabilone, fluvoxamine, fluticasone, fluticasone furoate, fluticasone propionate, bosutinib, cabozantinib, genistein, lenvatinib, atazanavir, bexarotene, deferasirox, quinidine, mifepristone, vemurafenib, sildenafil, diclofenac, fluoxetine, valdecoxib, voriconazole, etodolac, sertraline, glyburide, acenocoumarol, rosuvastatin, imatinib, clozapine, diazepam, progesterone, omeprazole, valsartan, bortezomib, nevirapine, azelastine, lornoxicam, phenylbutazone, etravirine, leflunomide, sitaxentan, aminophenazone, verapamil, etoricoxib, propofol, sulfamoxole, dicoumarol, diltiazem, histamine, moclobemide, selegiline, parecoxib, doconexent, acetyl sulfisoxazole, fluconazole, pantoprazole, desloratadine, miconazole, amiodarone, gemfibrozil, probenecid, teniposide, sulfadiazine, capecitabine, fluorouracil, tranylcypromine, anastrozole, atovaquone, cyclizine, dexfenfluramine, disulfiram, epinephrine, eprosartan, flecainide, indinavir, methazolamide, nelfinavir, olanzapine, pranlukast, promethazine, sulfadimethoxine, sulfamethizole, sulfanilamide, sulfapyridine, methimazole, tolcapone, bicalutamide, armodafinil, agomelatine, noscapine, clevidipine, sulconazole, gefitinib, ticagrelor, ceritinib, floxuridine, lifitegrast, rhein, diacerein, zucapsaicin, stiripentol, lobeglitazone, dosulepin, manidipine, cimicifuga racemose, curcumin, felbamate, piperine, safinamide, irponiazid, oritavancin, masorpocol and pegvisomant.

Specifically, the additional compound is an inhibitor of long-chain-fatty-acid-CoA ligase 4 (ACSL4), preferably selected from the group consisting of triacsin A, triacsin B, triacsin C, triacsin D, troglitazone, ciglitazone, pioglitazone and rosiglitazone.

Specifically, the additional compound is an inhibitor of a lysophosphatidylcholine acyltransferase, specifically an inhibitor of LPCAT1, LPCAT2, LPCAT3, LPCAT4, MBOAT2 and/or MBOAT7, and wherein the inhibitor of a lysophosphatidylcholine acyltransferase is preferably selected from the group consisting of N-phenylmaleimide derivatives, TSI-01 and thimerosal.

Specifically, the additional compound is an inhibitor of a fatty acid elongase, specifically an inhibitor of ELOVL2, ELOVL4 and/or ELOVL5, and wherein the inhibitor of a fatty acid elongase is preferably selected from the group consisting of cycloate, adenosine 5'-hexadecylphosphate, endo-1k, (5)-1y and compound 37, 5,5-dimethyl-3-(5-methyl-3-oxo-2-phenyl-2,3-dihydro-1H-pyrazol-4-yl)-1-phenyl-3-(trifluoromethyl-3,5,6,7-tetrahydro-1H-indole-2, 4-dione) and (3-endo)-3-(phenylsulfonyl)-N-[4-(trifluoromethyl)phenyl]-8-azabicyclo[3.2.1]octane-8-carboxamide.

According to a further specific embodiment, the composition comprises an additional compound capable of manipulating intracellular ATP levels.

Specifically, the additional compound capable of manipulating intracellular ATP levels is an inhibitor of ATP synthases, preferably selected from the group consisting of oligomycin A, inositol nicotinate, bedaquiline, efrapeptins, leucinostatins, tentoxin, tentoxin derivates, angiostatin, enterostatin, melittin, $IF_1$, Syn-A2, Syn-C, resveratrol, piceatannol, diethylstilbestrol, 4-acetoamido-4'-isothiocya-nostilbene-2,2'-disulfonate, 4,4'-D-isothiocyanatostilbene-2, 2-disulfonic acid, kaempferol, morin, apigenin, genistein, biochanin A, daidzein, epicatechin gallate, epigallocatechin gallate, proanthocyanidin, curcumin, phloretin, theaflavin, tannic acid, 4-hydroxy-estradiol, 2-hydroxy-estradiol, $17\alpha$-estradiol, $17\beta$-estradiol, $\alpha$-zearalenol, 6-zearalenol, oligomycin, venturicidin, apoptolidin, ossamycin, cytovaricin, peliomycin, tributyltin chloride, tricyclohexyltin hydroxide, triethyltin sulfate, triphenyltin chloride, dimethyltin 3-hydroxyflavone chloride, diethyltin 3-hydroxyflavone chloride, dibuthyltin 3-hydroxyflavone bromide, dioctyltin 3-hydroxyflavone chloride, diphenyltin 3-hydroxyflavone chloride, diethyltin 3,5,7,2',4'-pentahydroxyflavone chloride, dibutyltin 3,5,7,2',4'-pentahydroxyflavone bromide, diphenyltin 3,5,7,2',4'-pentahydroxyflavone chloride, tributyltin 3-hydroxyflavone, triethyllead, aurovertin, citreoviridin, asteltoxin, rhodamine B, rhodamine 123, rhodamine 6G, rosaniline, malachite green, brilliant green, quinacrine, quinacrine mustard, acridine orange, coriphosphine, pyronin Y, dequalinium, safranin O, Nile blue A, ethidium bromide, tetracaine, dibucaine, procaine, lidocaine, chlorpromazine, trifluoperazine, procainamide, propranolol, octyl guanidine, 1-dansyl amido-3-dimethypropylamine compounds, cetyltrimethylammonium, spermine, spermidine, bathophenan throline-metal chelate, 4,4-diphenyl-2,2-bipyridine, 3-(2-pyridyl)-5,6-diphenyl-1,2,4-triazine, atrazine, atrazine amino derivative, arsenate, aluminium fluoride, beryllium fluoride, scandium fluoride, vanadate, magnesium fluoride, sulfite, thiophosphate, azide, ANPP, phenylglyoxal, butanedione, dansyl chloride, 1-fluoro-2,4-dinitrobenzene, dicarbopolyborate, almitrine, 5-hydroxy-1,2-naphtalene dicarboxylic anhydride, R207910, spegazzinine, n-butanol, terachlorosalicylanilide, dihydrostreptomycin, suramin, Bz-423, DMSO, hypochlorous acid, DDT, diazoxide, HNB, N-sulfonyl or N-alkyl substituted tetrahydrobenzodiazepine derivatives, 4-(N-arylimidazole)-substituted benzopyran derivatives, N-[1-aryl-2-(1-imidazolo)ethyl]-cyanoguanidine derivatives, N-[1-aryl-2-(1-imidazolo)ethyl]-acylguanidine derivatives, O-[1-aryl-2-(1-imidazolo)ethyl]-thiourethane derivatives, dio-9 complex, ethanol and zinc.

Specifically, the additional compound capable of manipulating intracellular ATP levels is an inhibitor of ADP/ATP translocases, preferably selected from the group consisting of clodronic acid, ibipinabant, atractyloside, carboxyatractyloside, bongkrekic acid, isobongkrekic acid, MT-21, closantel, CD437, leelamine, L923-0673, IMD 0354, PI32-0333, S899542, nonactin and S838462.

Specifically, the additional compound capable of manipulating intracellular ATP levels is an inhibitor of glycolysis, preferably selected from the group consisting of 2-deoxy-D-glucose, lonidamine, bromopyruvic acid, phloretin, STF-31, WZB117, 3PO, 3-bromopyruvate, dichloroacetate, oxamic acid, NHI-1, oxythiamine, imatinib, glucosamine, 6-aminonicotinamide, genistein, 5-thioglucose, mannoheptulose, $\alpha$-chlorohydrin, ornidazole, oxalate, glufosfamide, N-(phosphonacetyl)-L-aspartate, 6-methylmercaptopurine riboside, CGP 3466B maleate, sodium monofluorophosphate, DASA-58, DL-serine, dichloroacetic acid, sodium dichloroacetate, nitrofural, 6-AN, fasentin, benserazide, astraglin, resveratrol, chrysin, GEN-27, apigenin, bis-2-(5-phenylacetamido-1,3,4-thiadiazol-2-yl)ethyl sulfide, CB-839, azaserine, acivicin, 6-diazo-5-ox-L-norleucine, thiazolidine-2,4-dione derivatives, compound 968, R-lipoic acid, 1,3,4-thiadiazole compounds, 2-chloropropionate, Nov3r, AZD7545, Pfz3, radicicol, mitaplatin, mito-DCA, phenylbutyrate, 4,5-diarylisoxazoles, VER-246608, betulinic acid, pyruvate analogs containing phosphinate or phosphonate group, CPI-613, M77976, aromatic DCA derivatives, furan and thiophene carboxylic acids, ritonavir, FX11, oxamate, D-fructose-6-phosphate, 6-phosphogluconic acid, N-bromoacetyl-aminoethyl phosphate, 2-carboxyethylphosphonic acid, N-hydroxy-4-phosphono-butanamide, 2-phosphoglyceric acid, iodoacetate, gossypol, bisphosphonate analogs of 1,3-bisphosphoglyceric acid, benzene hexacarboxylic acid, 3-phosphoglyceric acid, phosphonoacetohydroxamic acid, 2-phospho-D-glyceric acid, TLN-232 and CAP-232.

According to a specific embodiment, the composition provided herein prevents or delays the onset of a senescence-related disease or condition.

According to a specific embodiment, the composition provided herein prevents or delays the progression of a senescence-related disease or condition.

According to a specific embodiment, the composition provided herein promotes the regression of a senescence-related disease or condition.

Specifically, the senescence-related disease or condition is selected from cardiovascular diseases, atherosclerosis, cancer, osteoporosis, osteoarthritis, neurological disorders, dementia, cataract, kidney diseases, retinopathy, diabetes, lung fibrosis, vertebral skin degeneration, age-related muscular atrophy, hair loss and skin aging.

According to a specific embodiment, the composition provided herein improves the performance of transplants.

According to a specific embodiment, the composition provided herein prevents or attenuates senescence-associated scar formation and fibrosis.

According to a specific embodiment, the composition ameliorates side effects of chemotherapy and prevents or delays tumor relapse.

Further provided herein is an in vitro method of identifying senescent cells in a subject, comprising the steps of
a) providing a sample of said subject,
b) determining the intracellular level of at least one of lysophosphatidylcholine, arachidonic acid and/or phospholipase A2 activity in said sample,
c) comparing the level of b) to a reference level, wherein the reference level is the intracellular level of at least one of lysophosphatidylcholine, arachidonic acid and/or phospholipase A2 activity in non-senescent cells,
and wherein an increase of at least 2-fold is indicative of the presence of senescent cells in said sample.

Specifically, an increase in the intracellular level of at least one of lysophosphatidylcholine, arachidonic acid and phospholipase A2 activity compared to a reference level of at least 2.5-fold, 3-fold, 3.5-fold, 4-fold, 4.5-fold or 5-fold is indicative of the presence of senescent cells in said sample.

Even more specifically, an increase in the intracellular level of at least one of lysophosphatidylcholine, arachidonic acid and phospholipase A2 activity compared to a reference level, which is at least two-times, three-times, four-times or five-times as high as the respective standard deviation is indicative of the presence of senescent cells in said sample. Preferably, an increase in the level of at least one of lysophosphatidylcholine, arachidonic acid and phospholipase A2 activity compared to a reference level, which is at least twice as high as the respective standard deviation, is indicative of the presence of senescent cells in the sample of a subject.

Further provided herein is a method of screening for candidate compounds for eliminating senescent cells, comprising the steps of a) bringing at least one test compound in contact with a sample of senescent cells, b) measuring the intracellular level of arachidonic acid and/or measuring apoptosis and/or measuring cell viability, and c) selecting the test compounds which cause an intracellular accumulation of arachidonic acid, increased apoptosis and/or reduced cell viability in the senescent cells contacted with the test compound compared to untreated senescent cells.

According to a specific embodiment, the compound used in the composition described herein is identified according to the screening method described herein.

According to a specific embodiment, the composition for use in selectively eliminating senescent cells comprises at least one cyclooxygenase inhibitor inhibiting or eliminating COX-1 and COX-2 activity. Specifically, the composition provided herein comprises at least one cyclooxygenase inhibitor and at least one lipoxygenase inhibitor, wherein the subject suffering from or being at risk of developing a senescence-related disease or condition is female.

According to a specific embodiment, the composition for use in selectively eliminating senescent cells comprises at least one cyclooxygenase inhibitor inhibiting COX-1 and COX-2. Specifically, the composition provided herein comprises at least one cyclooxygenase inhibitor inhibiting COX-1 and COX-2, wherein the subject suffering from or being at risk of developing a senescence-related disease or condition is male.

FIGURES

FIG. 1: Lysophosphatidylcholines are elevated in senescent cells. (a) Intracellular levels of lyso PPC (16:0 lyso PC) and lyso SPC (18:0 lyso PC) are increasing during the replicative lifespan of HDF from three different donors, mirroring the increased percentage of replicative senescent cells in HDF cultures at high population doublings (PD). Intracellular levels of lyso PPC (16:0 lyso PC) and lyso SPC (18:0 lyso PC) are increasing in HDF after induction of telomere-independent stress-induced premature senescence with (b) hydrogen peroxide and (c) Doxorubicin. Error bars are presented as mean±standard deviation. Data represent the average of three experiments. Significance levels were denoted as: *P<0.05, P<0.01 and *P<0.001.

Figure 2:
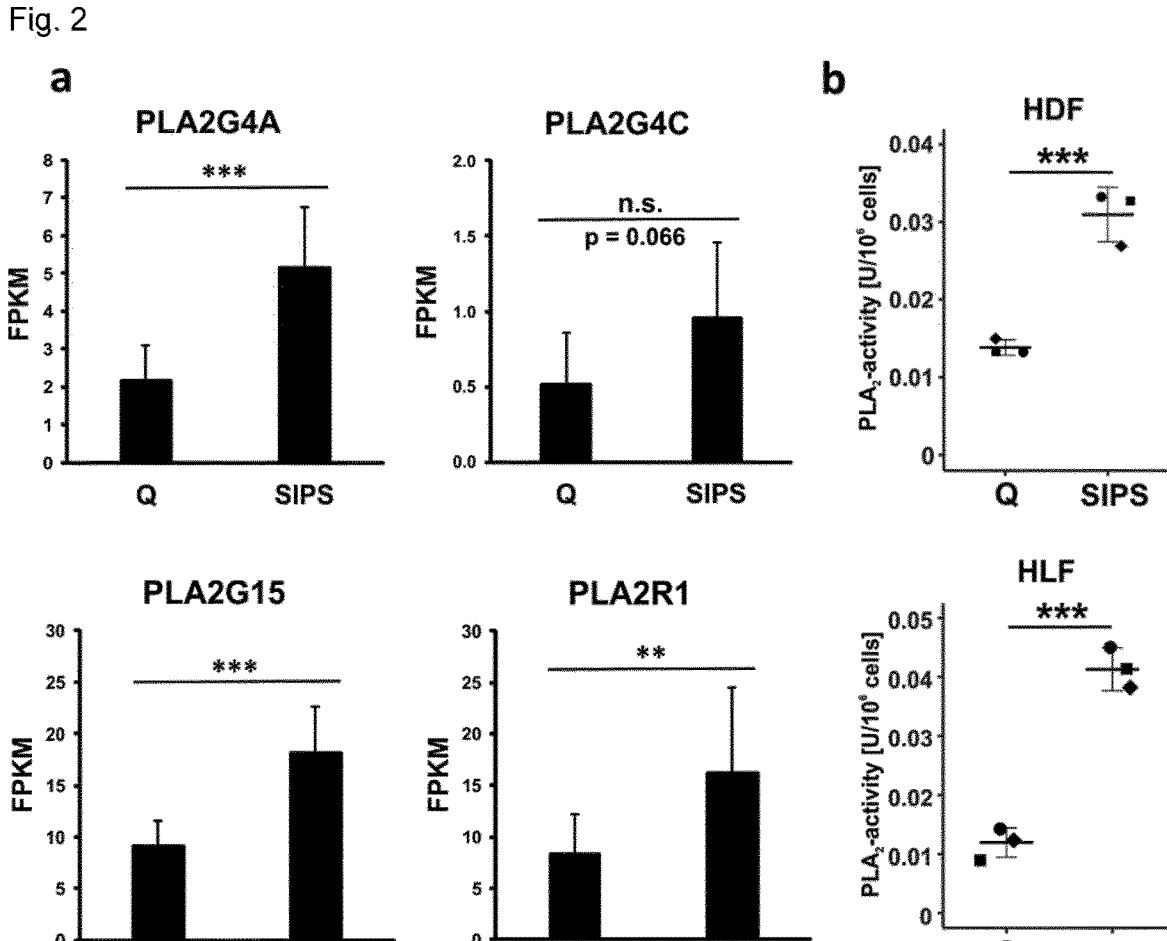

FIG. 2: Phospholipases with PLA$_2$ activity and secretory phospholipase A2 receptor are increased in SIPS HDFs and HLFs. (a) The transcription levels of several genes that either encode for enzymes with PLA$_2$ activity or are capable of increasing the intracellular PLA2 activity by other means are elevated in stress-induced premature senescent HDF, indicating that enzymatic hydrolysis is a likely source for the high levels of lyso PC in senescent cells. PLA2G4A, PLA2G4C and PLA2R1 are all known to produce arachidonic acid as product besides the lyso PCs during this process. (b) PLA2 activity is elevated in stress-induced premature senescent HDF and HLFs from three different donors, as measured with the EnzChek™ Phospholipase A2 Assay Kit (ThermoFisher Scientific; E10217). Data represent the average of three experiments. Significance levels were denoted as: *P<0.05, P<0.01 and *P<0.001.

Figure 3:
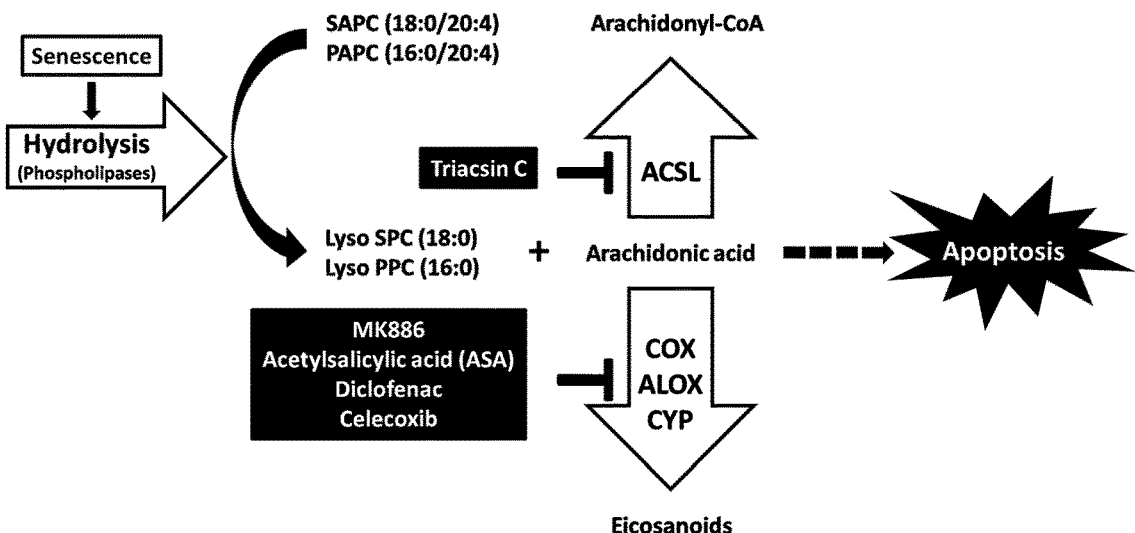

FIG. 3: Overview of the pathway exploited by the senolytic compositions described herein: In senescent cells the lipid metabolism, specifically the metabolism of arachidonic acid, is altered. Senescent cells comprise increased levels of arachidonic acid, which is metabolized into eicosanoids by e.g. COX and ALOX or converted into arachidonyl-CoA and thereby made available for re-acylation and degradation processes (Murphy and Folco 2019). Inhibition of COX and ALOX or ACSL4 leads to accumulation of arachidonic acid in senescent cells, which in turn leads to induction of apoptosis.

Figure 4:
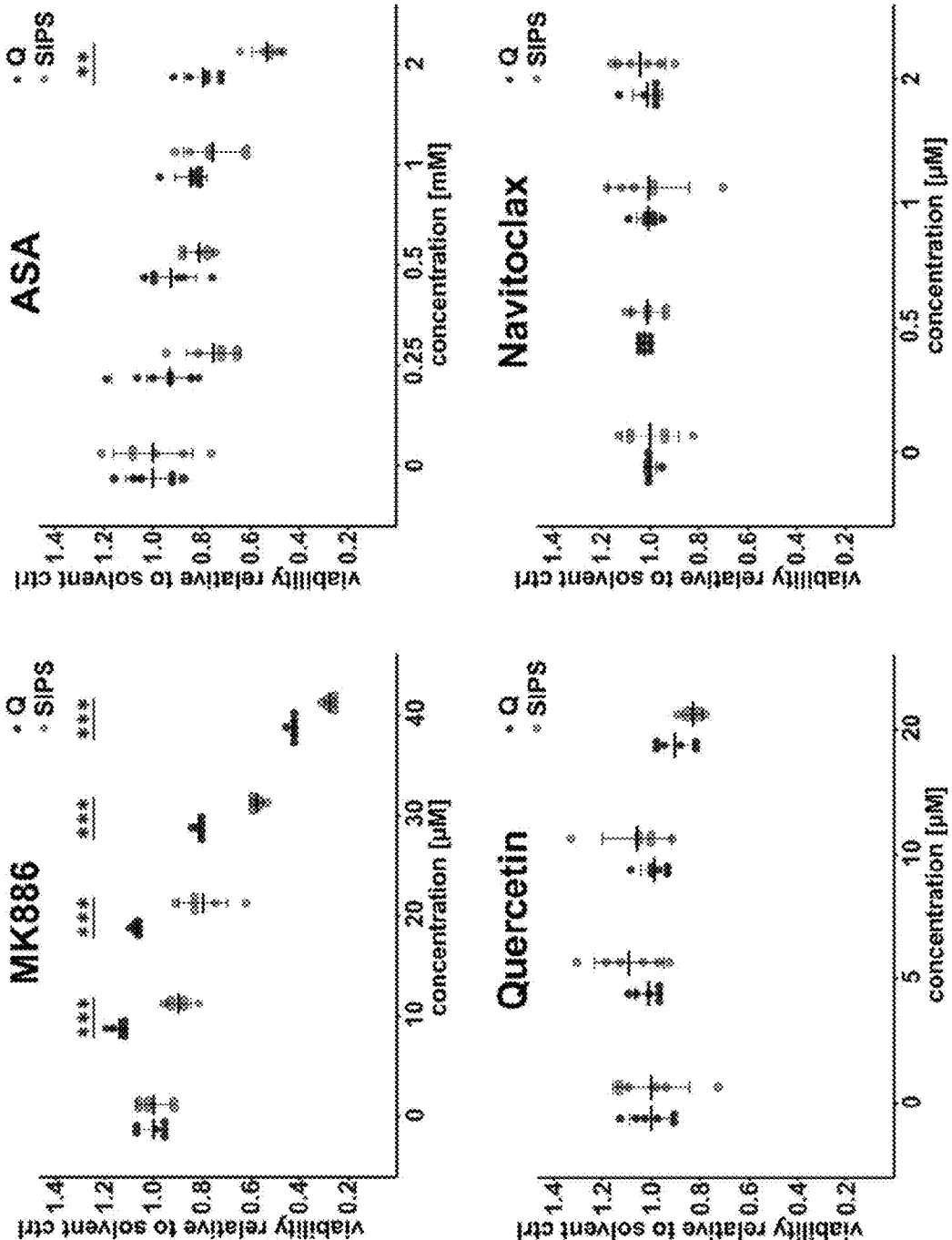

FIG. 4: Senolytic effect of the COX-1/2 inhibitor ASA and ALOX-inhibitor MK886 alone versus prior-art senolytics Quercetin and Navitoclax. MK886, ASA and reported senolytics Quercetin and Navitoclax were tested on H$_2$O$_2$-induced premature senescent human dermal fibroblasts (SIPS) as compared to control quiescent cells (Q). MK886 and ASA showed a significant senolytic effect in SIPS HDFs, whereas this was not the case for Quercetin or Navitoclax. Error bars are presented as mean±standard deviation. Data represent the average of six experiments. Significance levels were denoted as: *P<0.05, P<0.01 and *P<0.001.

Figure 5:
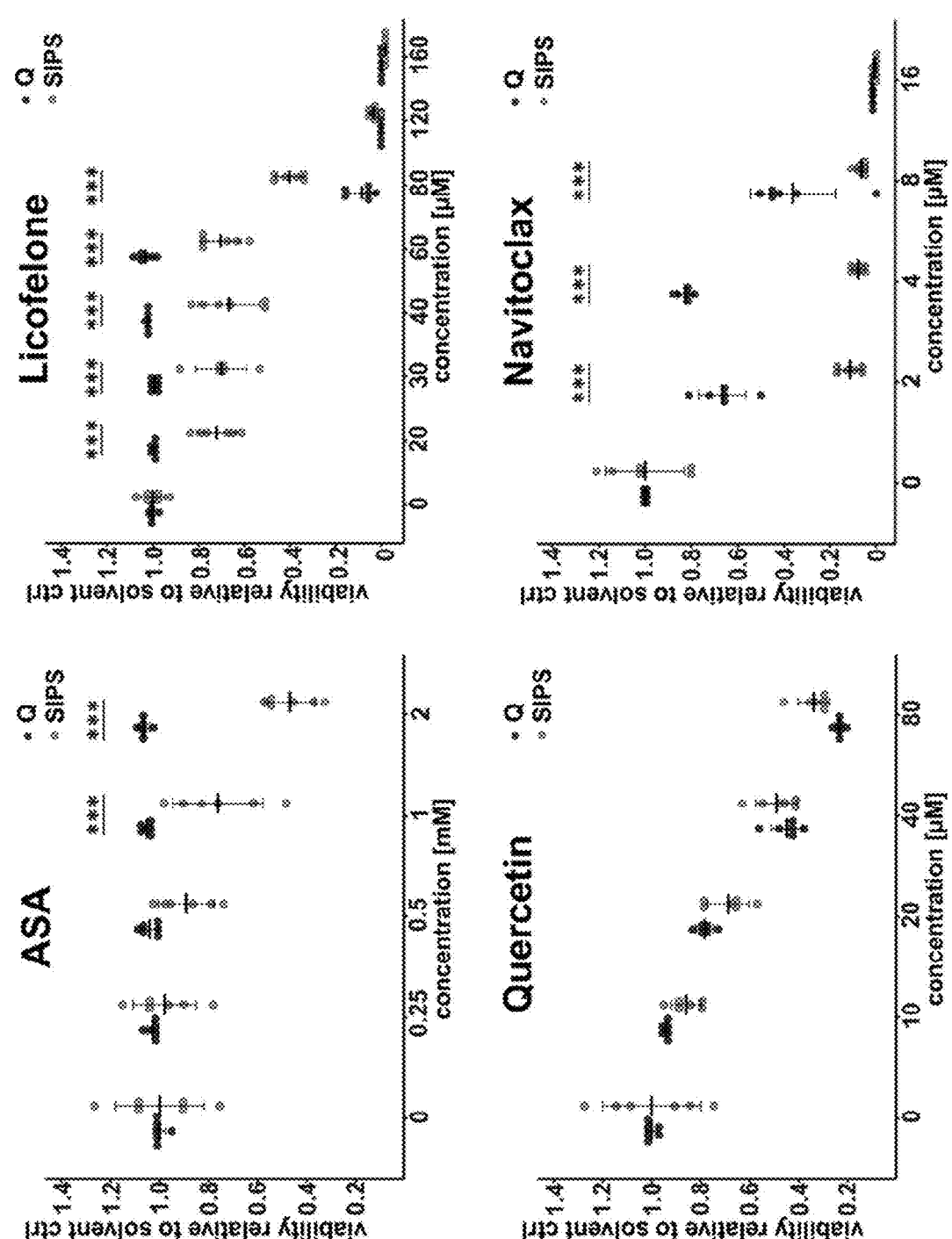

FIG. 5: Senolytic effect of the COX-2/ALOX dual inhibitor Licofelone and the COX-1/2 inhibitor ASA alone versus prior-art senolytics. Licofelone, ASA and reported senolytics Quercetin and Navitoclax were tested on doxorubicin-induced premature senescent HUVECs (SIPS) as compared to control quiescent cells (Q). Licofelone, ASA as well as Navitoclax showed a significant senolytic effect in SIPS HUVECs, whereas this was not the case for Quercetin. Error bars are presented as mean±standard deviation. Data represent the average of six experiments. Significance levels were denoted as: *P<0.05, P<0.01 and *P<0.001.

Figure 6:
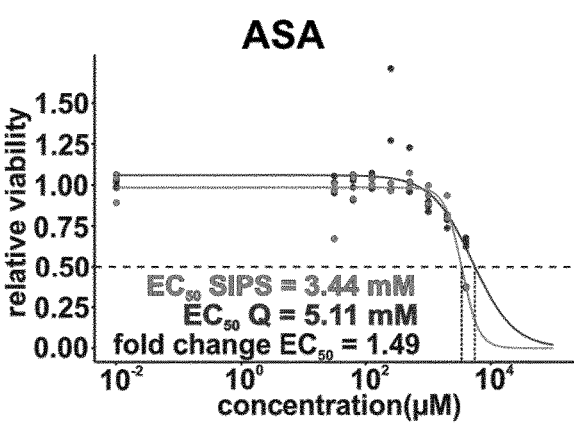
Figure 6:
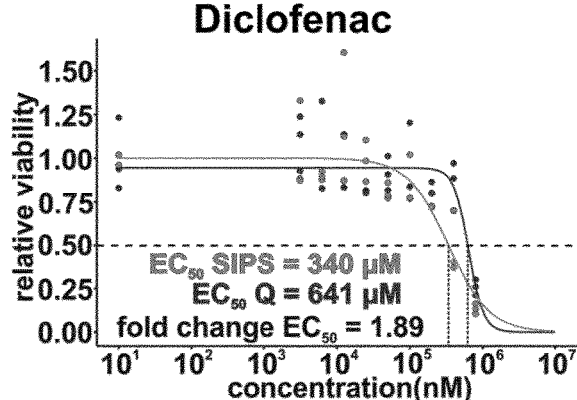
Figure 6:
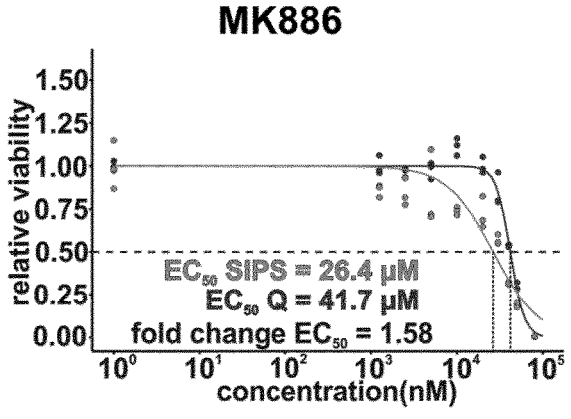
Figure 6:
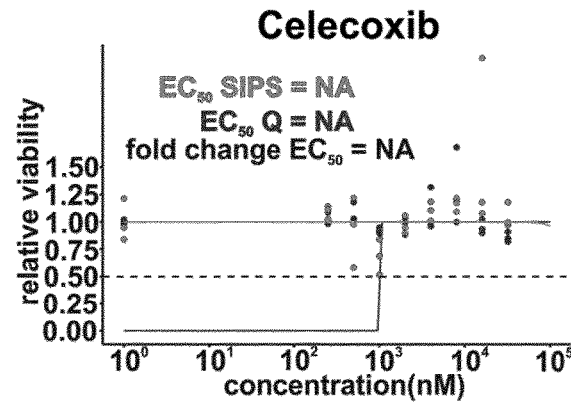
Figure 6:
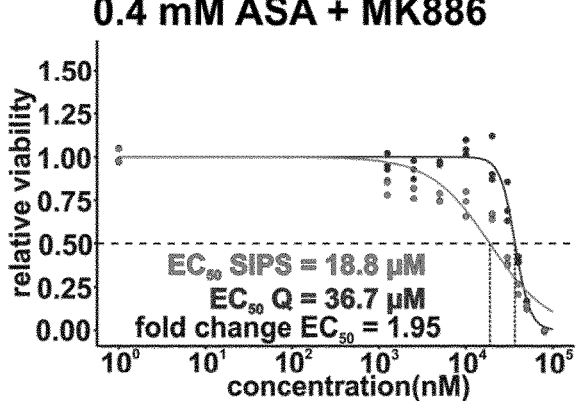
Figure 6:
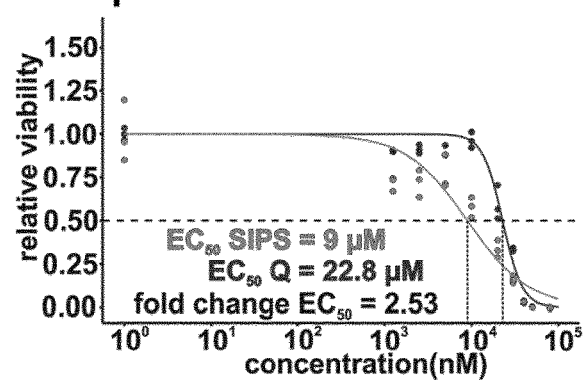
Figure 6:
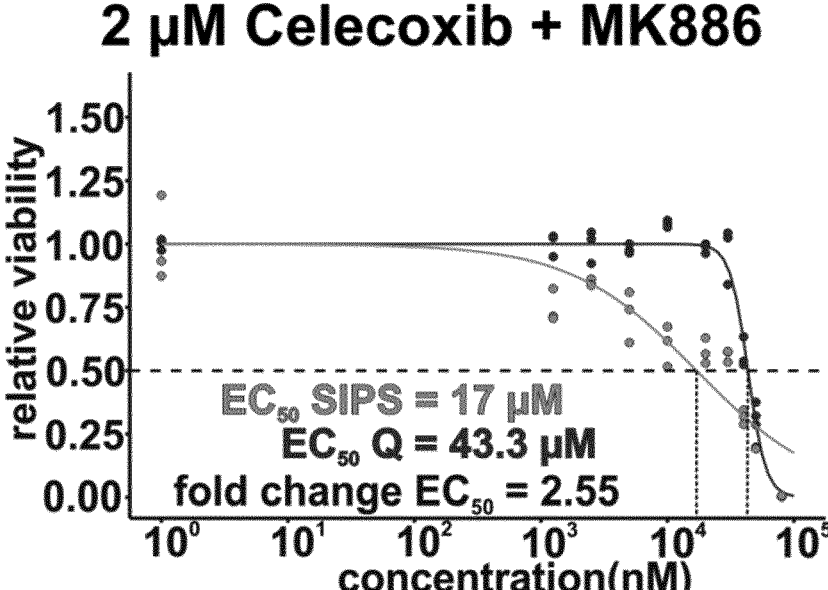

FIG. 6: Synergistic effect of combined inhibition of cyclooxygenase and lipoxygenase in HDF161. Doxorubicin-induced premature senescent HDF161 (SIPS) and quiescent control cells (Q) were either treated with the ALOX-5 inhibitor MK886, the COX-1/2 inhibitors ASA and Diclofenac or the COX-2 specific inhibitor Celecoxib alone or in combination using either 0.4 mM ASA, 50 μM Diclofenac or 2 μM Celecoxib combined with increasing concentrations of MK886. The inhibition of a single AA-metabolizing enzyme was not sufficient to decrease the cell viability in senescent cells as seen with Celecoxib alone. The combination of MK886 with any cyclooxygenase inhibitor (COX-1/2 or COX-2-specific) showed a synergistic effect, demonstrated by the reduction in the EC$_{50}$ value of senescent cells and the increase in the fold change between the EC$_{50}$ of senescent versus quiescent cells. Data represent the average of three experiments.

Figure 7:
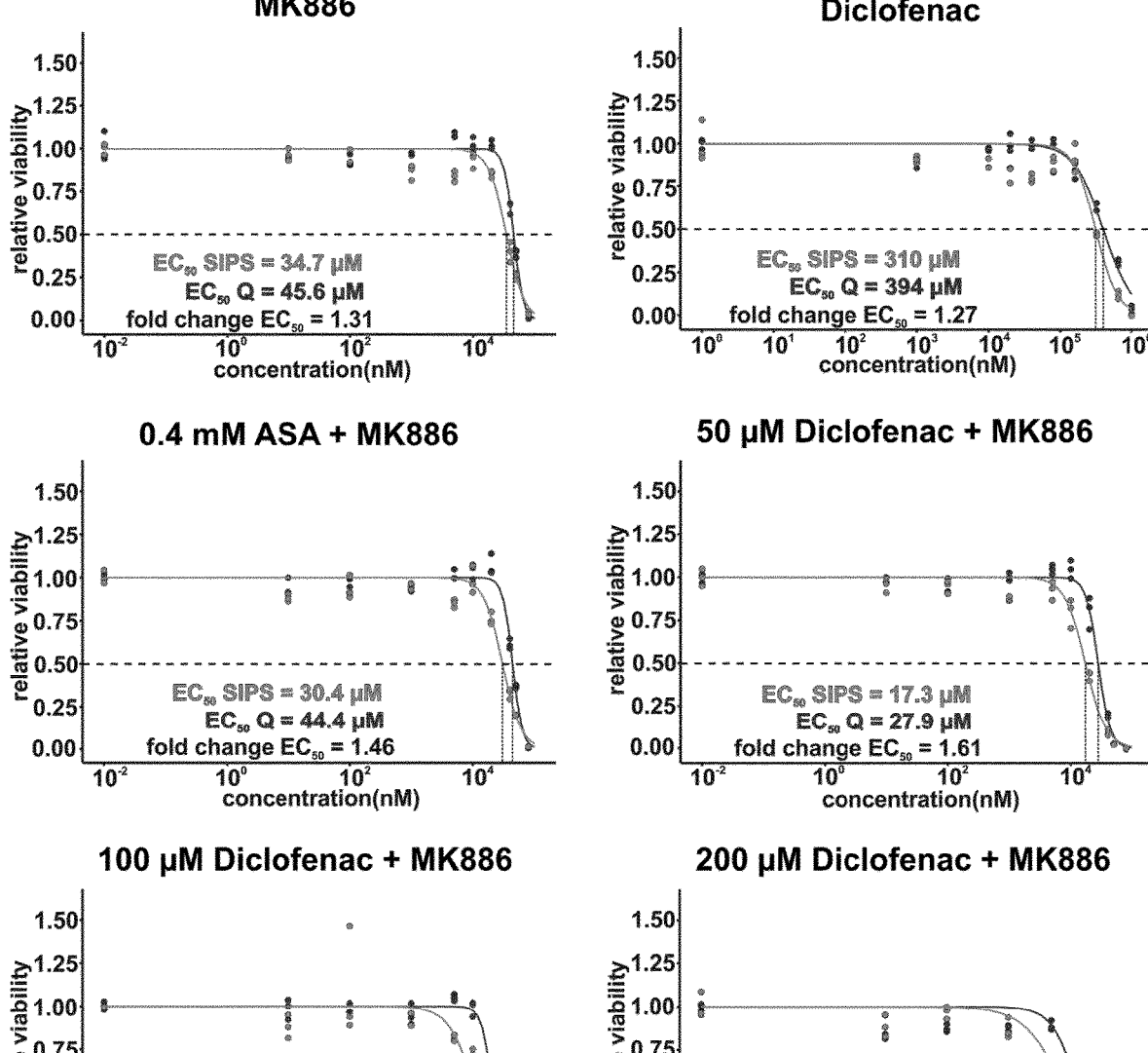

FIG. 7: Synergistic effect of combined inhibition of cyclooxygenase and lipoxygenase in HDF164. Doxorubicin-induced premature senescent HDF164 (SIPS) and quiescent control cells (Q) were either treated with the ALOX-5 inhibitor MK886 and the COX-1/2 inhibitor Diclofenac alone or in combination using either 40.4 mM ASA or 50, 100 or 200 μM Diclofenac combined with increasing concentrations of MK886. The combination of MK886 with a cyclooxygenase inhibitor showed a synergistic effect by reducing the $EC_{50}$ value of senescent cells and increasing the fold change between the $EC_{50}$ of senescent versus quiescent cells. Data represent the average of three experiments.

Figure 8:
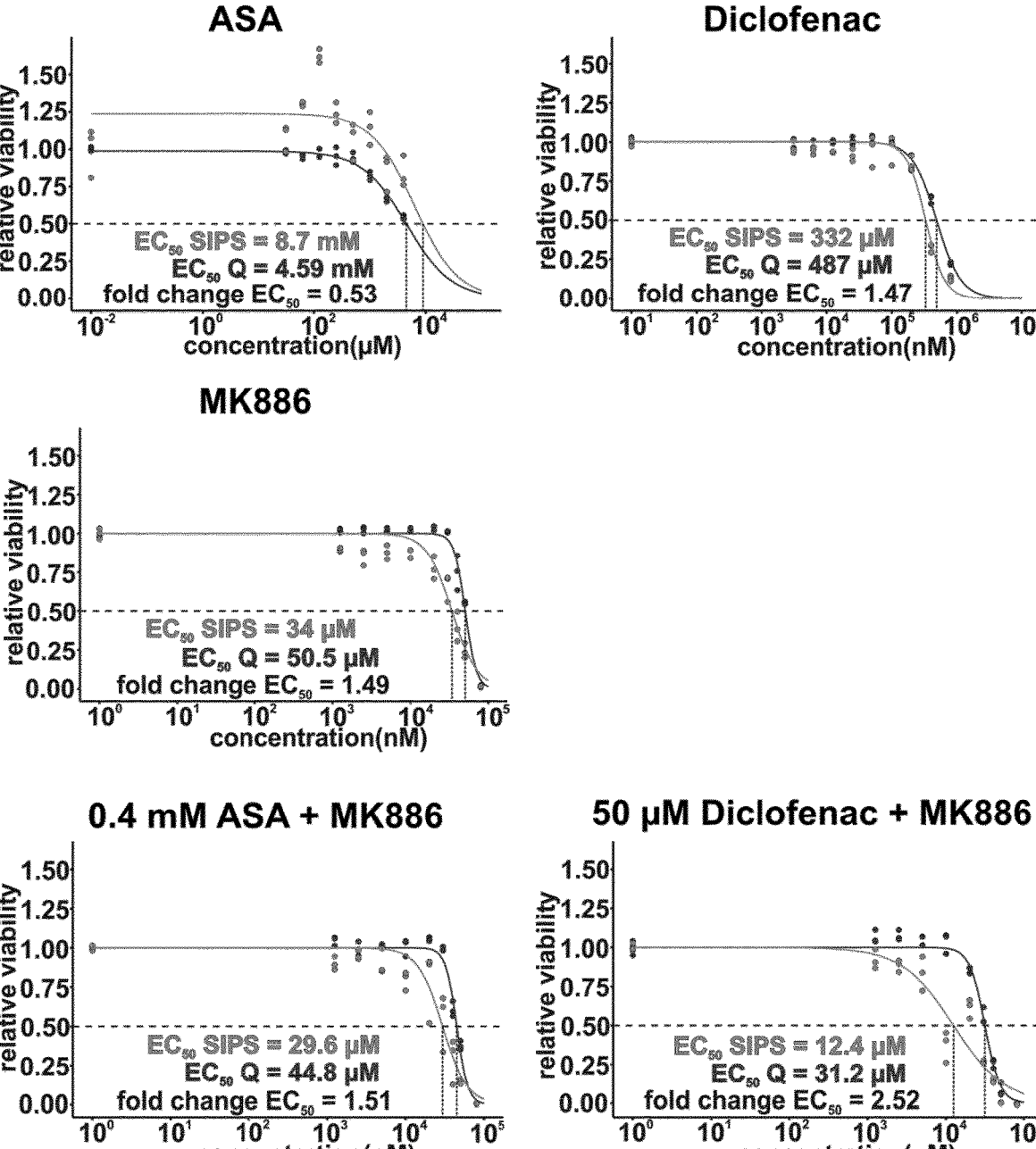

FIG. 8: Synergistic effect of combined inhibition of cyclooxygenase and lipoxygenase in fHDF166. Doxorubicin-induced premature senescent fHDF166 (SIPS) and quiescent control cells (Q) were either treated with the ALOX-5 inhibitor MK886 and the COX-1/2 inhibitors ASA and Diclofenac alone or in combination using either 0.4 mM ASA or 50 μM Diclofenac combined with increasing concentrations of MK886. The combination of MK886 with a cyclooxygenase inhibitor showed a synergistic effect by reducing the $EC_{50}$ value of senescent cells and increasing the fold change between the $EC_{50}$ of senescent versus quiescent cells. Data represent the average of three experiments.

Figure 9:
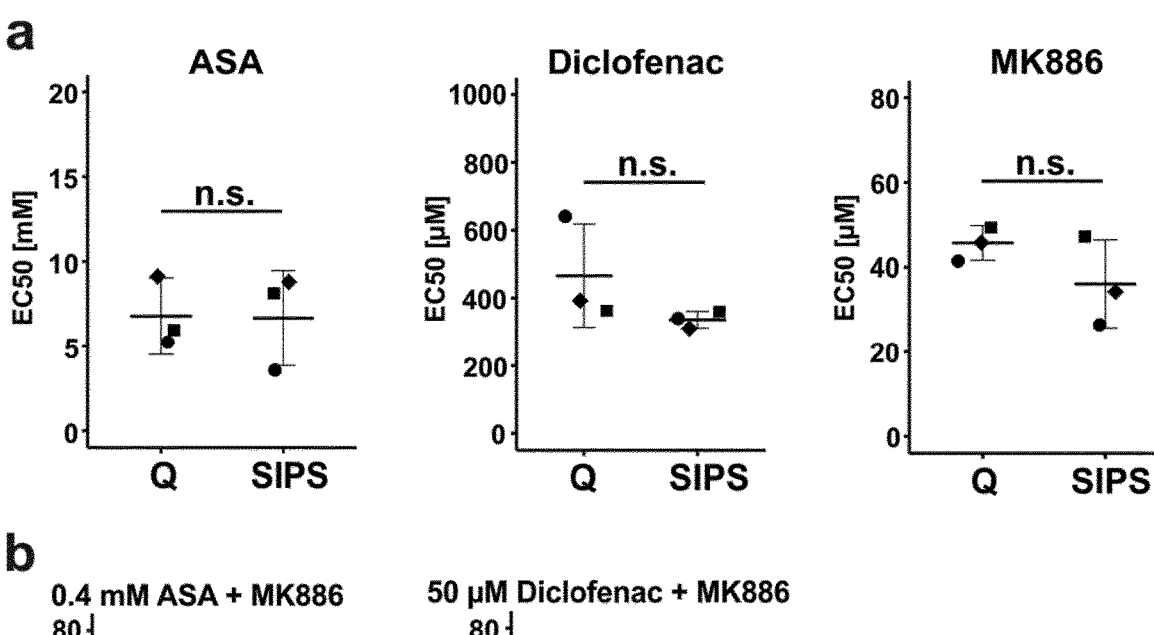
Figure 9:
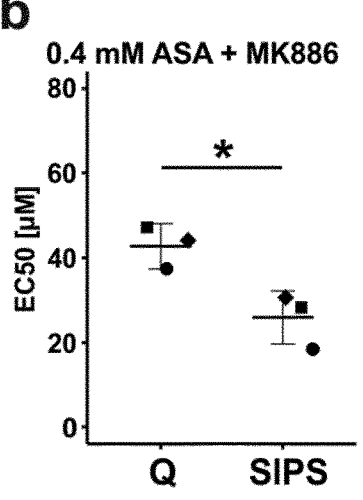
Figure 9:
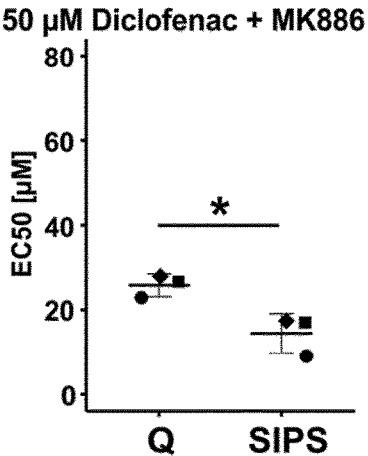
Figure 9:
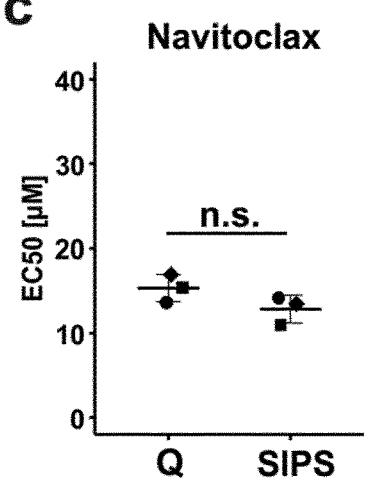
Figure 9:
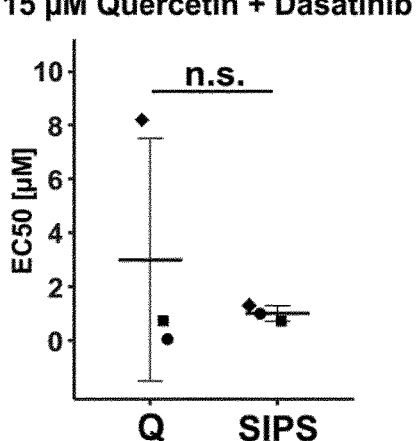

FIG. 9: Synergistic effect of combined inhibition of cyclooxygenase and lipoxygenase in HDF (combined data of three donors). (a) Doxorubicin-induced premature senescent HDF76, HDF161, HDF164 (SIPS) and quiescent control cells (Q) were either treated with the ALOX-5 inhibitor MK886 and the COX-1/2 inhibitors ASA and Diclofenac alone or (b) in combination using either 0.4 mM ASA or 50 μM Diclofenac combined with increasing concentrations of MK886. The combination of MK886 with a cyclooxygenase inhibitor showed a synergistic effect by reducing the $EC_{50}$ value of senescent cells and increasing the fold change between the $EC_{50}$ of senescent versus quiescent cells. (c) Navitoclax as well as 15 μM Quercetin combined with increasing concentrations of Dasatinib showed no senolytic effect in HDFs. Error bars are presented as mean±standard deviation. Data represent the average of three biological replicates. Significance levels were denoted as: *P<0.05, P<0.01 and *P<0.001.

Figure 10:
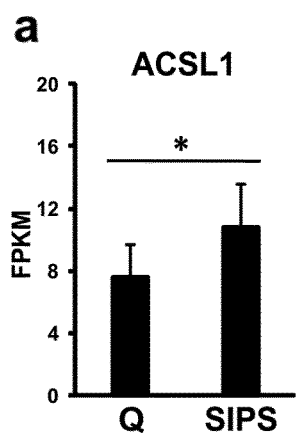
Figure 10:
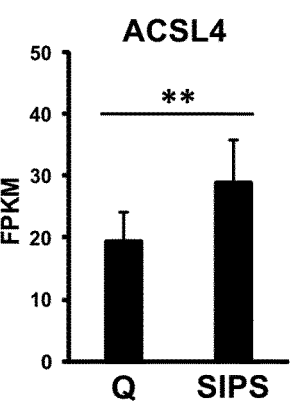
Figure 10:
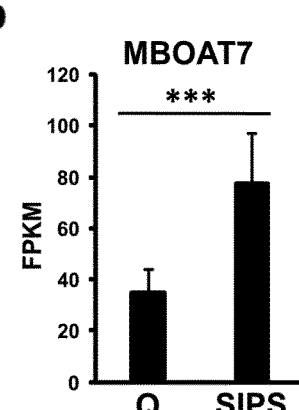

FIG. 10: Key enzymes of the Lands cycle are increased in senescent HDFs. The transcription levels of several genes that either encode for acyl-CoA synthetases or lysophospholipid acyltransferases are elevated in stress-induced premature senescent HDF, indicating that intracellular levels of free AA are regulated within senescent cells by rapid recycling and degradation processes of the Lands cycle. (a) ACSL1 and ACSL4 are required for the activation of free AA by generating AA-CoA, the precursor for degradation or enzymatic reintegration into phospholipids. (b) MBOAT7 is the key enzyme for reintegration of AA-CoA into phosphoinositol. Data represent the average of three experiments. Significance levels were denoted as: *P<0.05, P<0.01 and *P<0.001.

Figure 11:
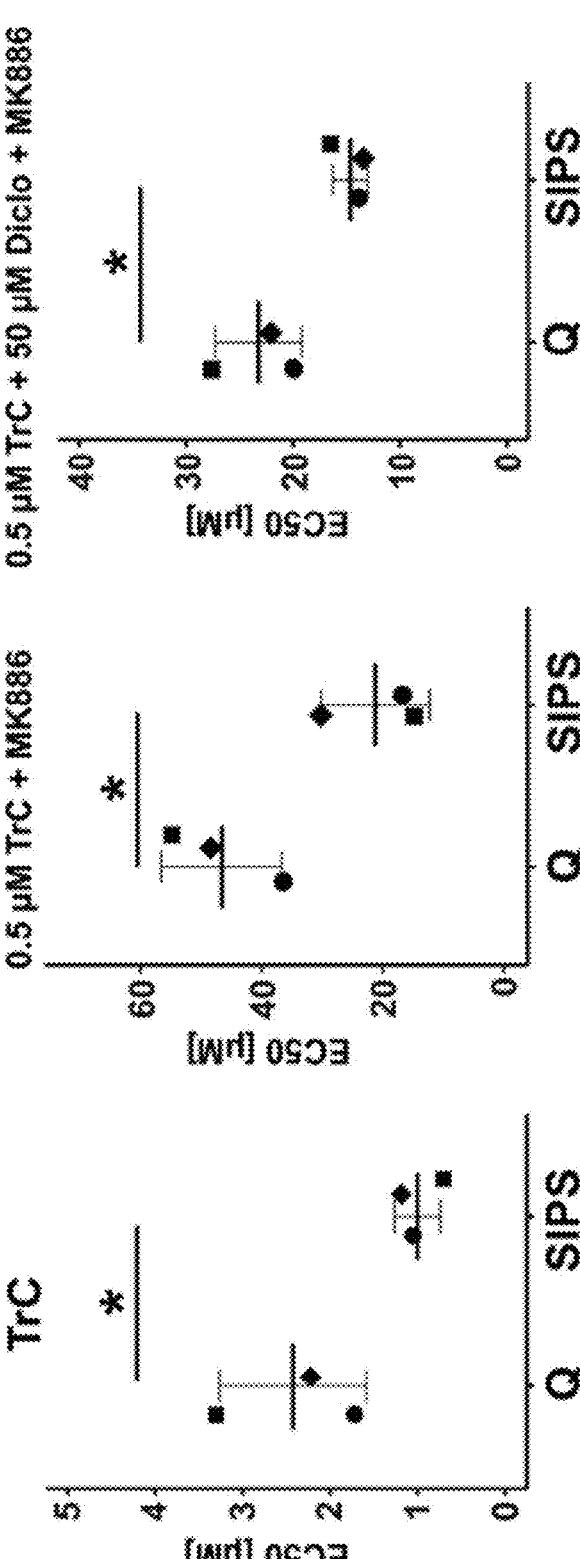

FIG. 11: Inhibition of long-chain-fatty-acid-CoA ligase 4 (ACSL4) is senolytic and has a synergistic effect when combined with inhibition of cyclooxygenase and lipoxygenase in HDF (combined data of three donors). Doxorubicin-induced premature senescent HDF76, HDF161, HDF164 (SIPS) and quiescent control cells (Q) were either treated with the ACSL4 inhibitor Triacsin C (TrC) alone or in combination using either 0.5 μM TrC or 50 μM Diclofenac combined with increasing concentrations of MK886. ACSL4 inhibition alone showed a potent senolytic effect in HDFs. In addition, the combination of lipoxygenase and cyclooxygenase inhibitors with Trc showed a synergistic effect by reducing the $EC_{50}$ value of senescent cells and increasing the fold change between the $EC_{50}$ of senescent versus quiescent cells, as compared to FIG. 9. Error bars are presented as mean±standard deviation. Data represent the average of three biological replicates. Significance levels were denoted as: *P<0.05, P<0.01 and *P<0.001.

Figure 12:
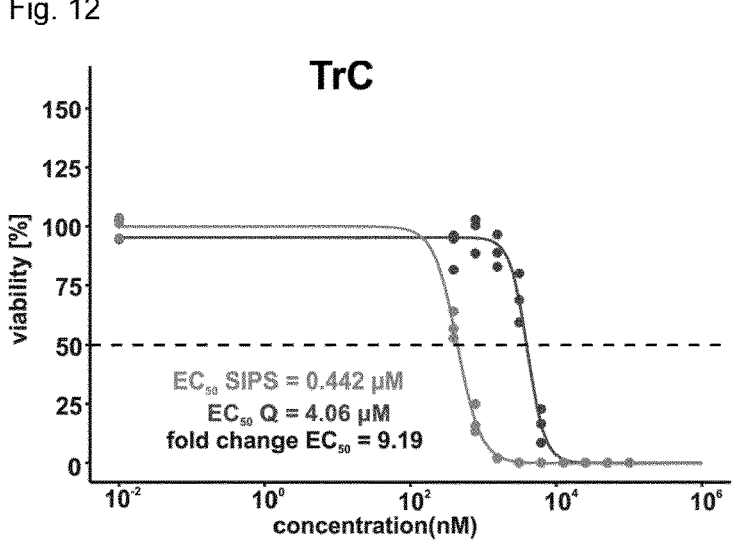
Figure 12:
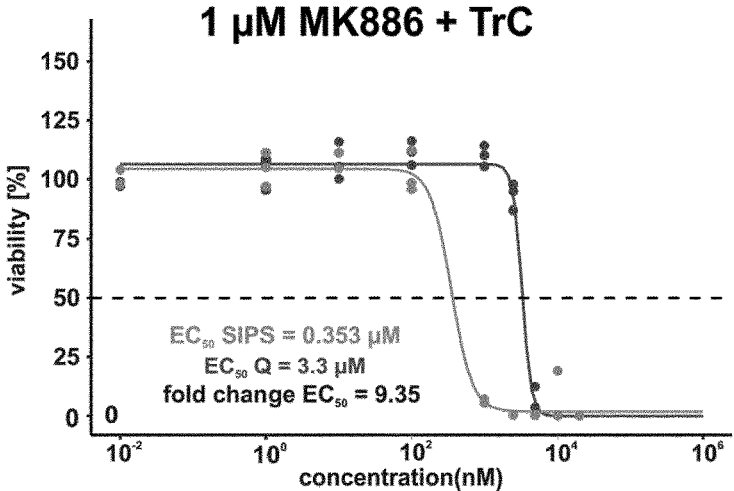
Figure 12:
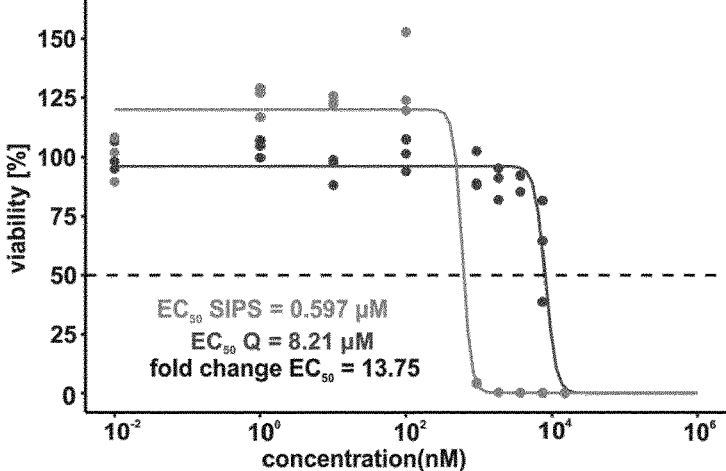

FIG. 12: Inhibition of long-chain-fatty-acid-CoA ligase 4 (ACSL4) is senolytic and has a synergistic effect when combined with inhibition of cyclooxygenase and lipoxygenase in HLFs. Doxorubicin-induced premature senescent HLF102 (SIPS) and quiescent control cells (Q) were either treated with the ACSL4 inhibitor Triacsin C (TrC) alone or in combination using either 1 μM MK886 or 50 μM Diclofenac combined with increasing concentrations of TrC. ACSL4 inhibition alone showed a potent senolytic effect in HLFs. In addition, the combination with lipoxygenase and cyclooxygenase inhibitors showed a synergistic effect by reducing the $EC_{50}$ value of senescent cells and increasing the fold change between the $EC_{50}$ of senescent versus quiescent cells. Data represent the average of three experiments.

Figure 13:
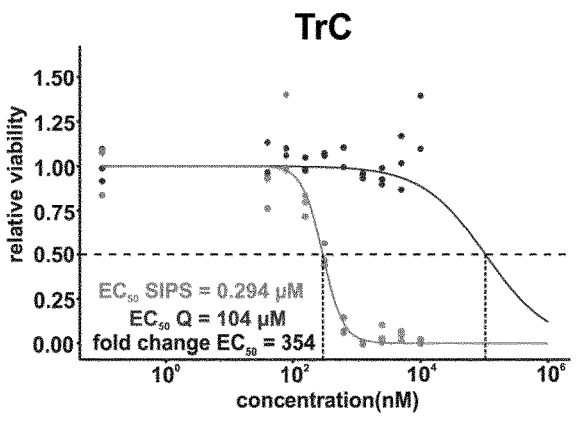
Figure 13:
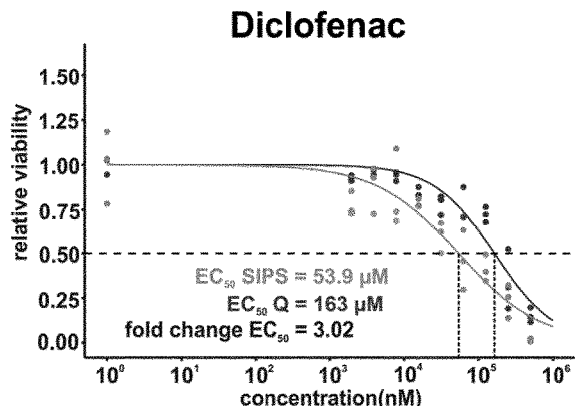
Figure 13:
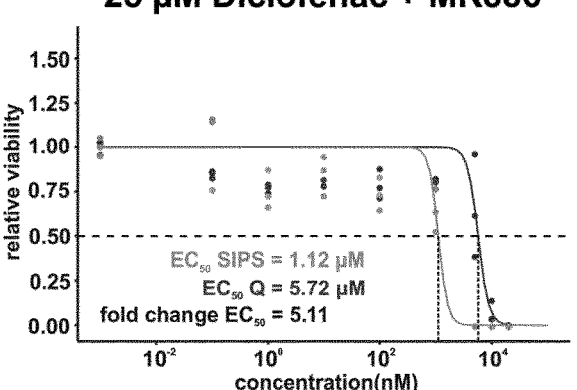
Figure 13:
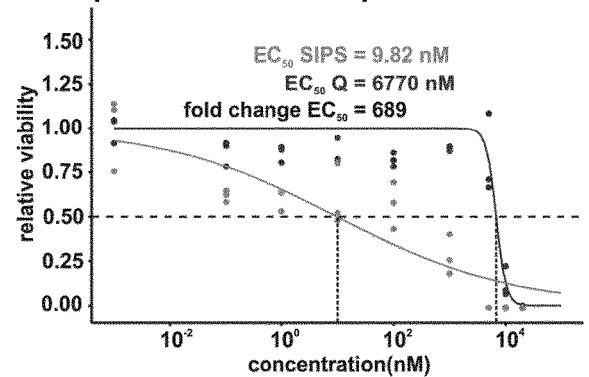

FIG. 13: Inhibition of long-chain-fatty-acid-CoA ligase 4 (ACSL4) is senolytic and has a synergistic effect when combined with inhibition of cyclooxygenase and lipoxygenase in RPTECs. Doxorubicin-induced premature senescent RPTEC1 (SIPS) and quiescent control cells (Q) were either treated with the ACSL4 inhibitor Triacsin C (TrC), the ALOX-5 inhibitor MK886 and the COX-1/2 inhibitor Diclofenac alone or in combination using either 0.1 μM TrC or 25 μM Diclofenac combined with increasing concentrations of MK886. ACSL4 inhibition alone showed a potent senolytic effect in RPTECs. In addition, the combination of lipoxygenase and cyclooxygenase inhibitors with Trc showed a synergistic effect by reducing the $EC_{50}$ value of senescent cells and increasing the fold change between the $EC_{50}$ of senescent versus quiescent cells. Data represent the average of three experiments.

Figure 14:
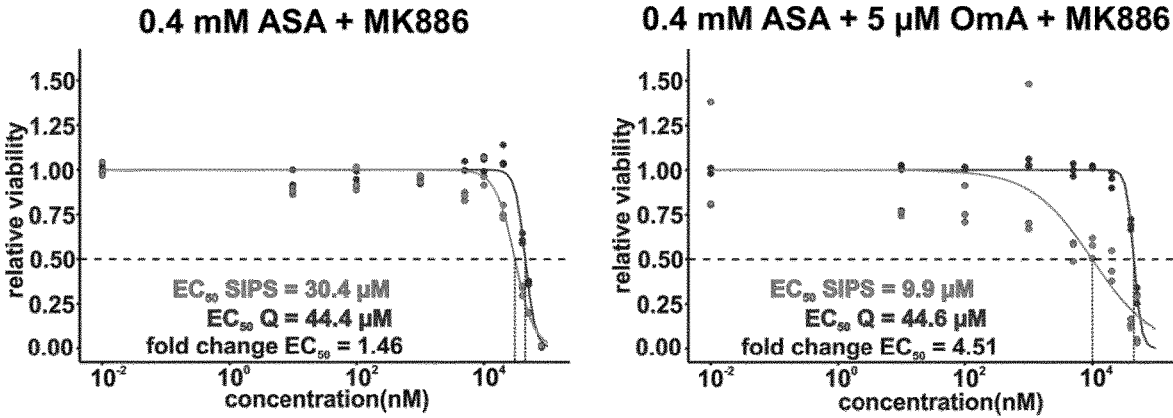

FIG. 14: Synergistic effect of combined inhibition of cyclooxygenase and lipoxygenase in HDF164 can be further enhanced by addition of the ATP synthase inhibitor Oligomycin A. Doxorubicin-induced premature senescent HDF164 (SIPS) and quiescent control cells (Q) were treated with 0.4 mM ASA combined with increasing concentrations of MK886 or in combination with 5 μM Oligomycin A. The combination of the ALOX-5 inhibitor MK886 and the COX-1/2 inhibitor ASA with the ATP synthase inhibitor Oligomycin A showed a synergistic effect by reducing the $EC_{50}$ value of senescent cells and increasing the fold change between the $EC_{50}$ of senescent versus quiescent cells. Data represent the average of three experiments.

Figure 15:
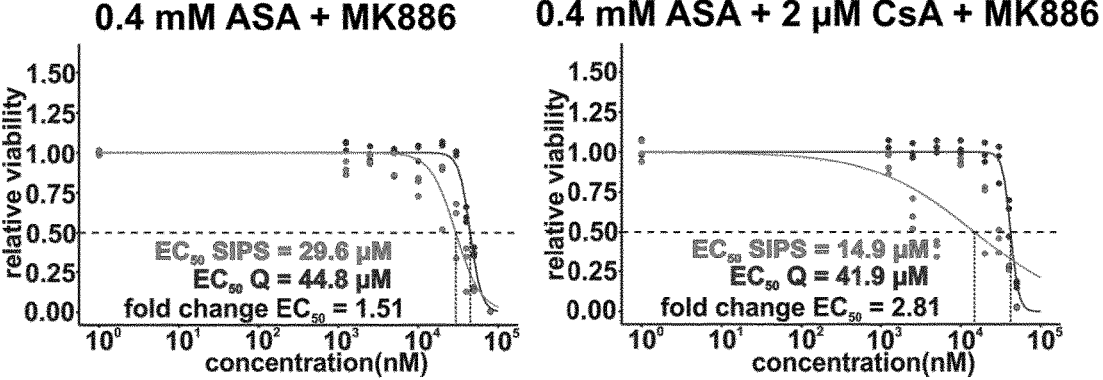

FIG. 15: Synergistic effect of combined inhibition of cyclooxygenase and lipoxygenase in fHDF166 can be further enhanced by addition of the calcineurin inhibitor Cyclosporin A. Doxorubicin-induced premature senescent fHDF166 (SIPS) and quiescent control cells (Q) were treated with 0.4 mM ASA combined with increasing concentrations of MK886 alone or in combination with 2 μM Cyclosporin A. The combination of the ALOX-5 inhibitor MK886 and the COX-1/2 inhibitor ASA with the calcineurin inhibitor Cyclosporin A, which is known to inhibit COX-2 expression, showed a synergistic effect by reducing the $EC_{50}$ value of senescent cells and increasing the fold change between the $EC_{50}$ of senescent versus quiescent cells. Data represent the average of three experiments.

Figure 16:
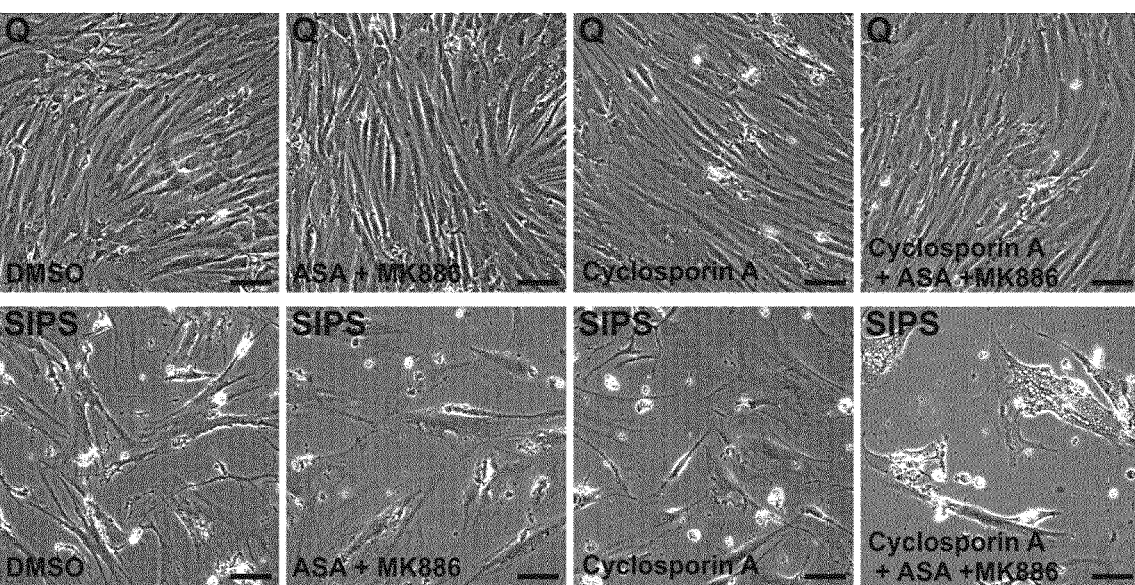

FIG. 16: Combinatorial treatment of SIPS HDFs with Cyclosporin A enhances the senolytic effect of COX/ALOX-inhibitors. Microscopic imaging reveals that combination treatment using MK886 and ASA induces lysis of senescent cells ("SIPS") but not in control cells ("Q"). The senolytic effect of MK886 and ASA in SIPS is further increased upon addition of Cyclosporin A. Such effect is not observed in control cells. Microscopic pictures at 100× magnification. Scale bar, 100 μm.

Figure 17:
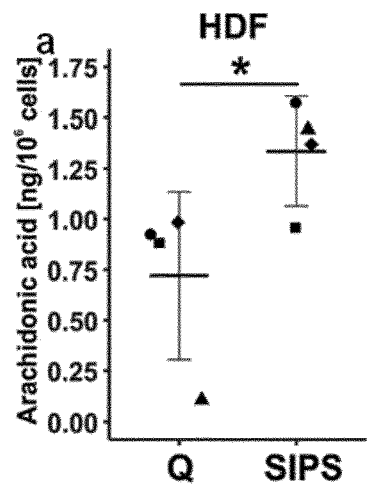
Figure 17:
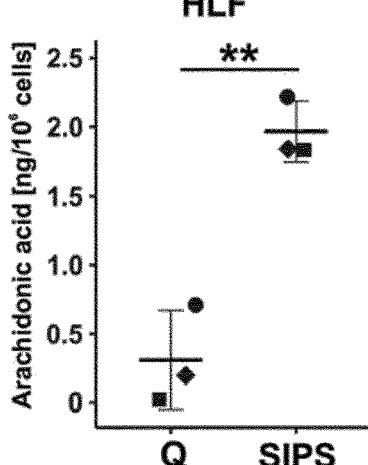

FIG. 17: Intracellular levels of AA are elevated in senescent HDFs and HLFs (SIPS) compared to quiescent control cells (Q) and blocking of eicosanoid synthesis increases the intracellular levels of AA. (a) Intracellular levels of AA of doxorubicin-induced senescent HDF and HLFs compared to quiescent control cells from four and three different donors, respectively. (b) Intracellular levels of AA of HDF161 treated for 6 hrs with the COX-1/2 inhibitor Diclofenac (100 μM) and the ALOX-5 inhibitor MK886 (10 μM) or with the solvent only (1% DMSO). For (a) data represent the average of four and three biological replicates. For (b) data represent one experiment. Error bars are presented as mean±standard deviation. Significance levels were denoted as: *P<0.05, P<0.01 and *P<0.001.

Figure 18:
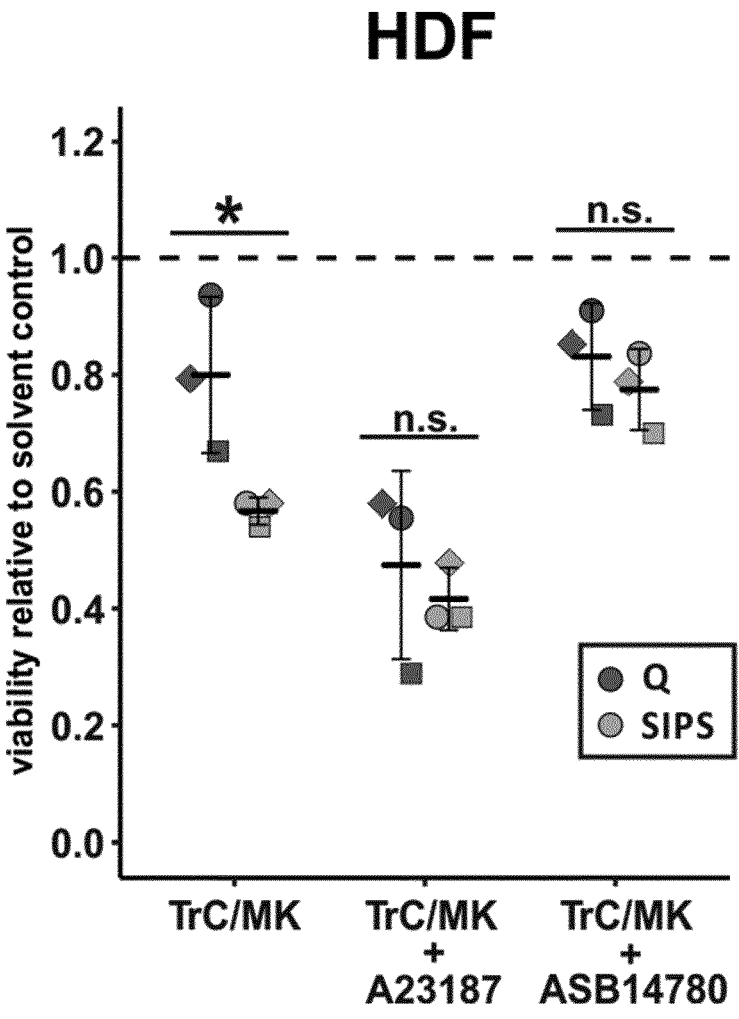

FIG. 18: Senolytic effect of dual inhibition of ACSL4 and ALOXS is dependent on the elevated PLA2-activity of senescent cells. Doxorubicin-induced premature senescent HDF76, HDF85, HDF161 (SIPS) and quiescent control cells (Q) were either treated for 72 hours with the combination of 1 μM ACSL4 inhibitor Triacsin C (TrC) and 1 μM ALOX5 inhibitor MK886 alone or in addition with either 2.5 μM A23187 (cPLA2 activator) or 12.5 μM ASB14780 (cPLA2 inhibitor). ACSL4 inhibition combined with ALOX5 alone showed a significant senolytic effect in HDFs as seen in FIG. 11. The cPLA2 activator A23187 decreased the viability of both, senescent as well as quiescent cells, to a similar level and thereby abolished the senolytic effect. Inhibition of cPLA2 with the small molecule inhibitor ASB14780 on the other hand increased the viability of senescent cells, whereas quiescent cells were only affected to a minor extent. Error bars are presented as mean±standard deviation. Data represent the average of three biological replicates. Significance levels were denoted as: *P<0.05, P<0.01 and *P<0.001.

DETAILED DESCRIPTION

Unless indicated or defined otherwise, all terms used herein have their usual meaning in the art, which will be clear to the skilled person. Reference is for example made to the standard handbooks, such as Sambrook et al, "Molecular Cloning: A Laboratory Manual" (2nd Ed.), Vols. 1-3, Cold Spring Harbor Laboratory Press (1989); Lewin, "Genes IV", Oxford University Press, New York, (1990), and Janeway et al, "Immunobiology" (5th Ed., or more recent editions), Garland Science, New York, 2001.

Specific terms as used throughout the specification have the following meaning.

The terms "comprise", "contain", "have" and "include" as used herein can be used synonymously and shall be understood as an open definition, allowing further members or parts or elements. "Consisting" is considered as a closest definition without further elements of the consisting definition feature. Thus "comprising" is broader and contains the "consisting" definition.

The term "about" as used herein refers to the same value or a value differing by +/−5% of the given value.

Singular and plural forms can be used interchangeably herein if not otherwise indicated.

As used herein, the term "subject" or "individual" or "patient" shall refer to a warm-blooded mammalian, particularly a human being. Alternatively, it may also be an animal, for example mouse, rat, dog, cat, swine, bovine, or a non-human primate.

The term "patient" includes human and other mammalian subjects that receive either prophylactic or therapeutic treatment for a senescence-associated condition or disease or are diagnosed of cellular senescence or a senescence-associated condition or disease.

The term "sample" generally refers to tissue or organ sample, blood, cell-free blood such as serum and plasma, platelet-poor plasma, lymph, urine, saliva and biopsy probes.

Senescent cells were found to accumulate in tissues and organs in response to internal or external stress as well as during the aging process. They play a critical role in the development and progression of senescence-related diseases and disorders. Several pharmacological compounds able to eliminate senescent cells have been identified; however, most senolytics cause serious side effects, exhibit senolytic activity only in specific cell types or lack sufficient effectiveness. Accordingly, there is an urgent need for improved senolytics.

Senescence refers to the gradual deterioration of functional characteristics. Cellular senescence occurs in culture and in vivo as a response to extracellular or intracellular stress and/or due to aging. The senescence response locks cells into a cell-cycle arrest that prevents the propagation of damaged cells and precludes potential malignant transformation. Senescence refers to an array of changes that occurs over time. Compared to a reference cell (e.g., a cell or sample of the same type or age known to be non-senescent), a senescent cell is defined as a cell that shows one, two, three, four, five, six or more or all of any of the following features: a decrease in cell proliferation ability; an accumulation of lipofuscin (e.g., increase in lipofuscin accumulation); an increase in beta-galactosidase activity; an increase in the secretion of members of the senescence-associated secretory phenotype (SASP); an increase of mitochondrial-derived reactive oxygen species; an increase in nuclear DNA damage foci; a shortening of telomeres; increased expression of p16 or p21 or any combination thereof; or a cell or subject shows a process that causes those described above.

The senescent cell may further show a decrease in autophagy activity or a decrease in mitochondrial membrane potential, or shows a process that causes those described above. Compared to a cell or subject such as a known senescent cell or subject, a non-senescent cell or subject may show an increase in cell proliferation ability, a decrease in lipofuscin accumulation, a decrease in β-galactosidase activity, or a combination thereof. Specifically, in the case of a human, a cell or sample that is taken from a person about 30 years or older, about 40 years or older, about 50 years or older, about 60 years or older, about 70 years or older, about 80 years or older, about 90 years or older, may be defined as a senescent cell or sample. In certain cases a cell or sample that is taken from a person about 30 years or younger, 20 years or younger, 10 years or younger or even at the embryonic stage, may be defined as a senescent cell or sample. Specifically, a cell or sample that is taken from a human child suffering from or at risk of developing a senescence-related disease or condition, such as for example diabetes, specifically type I diabetes, may be defined as a senescent cell or sample.

The terms "cellular senescence" and "senescent cells" thus refer to the essentially irreversible growth arrest that occurs when cells that can divide encounter critically short telomeres, oncogenic stress or DNA damage or experience strong mitogenic signals, such as but not limited to oncogenes or highly expressed pro-proliferative genes and a senescent cell, which is a potentially persisting cell that is metabolically active and has undergone widespread changes in protein expression.

The term "senescent cells" specifically refers to cells that express a marker or combination of markers that are characteristic of senescence. According to a specific embodiment, such marker is any one or more of lysophosphatidylcholine, specifically lyso PPC and/or lyso SPC, arachidonic acid and phospholipase A2 activity. Specifically, such marker is an increase in the level, specifically the intracellular level, of any one or more of lysophosphatidylcholines, preferably lyso PPC and/or lyso SPC, arachidonic acid and phospholipase A2 activity. In some embodiments, a senescent cell expresses other markers including but not limited to increased expression relative to a reference, such as a non-senescent cell, in the levels of DNA-damage response (DDR) markers, co-localization of DNA damage proteins like 53BP1 or gammaH2AX with telomeres, as well as the cell cycle inhibitors $p16^{INK4A}$, $p15^{INK4B}$, $p21^{CIP1}$, and p53. DEC1, DCR2, and PAI1 can also be used as senescence biomarkers. In one embodiment, senescent cells express SA-beta-Gal (senescence-associated beta galactosidase) to an extent that staining with X-Gal at pH=6 results in a blue color.

Stress, the natural and in vivo equivalent of which are unknown, causes a senescence arrest without significant telomere erosion. These stresses may include inappropriate substrate, e.g., tissue culture plastic, serum (most cells experience plasma, not serum, in vivo), serum withdrawal, DNA-damage inducing substances or oxidative stress, e.g., culture in atmospheric $O_2$, which is hyperphysiological or exposure to substances that produce reactive oxygen species, such as hydrogen peroxide, paraquat or tert-Butyl hydroperoxide. Cells also enter senescence upon loss of the PTEN tumor suppressor, a phosphatase that counteracts pro-proliferative/pro-survival kinases. Additionally, ectopic expression of the cyclin-dependent kinase inhibitors (CDKis) that normally enforce the senescence growth arrest, notably p21WAF1 and/or $p16^{INK4a}$, may cause senescence.

Aging is a combination of processes of deterioration that follow the period of development of an organism. Aging is generally characterized by a declining adaptability to stress, increased homeostatic imbalance, increase in senescent cells, and increased risk of disease. Because of this, death is the ultimate consequence of aging. Environmental factors may affect aging, for example, overexposure to ultraviolet radiation accelerates skin aging. Different parts of the body may age at different rates. Two organisms of the same species can also age at different rates, making biological aging and chronological aging distinct concepts.

Acceleration of the rate of aging may be induced by stress conditions including, but not limited to chemical, physical, and biological stresses. For example, accelerated aging can be induced by stresses caused by UV and IR irradiation, drugs and other chemicals, chemotherapy, intoxicants, such as but not limited to DNA intercalating and/or damaging agents, oxidative stressors etc; mitogenic stimuli, oncogenic stimuli, toxic compounds, hypoxia, oxidants, exposure to environmental pollutants, for example, silica, exposure to an occupational pollutant, for example, dust, smoke, asbestos, or fumes. All these stressors alone or in combination can also cause cellular senescence. Specifically, senescence is induced by combinations of stresses, e.g., two or more chemical and physical stresses; two or more chemical and biological stresses; two or more physical and biological stresses; chemical, physical, and biological stresses in combination, etc.

Cellular senescence may also be caused by telomeric dysfunction (telomere uncapping) resulting from repeated cell division (termed replicative senescence), mitochondrial deterioration, oxidative stress, severe or irreparable DNA damage and chromatin disruption (genotoxic stress), and the expression of certain oncogenes (oncogene-induced senescence). Stresses that cause cellular senescence can be induced by external or internal chemical and physical insults encountered during the course of the life span, during therapeutic interventions (for example, X-irradiation or chemotherapy), or as a consequence of endogenous processes such as oxidative respiration and mitogenic signals. External mitogenic signals, for example growth-related oncogene alpha (GROa) secretion by tumor cells in close proximity to normal cells or circulating angiotensin II, have also been shown to induce cellular senescence. All somatic cells that have the ability to divide can undergo senescence. Regardless of the disparate mechanisms of senescence-inducing stresses, the senescence program is activated once a cell has sensed a critical level of damage or dysfunction. So far, the senescence growth arrest has been shown to depend on the activities of the major tumor-suppressor pathways controlled by $p16^{INK4a}$ and pRB (retinoblastoma protein), as well as by p53. Some of the molecules involved in pathways upstream and downstream of the senescence-associated phenotype have been used as markers to detect senescent cells in culture and in vivo.

As described herein, senescent cells have an altered lipid metabolism. Specifically, phospholipase A2 activity is upregulated. According to a specific example, the secretory phospholipase A2 receptor (PLA2R1) is upregulated, which induces the production of lyso PCs, leading to a concurrent intracellular release of arachidonic acid (AA). Specifically, senescent cells thus have an increased AA formation rate. According to a further specific example, lysophosphatidylcholine is upregulated. In particular, 1-stearoyl-2-hydroxy-sn-glycero-3-phosphocholine (18:0 lyso PC) and 1-palmitoyl-2-hydroxy-sn-glycero-3-phosphocholine (16:0 lyso PC) are upregulated independent of whether the senescence inducer is telomere dependent (replicative senescence, aging) or independent (stress-induced premature senescence).

Surprisingly, targeting said altered lipid metabolism of senescent cells using a composition capable of inhibiting at least two of COX-1, COX-2 and lipoxygenase, efficiently and selectively eliminates senescent cells of different cell types. Advantageously, numerous cyclooxygenase and lipoxygenase inhibitors exist which are well-studied pharmacological compounds and generally have only mild side effects.

The term "phospholipase A2" or "PLA2" as used herein refers to a superfamily of lipases with PLA2 activity. PLA2 activity refers to the ability of PLA2 enzymes to hydrolyze the fatty acid from the sn-2 position of membrane phospholipids, such as for example phosphatidylcholine. The PLA2 superfamily comprises four main types of enzymes including the secreted PLA2 (sPLA2), cytosolic PLA2 (cPLA2), calcium-independent PLA2 (iPLA2), and platelet activating factor (PAF) acetyl hydrolase/oxidized lipid lipoprotein associated PLA2 ((Lp)PLA2). Specifically, PLA2s, in particular sPLA2s and cPLA2s, are known to hydrolyze phosphatidylcholines, which produce lysophosphatidylcholines and concurrently releases arachidonic acid.

The term "lysophosphatidylcholine" or "lyso PC" as used herein refers to a chemical compound derived from phosphatidylcholine, which is normally located in the cell membrane. Lyso PC can be generated from phosphatidylcholines (PC) either non-enzymatically through oxidation processes or enzymatically through conversion by phospholipases with PLA2 activity. Specifically, Lyso PC can be generated by cytosolic phospholipase A2 (PLA2G4A), cytosolic phospholipase A2 gamma (PLA2G4C) and/or group XV phospholipase A2 (PLA2G15). Lyso PCs can have different combinations of fatty acids of varying lengths and saturation attached at the C-1 (sn-1) position. Fatty acids containing 16, 18 and 20 carbons are the most common. 18:0 lyso PC, also called lyso SPC, in particular, consists of one chain of stearic acid at the C-1 position. 16:0 lyso PC, also called lyso PPC, in particular, consists of one chain of palmitic acid at the C-1 position.

The term "arachidonic acid" or "AA" as used herein refers to a polyunsaturated omega-6 fatty acid. Specifically, AA is present in phospholipids, especially phosphatidylcholine, of membranes of the body's cells. In addition to being involved in cellular signaling as a lipid second messenger involved in the regulation of signaling enzymes, arachidonic acid is a key inflammatory intermediate and can also act as a vasodilator. Specifically, AA is released into the cytosol from phosphatidylcholines upon hydrolysis of phosphatidylcholines into lysophosphatidylcholines by lipases with PLA2 activity.

AA is the precursor that is metabolized by various enzymes to a wide range of eicosanoids and metabolites of eicosanoids. Specifically, intracellular AA is further metabolized to eicosanoids by cyclooxygenases and lipoxygenases. For example, the enzymes cyclooxygenase-1 and -2 (COX-1 and COX-2) metabolize arachidonic acid to prostaglandin G2 and prostaglandin H2, 5-lipoxygenase metabolizes arachidonic acid to 5-hydroperoxyicosatetraenoic acid (5-HPETE), which in turn is metabolized to various leukotrienes, 15-lipoxygenase-1 (ALOX15) and 15-lipoxygenase-2 (ALOX15B) metabolize arachidonic acid to 15-hydroperoxyicosatetraenoic acid (15-HPETE) and 12-lipoxygenase (ALOX12) metabolizes arachidonic acid to 12-hydroperoxyeicosatetraenoic acid (12-HPETE).

Conversion of AA into eicosanoids or metabolites of eicosanoids is essential, because intracellular accumulation of AA has a toxic effect on cells. For example, AA released into the cytosol by phospholipase A2-activity can trigger apoptosis through the mitochondrial apoptotic pathway. As described herein, senescent cells have an increased AA formation rate, because PLA2 and lyso PC are upregulated. Therefore, inhibition of the metabolism of AA into eicosanoids increases AA levels, specifically intracellular AA levels, of senescent cells to a greater extent than in non-senescent cells, which leads to selective elimination of senescent cells. Specifically, senescent cells are selectively eliminated through cell death triggered by increased intracellular AA levels.

The term "selectively eliminating" refers to the exposure of the cells or subjects to a senolytic composition comprising at least one cyclooxygenase inhibitor and/or at least one lipoxygenase inhibitor and/or at least one inhibitor capable of inhibiting an enzyme with arachidonate-CoA ligase activity, which induces lysis of senescent cells. Senolytic compositions described herein are compositions that selectively eliminate senescent cells, preferably by killing senescent cells e.g. by inducing apoptosis. In other words, a senolytic composition destroys or kills a senescent cell in a biologically, clinically, and/or statistically significant manner compared with its capability to destroy or kill a non-senescent cell. Specifically, the senolytic composition described herein alters the lipid metabolism of senescent cells by targeting cyclooxygenases and lipoxygenases and enzymes with arachidonate-CoA ligase activity in a manner that induces (initiates, stimulates, triggers, activates, promotes) and results in (i.e., causes, leads to) death of the senescent cell. Additionally, the senolytic composition described herein may alter, for example, a cell survival signaling pathway (e.g., Akt pathway) or an inflammatory pathway, for example, by antagonizing a protein within the cell survival and/or inflammatory pathway in a senescent cell. Specifically, the composition described herein may selectively eliminate senescent cells by inducing (activating, stimulating, removing inhibition of) an apoptotic pathway that leads to cell death.

Non-senescent cells may be proliferating cells or may be quiescent cells. In certain instances, exposure of non-senescent cells to the composition described herein may temporarily reduce the capability of a non-senescent cell to proliferate, however, the non-senescent cell is not destroyed.

The term "cyclooxygenase inhibitor" or "COX inhibitor" as used herein refers to any compound able to bind to and inhibit, prevent or reduce cyclooxygenase activity or to selectively inhibit, prevent or reduce COX-1 or COX-2 activity, or any combination thereof. Specifically, COX inhibitor is any compound that is able to inhibit, prevent or reduce cyclooxygenase activity or to selectively inhibit, prevent or reduce COX-1 or COX-2 activity by at least 1, 1.5, 2, 2.5, 3, 3.5, 4, 4.5 or 5-fold or more. Even more specifically, a COX inhibitor is any compound that is able to significantly reduce cyclooxygenase activity, or to reduce COX-1 or COX-2 activity, at an $IC_{50}$ of less than 50 µM, preferably less than 45, 40, 35, 30, 25, 20, 15, or 10 µM or less than 9.5. 9, 8.5, 8, 7.5, 7, 6.5, 6, 5.5, 5, 4.5, 4, 3.5, 3, 2.5, 2, 1.5 or 1 µM, and even more preferably it is any compound able to significantly reduce cyclooxygenase activity at an $IC_{50}$ of less than 950, 900, 850, 800, 750, 700, 650, 600, 550, 500, 450, 400, 350, 300, 250, 200, 150, 100 nM, or less than 90, 80, 70, 60, 50, 40, 30, 20 or 10 nM or even less.

Specifically, the $IC_{50}$ of an inhibitor is determined by measuring the inhibition of recombinant human COX enzymes with commercially available cell-free test kits, such as the COX-1 (human) Inhibitor Screening Assay Kit (Cayman Chemicals, Cay701070-96) and the COX-2 (human) Inhibitor Screening Assay Kit (Cayman Chemicals, Cay701080-96), and calculating the resulting $IC_{50}$ value for the inhibitor. Alternatively, a human whole blood assay can be performed as described by (Brideau et al. 1996) to determine the COX1 and COX2 activities by measuring the production of TxB2 and PGE2, respectively.

Specifically, cyclooxygenase (COX), officially known as prostaglandin-endoperoxide synthase (PTGS), is an enzyme that is responsible for formation of prostanoids, including thromboxane and prostaglandins such as prostacyclin, from arachidonic acid. There are two isozymes of COX encoded by distinct gene products: a constitutive COX-1 and an inducible COX-2.

Classical COX inhibitors are not selective and inhibit all types of COX. The most frequent adverse effect is irritation of the gastric mucosa as prostaglandins normally have a protective role in the gastrointestinal tract. Newer COX inhibitors exhibit selectivity for COX-2 or for COX-1 or preferentially inhibit one of COX-2 or COX-1 over the other. Because COX-2 is usually specific to inflamed tissue, there is much less gastric irritation associated with COX-2 inhibitors, with a decreased risk of peptic ulceration.

Specifically, examples of non-selective COX inhibitors include acetylsalicylic acid or derivatives thereof such as NO-aspirin (nitro derivative of acetylsalicylic acid), and salicylic acid, or derivatives thereof such as magnesium salicylate, choline magnesium trisalicylate, trolamine salicylate, phenyl salicylate, glycol salicylate, menthyl salicylate, bismuth subsalicylate, and O-acetyl-L-serine, diclofenac and derivatives thereof such as e.g. diclofenac diethylamine, ibuprofen, suprofen, ketoprofen, fluriprofen, fluriprofen methyl ester, fenoprofen, carprofen, dexibuprofen, loxoprofen, zaltoprofen, pranoprofen, indomethacin, ketorolac, drugs of the oxicam class such as tenoxicam, piroxicam, lornoxicam, droxicam, and tolmetin, naproxen, diflunisal, salsalate, metamizole (dipyrone), oxaprozin, tiaprofenic acid, diethylcarbamazine, phenylbutazone, nepafenac (prodrug of amfenac), antrafenine, acemetacin, tolfenamic acid, dexketoprofen trometamol, talniflumate, propacetamol, bufexamac, chlorphenesin, clodronic acid, amfenac sodium monohydrate, ampiroxicam, salicin, fenbufen, xanthohumol, sulindac, dihomo-gamma-linolenic acid and flunixin meglumin.

Specifically, examples of selective COX-2 inhibitors include cyclosporine A, celecoxib, cimicoxib, lumiracoxib, rofecoxib, valdecoxib, parecoxib, firocoxib, etoricoxib, robenacoxib, deracoxib, acetaminophen (paracetamol), nabumetone, etodolac, bromfenac, icosapent, meloxicam, flufenamic acid, mefenamic acid, triflusal, niflumic acid, aceclofenac, specifically, as prodrug for diclofenac, Tacrolimus (also known as fujimycin or FK-506), lenalidomide, roscovitine (seliciclib), drospirenone, triamcinolone, pomalidomide, adapalene, thalidomide, asaraldehyde, dexamethasone, NS-398, rutaecarpine and nimesulide.

Specifically, examples of inhibitors selective for COX-1 or its isoform COX-3 include phenacetin, antipyrine, aminopyrine, SC-560 and mofezolac.

Specifically, many natural compounds also exhibit COX-inhibitory effects. Culinary mushrooms, like maitake, are able to partially inhibit COX-1 and COX-2, a variety of flavonoids have been found to inhibit COX-2, hyperforin has been shown to inhibit COX-1 around 3-18 times as much as aspirin, calcitriol (vitamin D) significantly inhibits the expression of the COX-2 gene and fish oils provide alternative fatty acids to arachidonic acid. These acids can be turned into some anti-inflammatory prostacyclins by COX instead of pro-inflammatory prostaglandins.

The term "lipoxygenase inhibitor" as used herein, refers to compounds that bind to and inhibit, prevent or decrease the activity of any lipoxygenase. Specifically, a lipoxygenase inhibitor is any compound that is able to inhibit, prevent or reduce lipoxygenase activity or that is able to selectively inhibit, prevent or reduce ALOXS activity, by at least 1, 1.5, 2, 2.5, 3, 3.5, 4, 4.5 or 5-fold or more. Even more specifically, a lipoxygenase inhibitor is any compound that is able to significantly reduce lipoxygenase activity, or that is able to selectively inhibit, prevent or reduce lipoxygenase activity, specifically ALOXS activity, at an $IC_{50}$ of less than 3 µM, preferably less than 2.5, 2, 1.5 or 1 µM, and even more preferably it is any compound able to significantly reduce lipoxygenase activity at an $IC_{50}$ of less than 950, 900, 850, 800, 750, 700, 650, 600, 550, 500, 450, 400, 350, 300, 250, 200, 150, 100 nM, or less than 90, 80, 70, 60, 50, 40, 30, 20 or 10 nM or even less.

Specifically, the IC50 of an inhibitor is determined by measuring the inhibition of recombinant human ALOX5 enzyme with commercially available cell-free test kits, such as the Human 5-Lipoxygenase Assay Kit (MYBioSource, MBS846911), and calculating the resulting $IC_{50}$ value for the inhibitor. Alternatively, a human blood LTB4 inhibition assay can be performed as described by (Hutchinson et al. 2009), which is also able to determine indirect inhibition of ALOX5 by ALOX5AP inhibitors.

Lipoxygenases are a family of iron-containing enzymes most of which catalyze the dioxygenation of polyunsaturated fatty acids in lipids containing a cis,cis-1,4-pentadiene into cell signaling agents. Specifically, the polyunsaturated fatty acid arachidonic acid serves as substrate for lipoxygenases. Specifically, arachidonate 5-lipoxygenase (or ALOX-5, or 5-LOX) is capable to metabolize and thereby transform arachidonic acid into eicosanoids, particularly 5-hydroxyeicosatetraenoic acid and 5-oxo-eicosatetraenoic acid. Leukotrienes, a family of eicosanoid inflammatory mediators, are produced by the oxidation of AA and the essential fatty acid eicosapentaenoic acid (EPA) by ALOX-5.

Arachidonate 5-Lipoxygenase Activating Protein (ALOX5AP or FLAP) is a protein which, with 5-lipoxygenase, is required for leukotriene synthesis. Leukotrienes are arachidonic acid metabolites, which have been implicated in various types of inflammatory responses. This protein localizes to the plasma membrane. Inhibitors of its function impede translocation of 5-lipoxygenase from the cytoplasm to the cell membrane and inhibit 5-lipoxygenase activation. An example of an ALOX5AP inhibitor is MK886. MK-886, or L-663536, is a leukotriene antagonist, which exerts its action by blocking the 5-lipoxygenase activating protein, thus inhibiting 5-lipoxygenase. Specifically, inhibitors of FLAP (or ALOX5AP) are lipoxygenase inhibitors, which inhibit the enzymatic activity of lipoxygenase indirectly.

Specifically, leukotriene formation is sex-biased. Leukotriene formation is under control of the hormone testosterone, which regulates the subcellular localization of ALOX-5, the key enzyme in the biosynthesis of pro-inflammatory eicosanoids. In individuals with increased testosterone levels, such as males, testosterone inhibits the translocation of ALOX-5 from the cytoplasm to the cell membrane, thus inhibiting its arachidonic acid metabolic activity.

According to a specific embodiment of the invention, the composition provided herein comprises a cyclooxygenase inhibitor and a lipoxygenase inhibitor, except for only those specific uses for which it comprises only one or more cyclooxygenase inhibitors. For example, one of such specific use for which the composition provided herein comprises only cyclooxygenase inhibitors is treatment of a sex-biased senescence-related disease or condition. Specifically, wherein the subject suffering from or at risk of developing a senescence related disease or condition is male, the composition for use in selectively eliminating senescent cells comprises at least one COX-1/COX2 inhibitor or a COX-1 inhibitor and a COX-2 inhibitor. However, treatment of male subjects with a composition comprising both, cyclooxygenase inhibitor and lipoxygenase inhibitor, is not excluded.

Examples of lipoxygenase and/or FLAP inhibitors include but are not limited to MK886, zileuton, masoprocol, diethylcarbamazine, azelastine, benoxaprofen, nordihydroguaiaretic acid, abietic acid, esculetin, montelukast, minocycline, MLN-977, rhein, diacerein, nabiximols, fostamatinib, AM103, DG031, fiboflapon, AA-861 and atreleuton.

According to a specific embodiment, the composition described herein comprises at least one dual cyclooxygenase/lipoxygenase inhibitor. Specifically, the composition for use in selectively eliminating senescent cells comprises such dual inhibitor when the subject is suffering from or is at risk of developing a senescence-related disease or condition is a female subject.

Exemplary dual inhibitors include but are not limited to licofelone, darbufelone, CI-987, S-2474, KME-4, Chebulagic acid, balsalazide, mesalazine, sulfasalazine, aminosalicylic acid, meclofenamic acid, morniflumate diarylpyrazole derivatives, thieno[2,3-b]pyridine derivatives, N-substituted 5-aminosalicylicylamides, flavocoxid, indolizine derivatives, LQFM-091, hyperforin, celastrol, BW755C, tepoxalin, b-boswellic acid, D-002 (a mixture of six higher aliphatic beeswax alcohols), 2,3-diarylxanthones, phenidone and ER-34122.

As referred to herein, an enzyme with arachidonate-CoA ligase activity is an enzyme capable of catalyzing the conversion of arachidonic acid and CoA into arachidonyl-CoA. Specific examples of such enzymes are long-chain-fatty-acid-CoA ligases (ACSL), specifically ACSL4.

As used herein, the term "long-chain-fatty-acid-CoA ligase inhibitor", or "ACSL inhibitor" in short, refers to compounds that bind to and inhibit, prevent or decrease the activity of any long-chain-fatty-acid-CoA ligase. Specifically, an ACSL inhibitor is any compound that is able to inhibit, prevent or reduce ACSL activity by at least 1, 1.5, 2, 2.5, 3, 3.5, 4, 4.5 or 5-fold or more. Even more specifically, an ACSL inhibitor is any compound that is able to significantly reduce ACSL activity at an IC50 of about 100 µM or less, preferably less than 50, 45, 40, 35, 30, 25 or 20 µM or less, and even more preferably it is any compound able to significantly reduce arachidonate-CoA ligase activity at an $IC_{50}$ of about 19, 18, 17, 16, 15, 14, 13, 12, 11, 10 or 9 µM. Specifically, the $IC_{50}$ of an ACSL inhibitor is determined by measuring the inhibition of acyl-CoA formation by incubating either recombinant ACSL enzymes or cell lysates with ATP, CoA and radioactively labeled fatty acids, such as arachidonic acid, as described by (Askari et al. 2007; Kim et al. 2001).

Incorporation of free intracellular arachidonic acid into phospholipids requires thioesterification of AA by enzymes belonging to the group of long-chain acyl-CoA synthetases.

Long-chain-fatty acyl CoA synthetase, also referred to as long-chain-fatty-acid-CoA ligase, in short "ACSL", is an enzyme of the ligase family that activates oxidation of complex fatty acids. These enzymes produce acyl-CoAs from fatty acids that are at least 12 carbons in length. ACSL catalyzes the formation of fatty acyl-CoA by a two-step process proceeding through an adenylated intermediate, specifically, it catalyzes the activation of a long fatty acid chain to fatty acyl Coenzyme A (fatty acid CoA). There are several highly conserved areas and a 20-30% amino acid sequence similarity between the members of this superfamily. Specifically, the enzymes in the family consist of a large N-terminal and a small C-terminal domain, with the catalytic site positioned between the two domains.

Specifically, the term "ACSL" as used herein also refers to isozymes of the long-chain fatty-acid coenzyme A ligase family. There are five ACSL isoforms known in humans and rodents: ACSL1, ACSL3, ACSL4, ACSL5, and ACSL6. Although differing in substrate specificity, subcellular localization, and tissue distribution, all isozymes of this family convert free long-chain fatty acids into fatty acyl-CoA esters, and thereby play a key role in lipid biosynthesis and fatty acid degradation.

Specifically, ACSL4 and ACSL1 are two members of the acyl-CoA synthetase family, which are required for the activation of free fatty acids with CoA, generating acyl-CoA, the precursor for the re-integration and degradation processes in the Lands cycle (Murphy and Folco 2019). The Lands cycle encompasses the enzymatic hydrolysis of phospholipids, generating lysophospholipids and free fatty acids, such as AA, the activation of free fatty acids through acyl-CoA synthetases and the re-integration of acyl-CoA into lysophospholipids by acyl-CoA transferases. Alternatively, arachidonate-CoA can be degraded via β-oxidation or used by diacylglycerol O-acyltransferases to form diacyl- and triacylglycerols and by sterol O-acyltransferases to form cholesterol esters.

Specifically, ACSL4 preferentially utilizes arachidonate as substrate. ACSL4 controls the intracellular level of arachidonic acid, because AA can induce apoptosis, specifically in senescent cells, thus ACSL4 has the ability to modulate apoptosis. Overexpression of ACSL4 has been shown to result in a higher rate of arachidonoyl-CoA synthesis, increased AA incorporation into phosphatidylethanolamine, phosphatidylinositol, and triacylglycerol, and reduced cellular levels of unesterified AA.

According to a specific embodiment, the composition described herein comprises an ACSL inhibitor as active agent. According to a further specific embodiment, the composition described herein comprises an ACSL inhibitor and at least one inhibitor capable of inhibiting one or more of COX-1, COX-2 or lipoxygenase. Specifically, the composition described herein comprises an inhibitor capable of inhibiting at least two of ACSL, COX-1, COX-2 and lipoxygenase.

According to a specific embodiment, the ACSL inhibitor is selected from the group consisting of triacsin A, triacsin B, triacsin C, triacsin D, analogs of triacsin C (Kim et al. 2012; Prior et al. 2014), N-ethylmaleimide, 2-fluoropalmitic acid, troglitazone, ciglitazone, pioglitazone and rosiglitazone.

According to a specific embodiment, the composition described herein comprises at least one cyclooxygenase and at least one lipoxygenase inhibitor and an additional compound capable of inhibiting intracellular conversion of arachidonic acid. Specifically, such additional compound is any one or more or all of a natural compound, an inhibitor of cytochrome P450, an inhibitor of long-chain-fatty-acid CoA ligase 4 (ACSL4), an inhibitor of a lysophosphatidylcholine acyltransferase and/or an inhibitor of fatty acid elongase.

Specifically, an inhibitor of cytochrome P450 can be an inhibitor of any one or more or all of cytochrome P450 2J2 (CYP2J2), cytochrome P450 2C (CYP2C), cytochrome P450 4A (CYP4A) and/or cytochrome P450 4F (CYP4F).

Specifically, an inhibitor of lysophosphatidylcholine acyltransferase (LPCAT) can be an inhibitor of any one or more or all of LPCAT1, LPCAT2, LPCAT3, LPCAT4, lysophospholipid acyltransferase 2 (MBOAT2) and Membrane Bound O-Acyltransferase Domain Containing 7 (lysophospholipid acyltransferase 7 and/or MBOAT7).

Specifically, an inhibitor of fatty acid elongase can be an inhibitor of any one or more or all of Elongation of very long chain fatty acids protein 2 (ELOVL2), Elongation of very long chain fatty acids protein 4 (ELOVL4) and/or Elongation of very long chain fatty acids protein 5 (ELOVL5).

According to a specific embodiment, the composition described herein comprises at least one cyclooxygenase and at least one lipoxygenase inhibitor and an additional compound capable of manipulating ATP levels, specifically increasing and/or decreasing intracellular ATP levels. Specifically, such additional compound is any one or more or all of an inhibitor of ATP synthase, an inhibitor or ADP/ATP translocases and/or an inhibitor of glycolysis.

As described herein, the compositions provided herein can be used for the treatment of a senescence-related disease or condition. Specifically, the compositions provided herein are used for the prevention (i.e. reduction of the likelihood of occurrence) or delay of the onset of a senescence-related disease or condition, for the prevention or delay of the progression of a senescence-related disease or condition or to promote the regression of a senescence-related disease or condition.

The term "senescence-related disease or disorder" refers to conditions, diseases or disorders related to, associated with, or caused by cellular senescence, including age-related diseases and disorders.

The senescence-related disease or condition can be a cardiovascular disease or condition, including but not limited to angina, arrhythmia, atherosclerosis, cardiomyopathy, congestive heart failure, coronary artery disease (CAD), carotid artery disease, endocarditis, coronary thrombosis, carotid thrombosis, myocardial infarction (MI), high blood pressure/hypertension, aortic aneurysm, brain aneurysm, cardiac fibrosis, cardiac diastolic dysfunction, hypercholesterolemia/hyperlipidemia, mitral valve prolapse, peripheral vascular disease, peripheral artery disease (PAD), cardiac stress resistance, and stroke.

Subjects suffering from cardiovascular disease can be identified using standard diagnostic methods known in the art for cardiovascular disease. Generally, diagnosis of atherosclerosis and other cardiovascular disease is based on symptoms (e.g., chest pain or pressure (angina), numbness or weakness in arms or legs, difficulty speaking or slurred speech, drooping muscles in face, leg pain, high blood pressure, kidney failure and/or erectile dysfunction), medical history, and/or physical examination of a patient. Subjects at risk of developing cardiovascular disease include those having a family history of cardiovascular disease and those having other risk factors such as high blood pressure, high cholesterol, diabetes, obesity and/or smoking. In a certain embodiment, the cardiovascular disease that is a senescence cell associated disease/disorder is atherosclerosis. Atherosclerosis is characterized by patchy intimal plaques (atheromas) that encroach on the lumen of medium-sized and large arteries; the plaques contain lipids, inflammatory cells, smooth muscle cells, and connective tissue.

The effectiveness of a composition described herein for treating or preventing (i.e., reducing or decreasing the likelihood of developing or occurrence of) a cardiovascular disease (e.g., atherosclerosis) can readily be determined by a person skilled in the medical and clinical arts. One or any combination of diagnostic methods, including physical examination, assessment and monitoring of clinical symptoms, and performance of analytical tests and methods described herein and practiced in the art (e.g., angiography, electrocardiography, stress test, non-stress test), may be used for monitoring the health status of the subject. The effects of the treatment of a senolytic combination can be analyzed using techniques known in the art, such as comparing symptoms of patients suffering from or being at risk of cardiovascular disease that have received the treatment with those of patients without such a treatment or with placebo treatment.

The senescence-related disease or condition can be a neurological condition. Neurological conditions include, but are not limited to, Parkinson's disease, Alzheimer's disease, dementia, amyotrophic lateral sclerosis (ALS), bulbar palsy, pseudobulbar palsy, primary lateral sclerosis, motor neuron dysfunction (MND), mild cognitive impairment (MCI), Huntington's disease, ocular diseases, macular degeneration (wet and dry), glaucoma, vision loss, presbyopia, cataracts, progressive muscular atrophy, lower motor neuron disease, spinal muscular atrophy (SMA), Werdnig-Hoffman Disease (SMA1), SMA2, Kugelberg-Welander Disease (SM3), Kennedy's disease, post-polio syndrome, hereditary spastic paraplegia, age-related memory decline, and depression and mood disorders. The effects of the senolytic composition described herein for use in the treatment or prophylaxis of a neurological condition can be analyzed by comparing symptoms of patients suffering from or being at risk of a neurological disease or disorder, such as e.g. Parkinson's disease or Alzheimer's disease, who have received the treatment with those of patients without such a treatment or with placebo treatment.

Parkinson's disease is the second most common neuro degenerative disease. It is a disabling condition of the brain characterized by slowness of movement (bradykinesia), shaking, stiffness, and in the later stages, loss of balance. Many of these symptoms are due to the loss of certain nerves in the brain, which results in the lack of dopamine. This disease is characterized by neuro degeneration, such as the loss of about 50% to 70% of the dopaminergic neurons in the substantia nigra pars compacta, a profound loss of dopamine in the striatum, and/or the presence of intracytoplasmic inclusions (Lewy bodies), which are composed mainly of alpha-synuclein and ubiquitin. Parkinson's disease also features locomotor deficits, such as tremor, rigidity, bradykinesia, and/or postural instability. These motor manifestations can also be accompanied by non-motor symptoms such as olfactory deficits, sleep impairment, and neuropsychiatric disorders. Generally, diagnosis of Parkinson's disease is based on symptoms, medical history, and neurological and/or physical examination of a patient. Subjects at risk of developing Parkinson's disease include those having a family history of Parkinson's disease and those exposed to pesticides (e.g., rotenone or paraquat), herbicides (e.g., agent orange), or heavy metals. Methods for detecting, monitoring or quantifying neuro degenerative deficiencies and/or locomotor deficits associated with Parkinson's diseases are known in the art, such as histological studies, biochemical studies, and behavioral assessment.

Alzheimer's disease (AD) is a neurodegenerative disease that shows a slowly progressive mental deterioration with failure of memory, disorientation, and confusion, leading to profound dementia. Age is the single greatest predisposing risk factor for developing AD, which is the leading cause of dementia in the elderly. Early clinical symptoms show remarkable similarity to mild cognitive impairment, which is characterized by difficulty in remembering recent life experiences or people's names. As the disease progresses, impaired judgment, confusion, behavioral changes, disorientation, and difficulty in walking and swallowing occur. Alzheimer's disease is characterized by the presence of neurofibrillary tangles and amyloid (senile) plaques in histological specimens. The disease predominantly involves the limbic and cortical regions of the brain. A number of behavioral and histopathological assays are known in the art for evaluating Alzheimer's disease phenotype, for characterizing therapeutic agents, and assessing treatment. Subjects suffering from Alzheimer's disease can be identified using standard diagnostic methods known in the art for Alzheimer's disease. Generally, diagnosis of Alzheimer's disease is based on symptoms (e.g., progressive decline in memory function, gradual retreat from and frustration with normal activities, apathy, agitation or irritability, aggression, anxiety, sleep disturbance, dysphoria, aberrant motor behavior, disinhibition, social withdrawal, decreased appetite, hallucinations, dementia), medical history, neuropsychological tests, neurological and/or physical examination of a patient. Cerebrospinal fluid may also be for tested for various proteins that have been associated with Alzheimer pathology, including tau, amyloid beta peptide, and AD7C-

NTP. Genetic testing is also available for early-onset familial Alzheimer disease (eFAD), an autosomal-dominant genetic disease. Clinical genetic testing is available for individuals with AD symptoms or at-risk family members of patients with early-onset disease. In the U.S., mutations for PS2, and APP may be tested in a clinical or federally approved laboratory under the Clinical Laboratory Improvement Amendments. A commercial test for PS 1 mutations is also available (Elan Pharmaceuticals).

MCI is a brain-function syndrome involving the onset and evolution of cognitive impairments beyond those expected based on age and education of the individual, but which are not significant enough to interfere with this individual's daily activities. MCI is an aspect of cognitive aging that is considered to be a transitional state between normal aging and the dementia into which it may convert. MCI that primarily affects memory is known as "amnestic MCI". A person with amnestic MCI may start to forget important information that he or she would previously have recalled easily, such as recent events. Amnestic MCI is frequently seen as prodromal stage of Alzheimer's disease.

MND is a group of progressive neurological disorders that destroy motor neurons, the cells that control essential voluntary muscle activity such as speaking, walking, breathing and swallowing. It is classified according to whether degeneration affects upper motor neurons, lower motor neurons, or both. Examples of MNDs include, e.g. Lateral Sclerosis (ALS), bulbar palsy, and spinal muscular atrophy (SMA). It can affect the arms, legs, or facial muscles. Patients with an MND show one or more motor deficits, including muscle weakness and wasting, uncontrollable twitching, spasticity, slow and effortful movements, and overactive tendon reflexes. Primary lateral sclerosis is a disease of the upper motor neurons, while progressive muscular atrophy affects only lower motor neurons in the spinal cord. In progressive bulbar palsy, the lowest motor neurons of the brain stem are most affected, causing slurred speech and difficulty chewing and swallowing. There are almost always mildly abnormal signs in the arms and legs. Methods for detecting, monitoring, quantifying or assessing motor deficits and histopathological deficiencies associated with MND are known in the art, including histopathological, biochemical, and electrophysiological studies and motor activity analysis.

The senescence-related disease or condition can be an inflammatory condition. Inflammatory conditions include, but are not limited to, musculoskeletal diseases, osteoarthritis, osteoporosis, sarcopenia, lupus, interstitial cystitis, scleroderma, alopecia, oral mucositis, rheumatoid arthritis, inflammatory bowel disease, kyphosis, herniated intervertebral disc, ulcerative colitis, Crohn's disease, ulcerative asthma, renal fibrosis including post-transplant renal fibrosis, liver fibrosis, pancreatic fibrosis, cardiac fibrosis, skin wound healing including diabetes related wound healing, and oral submucosa fibrosis. The effects of the senolytic composition described herein for use in the treatment or prophylaxis of an inflammatory condition can be analyzed by comparing symptoms of patients suffering from or being at risk of an inflammatory disease or disorder, such as e.g. osteoarthritis, who have received the treatment with those of patients without such a treatment or with placebo treatment.

Osteoarthritis is a degenerative joint disease that is characterized by fibrillation of the cartilage at sites of high mechanical stress, bone sclerosis, and thickening of the synovium and the joint capsule. Symptoms of osteoarthritis include sore or stiff joints, particularly the hips, knees, and lower back, after inactivity or overuse; stiffness after resting that goes away after movement; and pain that is worse after activity or toward the end of the day. The effectiveness the composition described herein for treatment or prophylaxis of osteoporosis and monitoring of a subject who receives the composition can readily be determined by a person skilled in the medical and clinical arts. One or any combination of diagnostic methods, including physical examination (such as determining tenderness, swelling or redness of the affected joint), assessment and monitoring of clinical symptoms (such as pain, stiffness, mobility), and performance of analytical tests and methods described herein and practiced in the art (e.g., determining the level of inflammatory cytokines or chemokines; X-ray images to determine loss of cartilage as shown by a narrowing of space between the bones in a joint; magnetic resonance imaging (MRI), providing detailed images of bone and soft tissues, including cartilage), may be used for monitoring the health status of the subject.

Osteoporosis is a progressive bone disease that is characterized by a decrease in bone mass and density that may lead to an increased risk of fracture. Bone mineral density (BMD) is reduced, bone microarchitecture deteriorates, and the amount and variety of proteins in bone are altered. Osteoporosis is typically diagnosed and monitored by a bone mineral density test. Post-menopausal women or women who have reduced estrogen are most at risk. While both men and women over 75 are at risk, women are twice as likely to develop osteoporosis than men.

Further inflammatory/autoimmune disorders that may be treated with the composition described herein includes irritable bowel syndrome (IBS) and inflammatory bowel diseases, such as ulcerative colitis and Crohn's disease. Inflammatory bowel disease (IBD) involves chronic inflammation of all or part of the digestive tract. In addition to life-threatening complications arising from IBD, the disease can be painful and debilitating. Ulcerative colitis is an inflammatory bowel disease that causes long-lasting inflammation in part of the digestive tract. Symptoms usually develop over time, rather than suddenly. Ulcerative colitis usually affects only the innermost lining of the large intestine (colon) and rectum. Crohn's disease is an inflammatory bowel disease that causes inflammation anywhere along the lining of the digestive tract, and often extends deep into affected tissues. This can lead to abdominal pain, severe diarrhea, and malnutrition. The inflammation caused by Crohn's disease can involve different areas of the digestive tract. Diagnosis and monitoring of the diseases is performed according to methods and diagnostic tests routinely practiced in the art, including blood tests, colonoscopy, flexible sigmoidoscopy, barium enema, CT scan, MRI, endoscopy, and small intestine imaging.

The senescence-related disease or condition can be a dermatological condition. Dermatological conditions include, but are not limited to, psoriasis, eczema, rhytides, pruritis, dysesthesia, papulosquamous disorders, erythroderma, lichen planus, lichenoid dermatosis, atopic dermatitis, eczematous eruptions, eosinophilic dermatosis, rashes, photosensitivity and photoaging related diseases and disorders, reactive neutrophilic dermatosis, pemphigus, pemphigoid, immunobullous dermatosis, fibrohistocytic proliferations of skin, skin nevi, urticaria, hyperpigmentation, cutaneous lymphomas, psoriasis, and cutaneous lupus. In certain embodiments, the senescent cell associated disorder is an inflammatory disorder of the skin, such as by way of a non-limiting examples, psoriasis and eczema that may be treated or prevented using the composition described herein. Psoriasis is characterized by abnormally excessive and rapid growth of the epidermal layer of the skin. A diagnosis of psoriasis is usually based on the appearance of the skin. Skin characteristics typical for psoriasis are scaly red plaques, papules, or patches of skin that may be painful and itch.

Other immune disorders or conditions that may be treated with the senolytic composition described herein include conditions resulting from a host immune response to an organ transplant (e.g., kidney, bone marrow, liver, lung, or heart transplant), such as rejection of the transplanted organ. Specifically, the senolytic composition may be used for treating or reducing the likelihood of occurrence of graft-vs-host disease.

The senescence-related disease or condition can be a metabolic disorder. Metabolic disorders include, but are not limited to type I and type II diabetes mellitus, diabetic ulcers and obesity. The effects of the senolytic composition described herein for use in the treatment or prophylaxis of metabolic condition can be analyzed by comparing symptoms of patients suffering from or being at risk of a metabolic disease or disorder, such as e.g. diabetes, who have received the treatment with those of patients without such a treatment or with placebo treatment.

Diabetes is characterized by high levels of blood glucose caused by defects in insulin production, insulin action, or both. The great majority (90 to 95%) of all diagnosed cases of diabetes in adults are type 2 diabetes, characterized by the gradual loss of insulin production by the pancreas. Subjects suffering from type 2 diabetes can be identified using standard diagnostic methods known in the art for type 2 diabetes. Generally, diagnosis of type 2 diabetes is based on symptoms (e.g., increased thirst and frequent urination, increased hunger, weight loss, fatigue, blurred vision, slow-healing sores or frequent infections, and/or areas of darkened skin), medical history, and/or physical examination of a patient. Subjects at risk of developing type 2 diabetes include those who have a family history of type 2 diabetes and those who have other risk factors such as excess weight, fat distribution, inactivity, race, age, prediabetes, and/or gestational diabetes.

Obesity and obesity-related are used to refer to conditions of subjects who have a body mass that is measurably greater than ideal for their height and frame. Body Mass Index (BMI) is a measurement tool used to determine excess body weight, and is calculated from the height and weight of a subject. A human is considered overweight when the person has a BMI of 25-29; a person is considered obese when the person has a BMI of 30-39, and a person is considered severely obese when the person has a BMI of 40 or higher.

A condition or disorder associated with diabetes and senescence is a diabetic ulcer (i.e., diabetic wound). An ulcer is a breakdown in the skin, which may extend to involve the subcutaneous tissue or even muscle or bone. These lesions occur, particularly, on the lower extremities. Patients with diabetic venous ulcer exhibit elevated presence of cellular senescence at sites of chronic wounds.

The senescence-related disease or condition can be a macular degeneration, dry (non-neovascular) or wet (neo-vascular) macular degeneration. Macular degeneration is a neurodegenerative disease that causes the loss of photoreceptor cells in the central part of retina, called the macula. Macular degeneration generally is classified into two types: dry type and wet type. The dry form is more common than the wet, with about 90% of age-related macular degeneration (ARMD) patients diagnosed with the dry form. The wet form of the disease usually leads to more serious vision loss. Symptoms include perceived distortion of straight lines and, in some cases, the center of vision appears more distorted than the rest of a scene; a dark, blurry area or "white-out"

appears in the center of vision; and/or color perception changes or diminishes. Diagnosing and monitoring of a subject with macular degeneration may be accomplished by a person skilled in the ophthalmic art according to art-accepted periodic eye examination procedures and report of symptoms by the subject.

The senescent cell-associated condition can be a pulmonary condition. Pulmonary conditions include, but are not limited to, idiopathic pulmonary fibrosis (TPF), chronic obstructive pulmonary disease (COPD), asthma, cystic fibrosis, bronchiectasis, emphysema, age-related loss of pulmonary function, and age-associated sleep apnea. The effects of the senolytic composition described herein for use in the treatment or prophylaxis of pulmonary condition can be analyzed by comparing symptoms of patients suffering from or at risk of a pulmonary disease or disorder, such as e.g. COPD, who have received the treatment with those of patients without such a treatment or with placebo treatment.

COPD is a lung disease defined by persistently poor airflow resulting from the breakdown of lung tissue (emphysema) and the dysfunction of the small airways (obstructive bronchiolitis). Primary symptoms of COPD include shortness of breath, wheezing, chest tightness, chronic cough, and excess sputum production. COPD is most commonly caused by tobacco smoke (including cigarette smoke, cigar smoke, secondhand smoke, pipe smoke), occupational exposure (e.g., exposure to dust, smoke or fumes), and pollution, occurring over decades thereby implicating aging as a risk factor for developing COPD.

Pulmonary fibrosis is a chronic and progressive lung disease characterized by stiffening and scarring of the lung, which may lead to respiratory failure, lung cancer, and heart failure. Fibrosis is associated with repair of epithelium. Subjects at risk of developing pulmonary fibrosis include those exposed to environmental or occupational pollutants, such as asbestosis and silicosis; who smoke cigarettes; having some typical connective tissue diseases such as rheumatoid arthritis, SLE and scleroderma; having other diseases that involve connective tissue, such as sarcoidosis and Wegener's granulomatosis; having infections; taking certain medications (e.g., amiodarone, bleomycin, busufan, methotrexate, and nitrofurantoin); those subject to radiation therapy to the chest; and those whose family member has pulmonary fibrosis. Symptoms of pulmonary fibrosis are known in the art and include shortness of breath, particularly during exercise; dry, hacking cough; fast, shallow breathing; gradual unintended weight loss; tiredness; aching joints and muscles; and clubbing (widening and rounding of the tips of the fingers or toes).

According to a further specific embodiment, the composition provided herein is used to improve the performance of transplants. Specifically, presence of an increased number of senescent cells in the donor organ and/or in the recipient negatively influences the performance of a transplant. According to a specific embodiment, the composition described herein is used to selectively eliminate senescent cells in the donor organ and/or the recipient to improve the performance of the transplant.

According to a further specific embodiment, the composition provided herein is used to prevent or attenuate senescence-associated scar formation and fibrosis.

According to a further specific embodiment, the composition provided herein is used to ameliorate side effects of chemotherapy. According to yet a further specific embodiment, the composition provided herein is used to prevent or delay tumor relapse and the occurrence of senescence-related diseases and conditions. Therapy-induced senescence (TIS) is a common side effect of cancer therapy and causes premature aging in patients surviving the therapy. In addition, TIS induces senescence-associated stemness (SAS) in tumors, for example in Bcl2 lymphomas, thereby causing an increased tumor-initiation capacity and an increased risk for cancer relapse.

Removal or destruction of senescent cells may ameliorate acute toxicity, including acute toxicity comprising energy imbalance, of a chemotherapy or radiotherapy. Acute toxic side effects include but are not limited to gastrointestinal toxicity (e.g., nausea, vomiting, constipation, anorexia, diarrhea), peripheral neuropathy, fatigue, malaise, low physical activity, hematological toxicity (e.g., anemia), hepatotoxicity, alopecia (hair loss), pain, infection, mucositis, fluid retention, dermatological toxicity (e.g., rashes, dermatitis, hyperpigmentation, urticaria, photosensitivity, nail changes), mouth, gum or throat problems, or any toxic side effect caused by a chemotherapy or radiotherapy. For example, toxic side effects caused by radiotherapy or chemotherapy (see, e.g., National Cancer Institute website) may be ameliorated by the methods described herein. Accordingly, in certain embodiments, methods are provided herein for ameliorating (reducing, inhibiting, or preventing occurrence (i.e., reducing the likelihood of occurrence)) acute toxicity or reducing severity of a toxic side effect (i.e., deleterious side effect) of a chemotherapy or radiotherapy or both in a subject who receives the therapy, wherein the method comprises administering to the subject the composition as described herein that selectively kills, removes, or destroys or facilitates selective destruction of senescent cells. Administration of a senolytic composition for treating or reducing the likelihood of occurrence, or reducing the severity of a chemotherapy or radiotherapy side effect may be accomplished by the same treatment courses described above for treatment/prevention of metastasis. As described for treating or preventing (i.e., reducing the likelihood of occurrence of) metastasis, the senolytic combination is administered during the off-chemotherapy or off-radiotherapy time interval or after the chemotherapy or radiotherapy treatment regimen has been completed.

Further provided herein is a method of identifying senescent cells in a subject. Specifically, altered levels of members of the altered lipid metabolism of senescent cells described herein can be detected to identify senescent cells in a subject. Specifically, the method of identifying senescent cells in a subject comprises determining the level of at least one of the biomarkers lysophosphatidylcholine, arachidonic acid and phospholipase A2 activity. Preferably, the biomarker is lyso SPC or lyso PPC or arachidonic acid.

The method of identifying senescent cells in a subject can be specifically used for determining the presence of senescent cells in context of diagnosing senescence-related diseases or conditions, diagnosing the risk of senescence-related diseases or conditions in a subject, monitoring senescence-related diseases or conditions or monitoring or predicting treatment-response, or monitoring exposure to senescence inducing agents (intoxicants, including oxidative stressors, DNA damaging agents, etc.).

A "control", "control sample", or "reference value" or "reference level" are terms which can be used interchangeably herein, and are to be understood as a sample or standard used for comparison with the experimental sample. The control may include a sample obtained from a healthy subject or a subject, which is not at risk of or suffering from senescence or is not exposed to stress conditions inducing senescence or which is exposed to treatment with a senolytic. Reference level specifically refers to the level of lysophosphatidylcholine, arachidonic acid and/or PLA2 activity quantified in a sample from a healthy subject, from a subject, which is not at risk of or suffering from senescence or is not exposed to stress conditions inducing senescence or, in case of senolytic treatment monitoring, said level could also be derived from a sample of a subject before starting senolytic treatment or during the course of senolytic treatment.

Specifically, levels of lysophosphatidylcholine, arachidonic acid and/or PLA2 activity are measured using immunoassays such as ELISA, mass spectrometry or high-performance liquid chromatography (HPLC).

For example, the level, specifically intracellular level, of lysophosphatidylcholines can be measured by high performance liquid chromatography coupled to tandem mass spectrometry in the positive ion mode as described by Gruber et al. 2015 or by HPLC as described by Jeschek et al. 2016.

For example, the level of intracellular arachidonic acid can be measured by an enzyme linked immunosorbent assay, such as for example the universal arachidonic acid ELISA Kit supplied by Novus Biologicals (NBP2-66372) or any other equivalent ELISA assay. According to further specific examples, the level of arachidonic assay can be measured by flow-injection electrospray ionization mass spectrometry as described by Gruber et al. 2015, with high performance liquid chromatography as described by Nishikiori et al. 2015 or with high performance liquid chromatography coupled to tandem mass spectrometry in the negative ion mode.

For example, PLA2 activity can be measured by an assay that comprises a PLA2 substrate that on cleavage by the phospholipase A2 activity yields a fluorescent product that can be quantified with a fluorimeter, e.g. bis-BODIPY®-FL-C11-PC (Thermo Fisher), or with the EnzChek™ Phospholipase A2 Assay Kit (Thermo Fisher) or any other equivalent assay.

According to a specific embodiment, an increase by more than two or three standard deviations of the level of at least one of the biomarkers lysophosphatidylcholine, arachidonic acid or phospholipase A2 compared to the level of said biomarkers in a reference is indicative of the presence of senescent cells or cellular senescence.

Specifically, a more than 2.0, 2.5, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9 or 5.0 fold increase between the reference level of any one or more of said biomarkers obtained from a healthy subject or a group of healthy subjects compared to the level of one or more of said biomarkers obtained from a sample of a subject is indicative of the presence of senescent cells in said sample.

Specifically a more than 2.0, 2.5, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9 or 5.0 fold decrease between the reference level of any one or more of said biomarkers obtained from a sample of a subject during or after senolytic treatment compared with a sample of the same subject from an earlier timepoint (intra-individual comparison or intra-individual difference) is indicative of positive response to senolytic treatment.

Additionally, a control may also be a standard reference value or range of values. The reference level can also be determined as the average level of any one or more of lysophosphatidylcholine, arachidonic acid and phospholipase A2 activity in a sample of a healthy subject and/or in a subject prior to a pharmacologic, dietary or life-style intervention. As an alternative, also a pool of samples from one or more subjects may be used or a reference disclosed in literature.

The method for the detection of senescent cells as described herein specifically provides a diagnostic and predictive tool using a diagnostic signature or expression pattern as described herein, comprised of an increase in the level of any one or more or all of lysophosphatidylcholine, arachidonic acid and/or phospholipase A2, applicable over a broad range of senescence of various cell types including but not limited to fibroblasts, endothelial cells, kidney epithelial cells, liver cells, neuronal cells, skin cells, lung epithelial cells, or colon epithelial cells. In particular, detection of senescent cells in the tissue, blood or serum of young subjects or subjects not being exposed to senescence inducing stress conditions and old subjects or subjects being exposed to senescence inducing stress conditions provides a diagnostic and predictive tool that has a higher significance for early diagnosis, long-term prognosis, and screening of patients with cellular senescence. The method as described herein also provides a diagnostic tool for monitoring treatment with senolytics.

Specifically, the method of identifying senescent cells as described herein can be performed as single measurement but may also be performed by repetitive determinations.

Specifically, use of the method for detecting senescent cells as described herein also encompasses predicting transplant organ function or predicting organ transplant failure.

According to a specific embodiment, the herein described method can also be used for detecting a decline of senescent cells or reduction of cellular senescence, wherein the level of at least one of the biomarkers lysophosphatidylcholine, arachidonic acid and/or PLA2 activity is compared with the level of the corresponding lysophosphatidylcholine, arachidonic acid and/or PLA2 activity prior to a treatment with senolytics, anti-aging agents or any anti-aging intervention. Specifically, a decrease in the level of at least one of said biomarkers can indicate the removal of senescent cells e.g. during use of senolytics, anti-aging agents (e.g. rapamycin, spermidine, metformin), or any other anti-aging intervention like diet, exercise, etc. This signature can also be used to identify subjects that would benefit from any senolytic intervention.

Specifically, the method is useful for monitoring a subject, specifically for measuring the response of a subject to senolytic treatments. Therefore, the biomarkers may be also used for indication of efficient drug doses (dose finding, e.g. during development of any type of intervention, or in terms of identifying personalized treatment options or dosing).

Further provided herein is a method of screening for senolytic compounds, which are capable of selectively eliminating senescent cells. According to a specific embodiment, the level of arachidonic acid is measured in senescent cells upon exposure to a compound, using for example enzyme-based immunoassays such as ELISA, and compared to the level of arachidonic acid in a non-senescent cell also exposed to the compound or to a senescent cell not exposed to the compound or both. Specifically, compounds identified by this screening method are capable of selectively eliminating senescent cells.

The present invention further comprises the following items:

1. A composition comprising one or more inhibitors capable of inhibiting at least two of cyclooxygenase-1 (COX-1), cyclooxygenase-2 (COX-2) and lipoxygenase, for use in selectively eliminating senescent cells.

2. A composition comprising one or more inhibitors capable of inhibiting an enzyme with arachidonate-CoA ligase activity, specifically long-chain-fatty-acid- CoA ligase (ACSL) 1, ACSL3, ACSL4, ACSL5, ACSL6, SLC27A2 or ACSBG2 for use in selectively eliminating senescent cells.

3. The composition for use according to item 2, comprising one or more inhibitors capable of inhibiting an enzyme with arachidonate-CoA ligase activity, specifically long-chain-fatty-acid-CoA ligase (ACSL) 1, ACSL3, ACSL4, ACSL5, ACSL6, SLC27A2 or ACSBG2, and at least one of COX-1, COX-2 or lipoxygenase.

4. The composition for use according to any one of items 1 to 3, wherein the senescent cells are characterized by increased intracellular levels of at least one of lysophosphatidylcholine, arachidonic acid and phospholipase A2 activity.

5. The composition for use according to item 4, wherein the lysophosphatidylcholine is 1-steraroyl-2-hydroxy-sn-glycero-3-phosphocholine (LysoSPC) or 1-palmitoyl-2-hydroxy-sn-glycero-3-phosphocholine (LysoPPC).

6. The composition for use according to any one of items 1 to 5, wherein one or more of the inhibitors are COX-1 and/or COX-2 inhibitors, selected from the group consisting of acetylsalicylic acid, diclofenac, celecoxib, cyclosporine A, ibuprofen, acetaminophen, indomethacin, nabumetone, ketorolac, tenoxicam, tolmetin, piroxicam, fenoprofen, etodolac, naproxen, diflunisal, suprofen, bromfenac, ketoprofen, dihomo-gamma-linolenic acid, icosapent, fluriprofen, mefenamic acid, salsalate, sulindac, salicylic acid, lumiracoxib, O-acetyl-L-serine, phenacetin, fluriprofen methyl ester, metamizole, nitroaspirin, meloxicam, flufenamic acid, oxaprozin, tiaprofenic acid, magnesium salicylate, diethylcarbamazine, lornoxicam, carprofen, phenylbutazone, nepafenac, antipyrine, antrafenine, choline magnesium trisalicylate, triflusal, niflumic acid, dexibuprofen, aceclofenac, acemetacin, droxicam, loxoprofen, tolfenamic acid, dexketoprofen trometamol, talniflumate, propacetamol, trolamine salicylate, phenyl salicylate, bufexamac, glycol salicylate, menthyl salicylate, FK-506, lenalidomide, rofecoxib, valdecoxib, cimicoxib, chlorphenesin, clodronic acid, seliciclib, drospirenone, triamcinolone, pomalidomide, parecoxib, firocoxib, aclofenac, adapalene, thalidomide, etoricoxib, robenacoxib, asaraldehyde, zaltoprofen, deracoxib, dexamethasone, pranoprofen, amfenac sodium monohydrate, ampiroxicam, NS-398, bismuth subsalicylate, diclofenac diethylamine, trometamol, rutaecarpine, salicin, fenbufen, xanthohumol, flunixin meglumin and nimesulide.

7. The composition for according to any one of items 1 to 6, wherein one or more inhibitors are lipoxygenase and/or FLAP (ALOXSAP) inhibitors selected from the group consisting of MK886, zileuton, masoprocol, diethylcarbamazine, azelastine, benoxaprofen, nordihydroguaiaretic acid, abietic acid, esculetin, montelukast, minocycline, MLN-977, rhein, diacerein, nabiximols, fostamatinib, AM103, DG031, fiboflapon, AA-861 and atreleuton.

8. The composition for use according to any one of items 1 to 7, wherein one or more inhibitors are dual cyclooxygenase and lipoxygenase inhibitors, preferably selected from the group consisting of licofelone, darbufelone, CI-987, S-2474, KME-4,Chebulagic acid, balsalazide, mesalazine, sulfasalazine, aminosalicylic acid, meclofenamic acid, morniflumate diarylpyrazole derivatives, thieno[2,3-b]pyridine derivatives, N-substituted 5-aminosalicylicylamides, flavocoxid, indolizine derivatives, LQFM-091, hyperforin, celastrol, BW755C, tepoxalin,b-boswellic acid, D-002, 2,3-diarylxanthones, phenidone and ER-34122.

9. The composition for use according to any one of items 1 to 8, wherein the composition comprises an additional compound capable of inhibiting intracellular conversion of arachidonic acid.

10. The composition for use according to item 9, wherein the additional compound is a natural compound, preferably selected from the group consisting of turmeric, rosemary, ginger, oregano, resveratrol, curcumin, cannabinoids, ginseng, saponins, terpenoids, flavonoids, polyphenols, ginkgo biloba, capsaicin, genistein and kaempferol.

11. The composition for use according to item 9, wherein the additional compound is an inhibitor of cytochrome P450, preferably an inhibitor of CYP2J, CYP2C, CYP4A or CYP4F, preferably selected from the group consisting of sulfaphenazole, avasimibe, benzbromarone, rosiglitazone, troglitazone, cervistatin, warfarin, pioglitazone, lapatinib, trimethoprim, zafirlukast, amodiaquine, nicardipine, simvastatin, fluvastatin , loratadine, ethinylestradiol, irbesartan, quinine, sorafenib, eltrombopag, losartan, licofelone, amitriptyline, atorvastatin, mefenamic acid, meloxicam, piroxicam, erlotinib, pazopanib, diethylstilbestrol, enzalutamide, ponatinib, dabrafenib, enasidenib, lovastatin, montekulast, ketoconazole, felodipine, candesartan cilexetil, clotrimazole, mometasone, salmeterol, raloxifene, fenofibrate, levothyroxine, tamoxifen, oxybutynin, medroxyprogesterone acetate, nifedipine, liotrix, amlodipine, bezafibrate, chloramphenicol, cyclosporine, cimetidine, clopidogrel, cholecalciferol, delavirdine, dextropropoxyphene, etoposide, isoniazid, ketoprofen, metronidazole, nilutamide, nilvadipine, paroxetine, phenelzine, pravastatin, propafenone, pyrimethamine, rofecoxib, rutin, saquinavir, sulfamethoxazole, sulfinpyrazone, tegaserod, terfenadine, thioridazine, ticlopidine, tioconazole, triazolam, troleandomycin, valproic acid, abiraterone, vismodegib, regorafenib, trametinib, idelalisib, lopinavir, celecoxib, efavirenz, rabeprazole, teriflunomide, crisaborole, belinostat, topiroxostat, candesartan, letermovir, rucaparib, opicapone, nabilone, fluvoxamine, fluticasone, fluticasone furoate, fluticasone propionate, bosutinib, cabozantinib, genistein, lenvatinib, atazanavir, bexarotene, deferasirox, quinidine, mifepristone, vemurafenib, sildenafil, diclofenac, fluoxetine, valdecoxib, voriconazole, etodolac, sertraline, glyburide, acenocoumarol, rosuvastatin, imatinib, clozapine, diazepam, progesterone, omeprazole, valsartan, bortezomib, nevirapine, azelastine, lornoxicam, phenylbutazone, etravirine, leflunomide, sitaxentan, aminophenazone, verapamil, etoricoxib, propofol, sulfamoxole, dicoumarol, diltiazem, histamine, moclobemide, selegiline, parecoxib, doconexent, acetyl sulfisoxazole, fluconazole, pantoprazole, desloratadine, miconazole, amiodarone, gemfibrozil, probenecid, teniposide, sulfadiazine, capecitabine, fluorouracil, tranylcypromine, anastrozole, atovaquone, cyclizine, dexfenfluramine, disulfiram, epinephrine, eprosartan, flecainide, indinavir, methazolamide, nelfinavir, olanzapine, pranlukast, promethazine, sulfadimethoxine, sulfamethizole, sulfanilamide, sulfapyridine, methimazole, tolcapone, bicalutamide, armodafinil, agomelatine, noscapine, clevidipine, sulconazole, gefitinib, ticagrelor, ceritinib, floxuridine, lifitegrast, rhein, diacerein, zucapsaicin, stiripentol, lobeglitazone, dosulepin, manidipine, cimicifuga racemose, curcumin, felbamate, piperine, safinamide, irponiazid, oritavancin, masorpocol and pegvisomant.

12. The composition for use according to item 9, wherein the additional compound is an inhibitor of long-chain-fatty-acid-CoA ligase 4 (ACSL4), preferably selected from the group consisting of triacsin A, triacsin B, triacsin C, triacsin D, analogs of triacsin C N-ethylmaleimide, 2-fluoropalmitic acid, troglitazone, ciglitazone, pioglitazone and rosiglitazone.

13. The composition for use according to item 9, wherein the additional compound is an inhibitor of a lysophosphatidylcholine acyltransferase, specifically an inhibitor of LPCAT1, LPCAT2, LPCAT3, LPCAT4, MBOAT2 and/or MBOAT7, and wherein the inhibitor of a lysophosphatidylcholine acyltransferase is preferably selected from the group consisting of N-phenyl-maleimide derivatives, TSI-01 and thimerosal.

14. The composition for use according to item 9, wherein the additional compound is an inhibitor of a fatty acid elongase, specifically an inhibitor of ELOVL2, ELOVL4 and/or ELOVL5, and wherein the inhibitor of a fatty acid elongase is preferably selected from the group consisting of cycloate, adenosine 5'-hexadecylphosphate, endo-1k, (S)-1y and compound 37, 5,5-dimethyl-3-(5-methyl-3-oxo-2-phenyl-2,3-dihydro-1H-pyrazol-4-yl)-1-phenyl-3-(trifluoromethyl-3,5,6,7-tetrahydro-1H-indole-2,4-dione) and (3-endo)-3-(phenylsulfonyl)-N-[4-(trifluoromethyl)phenyl]-8-azabicyclo[3.2.1]octane-8-carboxamide.

15. The composition for use according to any one of items 1 to 9, wherein the composition comprises an additional compound capable of manipulating intracellular ATP levels.

16. The composition for use according to item 15, wherein the additional compound is an inhibitor of ATP synthases, preferably selected from the group consisting of oligomycin A, inositol nicotinate, bedaquiline, efrapeptins, leucinostatins, tentoxin, tentoxin derivates, angiostatin, enterostatin, melittin, $IF_1$, Syn-A2, Syn-C, resveratrol, piceatannol, diethylstilbestrol, 4-acetoamido-4'-isothiocyanostilbene-2,2'-disulfonate, 4,4'-D-isothiocyanatostilbene-2,2-disulfonic acid, kaempferol, morin, apigenin, genistein, biochanin A, daidzein, epicatechin gallate, epigallocatechin gallate, proanthocyanidin, curcumin, phloretin, theaflavin, tannic acid, 4-hydroxy-estradiol, 2-hydroxy-estradiol, 17α-estradiol, 17β-estradiol, α-zearalenol, β-zearalenol, oligomycin, venturicidin, apoptolidin, ossamycin, cytovaricin, peliomycin, tributyltin chloride, tricyclohexyltin hydroxide, triethyltin sulfate, triphenyltin chloride, dimethyltin 3-hydroxyflavone chloride, diethyltin 3-hydroxyflavone chloride, dibuthyltin 3-hydroxyflavone bromide, dioctyltin 3-hydroxyflavone chloride, diphenyltin 3-hydroxyflavone chloride, diethyltin 3,5,7,2',4'-pentahydroxyflavone chloride, dibutyltin 3,5,7,2',4'-pentahydroxyflavone bromide, diphenyltin 3,5,7,2',4'-pentahydroxyflavone chloride, tributyltin 3-hydroxyflavone, triethyllead, aurovertin, citreoviridin, asteltoxin, rhodamine B, rhodamine 123, rhodamine 6G, rosaniline, malachite green, brilliant green, quinacrine, quinacrine mustard, acridine orange, coriphosphine, pyronin Y, dequalinium, safranin O, Nile blue A, ethidium bromide, tetracaine, dibucaine, procaine, lidocaine, chlorpromazine, trifluoperazine, procainamide, propranolol, octyl guanidine, 1-dansyl amido-3-dimethypropylamine compounds, cetyltrim-ethylammonium, spermine, spermidine, bathophenan throline-metal chelate, 4,4-diphenyl-2,2-bipyridine, 3-(2-pyridyl)-5,6-diphenyl-1,2,4-triazine, atrazine, atrazine amino derivative, arsenate, aluminium fluo-ride, beryllium fluoride, scandium fluoride, vanadate, magnesium fluoride, sulfite, thiophosphate, azide, ANPP, phenylglyoxal, butanedione, dansyl chloride, 1-fluoro-2,4-dinitrobenzene, dicarbopolyborate, almi-trine, 5-hydroxy-1,2-naphtalene dicarboxylic anhy-dride, R207910, spegazzinine, n-butanol, tetrachloro-salicylanilide, dihydrostreptomycin, suramin, Bz-423, DMSO, hypochlorous acid, DDT, diazoxide, HNB, N-sulfonyl or N-alkyl substituted tetrahydrobenzodiaz-epine derivatives, 4-(N-arylimidazole)-substituted ben-zopyran derivatives, N-[1-aryl-2-(1-imidazolo)ethyl]-cyanoguanidine derivatives, N-[1-aryl-2-(1-imidazolo) ethyl]-acylguanidine derivatives, O-[1-aryl-2-(1-imidazolo)ethyl]-thiourethane derivatives, dio-9 complex, ethanol and zinc.

17. The composition for use according to item 15, wherein the additional compound is an inhibitor of ADP/ATP translocases, preferably selected from the group con-sisting of clodronic acid, ibipinabant, atractyloside, carboxyatractyloside, bongkrekic acid, isobongkrekic acid, MT-21, closantel, CD437, leelamine, L923-0673, IMD 0354, PI32-0333, S899542, nonactin and S838462.

18. The composition for use according to item 15, wherein the additional compound is an inhibitor of glycolysis, preferably selected from the group consisting of 2-de-oxy-D-glucose, lonidamine, bromopyruvic acid, phlo-retin, STF-31, WZB117, 3PO, 3-bromopyruvate, dichloroacetate, oxamic acid, NHI-1, oxythiamine, imatinib, glucosamine, 6-aminonicotinamide, genistein, 5-thioglucose, mannoheptulose, α-chlorohy-drin, ornidazole, oxalate, glufosfamide, N-(phospho-nacetyl)-L-aspartate, 6-methylmercaptopurine ribo-side, CGP 3466B maleate, sodium monofluorophosphate, DASA-58, DL-serine, dichloro-acetic acid, sodium dichloroacetate, nitrofural, 6-AN, fasentin, benserazide, astraglin, resveratrol, chrysin, GEN-27, apigenin, bis-2-(5-phenylacetamido-1,3,4-thiadiazol-2-yl)ethyl sulfide, CB-839, azaserine, acivi-cin, 6-diazo-5-ox-L-norleucine, thiazolidine-2,4-dione derivatives, compound 968, R-lipoic acid, 1,3,4-thia-diazole compounds, 2-chloropropionate, Nov3r, AZD7545, Pfz3, radicicol, mitaplatin, mito-DCA, phe-nylbutyrate, 4,5-diarylisoxazoles, VER-246608, betu-linic acid, pyruvate analogs containing phosphinate or phosphonate group, CPI-613, M77976, aromatic DCA derivatives, furan and thiophene carboxylic acids, rito-navir, FX11, oxamate, D-fructose-6-phosphate, 6-phos-phogluconic acid, N-bromoacetyl-aminoethyl phos-phate, 2-carboxyethylphosphonic acid, N-hydroxy-4-phosphono-butanamide, 2-phosphoglyceric acid, iodoacetate, gossypol, bisphosphonate analogs of 1,3-bisphosphoglyceric acid, benzene hexacarboxylic acid, 3-phosphoglyceric acid, phosphonoacetohydroxamic acid, 2-phospho-D-glyceric acid, TLN-232 and CAP-232.

19. The composition for use according to any one of items 1 to 18, wherein the composition prevents or delays the onset of a senescence-related disease or condition.

20. The composition for use according to any one of items 1 to 18, wherein the composition prevents or delays the progression of a senescence-related disease or condi-tion.

21. The composition for use according to any one of items 1 to 18, wherein the composition promotes the regres-sion of a senescence-related disease or condition.

22. The composition for use according to any one of items 19 to 21, wherein the senescence-related disease or condition is selected from cardiovascular disease, ath-erosclerosis, cancer, osteoporosis, osteoarthritis, neu-rological disorders, dementia, cataract, kidney disease, retinopathy, diabetes, lung fibrosis, vertebral skin degeneration, age-related muscular atrophy, hair loss and skin aging.

23. The composition for use according to any one of items 1 to 18, wherein the composition improves the perfor-mance of transplants.

24. The composition for use according to any one of items 1 to 18, wherein the composition prevents or attenuates senescence-associated scar formation and fibrosis.

25. The composition for use according to any one of items 1 to 18, wherein the composition ameliorates side effects of chemotherapy and prevents or delays tumor relapse.

26. A method of identifying senescent cells in a subject, comprising the steps of
a) providing a sample of said subject,
b) determining the intracellular level of at least one of lysophosphatidylcholine, arachidonic acid and/or phos-pholipase A2 activity in said sample,
c) comparing the level of b) to a reference level, wherein the reference level is the intracellular level of at least one of lysophosphatidylcholine, arachidonic acid and/or phospholipase A2 activity in non-senescent cells,
and wherein an increase of at least 2-fold in the level of lysophosphatidylcholine, arachidonic acid and/or phospho-lipase A2 activity is indicative of the presence of senescent cells in said sample.

27. A method of screening for candidate compounds for eliminating senescent cells, comprising the steps of
a) bringing at least one test compound in contact with a sample of senescent cells,
b) measuring the intracellular level of arachidonic acid and/or measuring apoptosis and/or measuring cell viability, and
c) selecting the test compounds which cause intracellular accumulation of arachidonic acid, increased apoptosis and/or reduced cell viability in the senescent cells contacted with the test compound compared to untreated senescent cells.

28. Use of a compound for eliminating senescent cells in a subject, wherein said compound is identified accord-ing to the method of item 27.

29. A composition comprising at least one cyclooxy-genase inhibitor and at least one lipoxygenase inhibitor for use in selectively eliminating senescent cells.

The examples described herein are illustrative of the present invention and are not intended to be limitations thereon. Different embodiments of the present invention have been described according to the present invention. Many modifications and variations may be made to the techniques described and illustrated herein without depart-ing from the spirit and scope of the invention. Accordingly, it should be understood that the examples are illustrative only and are not limiting upon the scope of the invention.

EXAMPLES

The following materials and methods were used throughout the examples provided herein unless indicated otherwise.

Cell isolation

Human dermal fibroblasts (HDFs) were isolated from skin biopsies of healthy female adult donors and obtained from Evercyte (Vienna, Austria). Foreskin human dermal fibroblasts (fHDFs) were isolated from foreskin and obtained from Evercyte (Vienna, Austria). Male human umbilical vein endothelial cells (HUVECs) were isolated from human umbilical cords and obtained from Evercyte (Vienna, Austria). All cell strains were tested for mycoplasma at regular intervals. Human lung fibroblasts (HLFs) were isolated from donor lungs and obtained from the Ludwig Boltzmann Institute for Lung Vascular Research (Graz, Austria). Human renal proximal epithelial cells (RPTECs) were obtained from Biopredic (Saint Gregoire, France).

Cell Culture

HDFs, fHDFs and HLFs were cultured with DMEM/ Ham's F-12 (1:1 mixture) (F4815, Biochrome) supplemented with 10% FCS (F7524, Sigma-Aldrich) and 4 mM L-Glutamine (G7513, Sigma-Aldrich) under ambient oxygen, 7% $CO_2$ and 37° C. HUVECs were cultured with Endopan 3 Kit (except for Gentamicin and FBS; P04-0010K, Pan Biotech) supplemented with 10% FCS (F7524, Sigma-Aldrich) under ambient oxygen, 7% $CO_2$ and 37° C. Cells were detached by incubation with 0.1% trypsin and 0.02% EDTA at 37° C. for 3-5 min and split at ratios between 1:2 and 1:8 depending on cell type and growth rate. RPTECs were cultured with ProxUp (MHT-003, Evercyte) without G418 under ambient oxygen, 7% $CO_2$ and 37° C. Cells were detached by incubation with 0.05% Trypsin-EDTA solution (25300054, Gibco) at 37° C. for 3-5 min and split at ratios between 1:2 and 1:4 depending on growth rate. Cells were counted using a Vi-CELL XR (Beckman Coulter) automated cell counter.

SIPS

Cells were seeded at a cell density of 2,800 cells/cm² one day prior to the treatment. The cells were treated nine times over a period of 11 days with 60-80 μM $H_2O_2$ supplemented to the media for one hour followed by a media change. Alternatively, depending on cell type cells were seeded at a cell density of 3,500-7,000 cells/cm² one day prior to the treatment and SIPS was induced with 100-200 nM doxorubicin (D1515, Sigma-Aldrich) supplemented to the medium for 6 days. Induction of senescence was verified by SA-β-gal staining, p21 expression, and absence of BrdU incorporation. AnnexinV/PI staining was performed to assure that the treatment was non-lethal and SIPS HDFs were cultured and monitored for over 50 days to assure that the induced growth arrest was permanent (Terlecki-Zaniewicz et al. 2018).

Lipid Analysis

Cells were washed once with PBS containing 0.5 mM diethylenetriaminepentaacetic acid and after adding 2.2 ml methanol containing 3% acetic acid and 0.01% butylated hydroxytoluene, cells were detached with a cell scraper. Lipid samples were transferred to a glass vial, air was evacuated with inert gas and samples were stored at –20° C. after vials were sealed with parafilm. Finally, samples were analyzed with flow-injection electrospray ionization mass spectrometry as described by (Gruber et al. 2015) using the version 1.6 of the Analyst software (Applied Biosystems). Levels of lyso PPC and lyso SPC were normalized to DPPC levels.

Next Generation Sequencing and Data Analysis

Library preparation and sequencing were performed on an Illumina HighSeq 2000 Platform (GATC Biotech AG; Konstanz, Germany). All analysis steps were done according to the Tuxedo Suite Pipeline (Trapnell et al. 2012). Briefly, Illumina Casava 1.8.2 software was used for base calling. RNA-seq reads were aligned to hg19 genome assembly using TOPHAT Version 2.0.13 with default parameters. Transcripts were assembled in Cufflinks Version 2.1.1 and differentially expressed genes were predicted by Cuffdiff.

Viability Assay

Alamar blue (DAL1100, Thermo Fisher Scientific) assay was performed according to the manufacturer's instructions. Cells were treated with the respective substances for 9 days with a media change on day 0, 3 and 6. The control was treated with the respective concentration of the solvent (DMSO).

Quantification of Arachidonic Acid

The cells were harvested by trypsinization, centrifuged at 1000 g and 4° C. for 5 min and washed three times with cold PBS. The Cells were counted using a Vi-CELL XR (Beckman Coulter) automated cell counter and the cell pellets were resuspended in cold PBS to obtain a cell suspension with 2000-5000 cells/μl. Subsequently the cells were lysed by 30 cycles of sonication (30 s on, 30 s off) in a Bioruptor (Diagenode). Cell debris was removed by 10 min centrifugation at 1500 g and 4° C. and the supernatant was analyzed with an ELISA assay (Novus Biologicals; NBP2-66372) according to the manufacturer's instructions.

PLA2 Activity Assay

The cells were harvested by trypsinization, centrifuged at 1000 g and 4° C. for 5 min and washed three times with cold PBS. The Cells were counted using a Vi-CELL XR (Beckman Coulter) automated cell counter and the cell pellets were resuspended in cold PBS to obtain a cell suspension with 2000-5000 cells/μl. Subsequently the cells were lysed by 30 cycles of sonication (30 s on, 30 s off) in a Bioruptor (Diagenode). Cell debris was removed by 10 min centrifugation at 1500 g and 4° C. and the supernatant was analyzed with the EnzChek™ Phospholipase A2 Assay Kit (ThermoFisher Scientific; E10217) according to the manufacturer's instructions.

Example 1

Altered Lipid Metabolism in Senescent Cells

Example 1A

Identification of Increased Levels of Lyso PC in Senescent Cells

As described herein an altered lipid metabolism in senescent cells was discovered and two species of lyso PC as novel biomarkers for senescence were identified using mass spectrometry. 1-stearoyl-2-hydroxy-sn-glycero-3-phosphocholine (18:0 lyso PC) and 1-palmitoyl-2-hydroxy-sn-glycero-3-phosphocholine (16:0 lyso PC) were upregulated during senescence in several primary human cell strains regardless of the inducer being telomere dependent (replicative senescence) or independent (stress-induced premature senescence; FIG. 1).

FIG. 1 shows that Lysophosphatidylcholines are elevated in senescent cells. FIG. 1a shows lipid analysis of human dermal fibroblasts (HDF) of three different donors at early, middle and late population doubling (PD), wherein levels of lyso PCs were normalized to Dipalmitoylphosphatidylcholine (DPPC) levels. FIG. 1*b* shows lipid analysis of stress-induced premature senescent (SIPS) HDF, four days after SIPS treatment. SIPS was induced with chronic oxidative stress treatment (9 doses of $H_2O_2$ treatment over the period of 11 days). FIG. 1*c* shows lipid analysis of stress-induced premature senescent (SIPS) HDF, seven days after SIPS treatment. SIPS was induced with Doxorubicin (2 subsequent treatments for 72 h with 100 nM). As a control for the SIPS treatment, cells were cultivated with normal growth medium, grown to confluence during the treatment and entered a quiescent state (Q). For FIG. 1*a* significance was calculated with a one-way ANOVA followed by a post hoc Tukey's test. For FIG. 1*b,c* significance was calculated with a two-tailed student's t-test.

Lyso PC can be generated from phosphatidylcholines (PC) either non-enzymatically through oxidation processes (Choi et al. 2011) or enzymatically through conversion by phospholipases with PLA2 activity (Six and Dennis 2000). Comparing RNA-seq expression data from SIPS HDF with quiescent control cells (raw data available with GEO accession number: GSE93535), we identified cytosolic phospholipase A2 (PLA2G4A), cytosolic phospholipase A2 gamma (PLA2G4C) and group XV phospholipase A2 (PLA2G15) as possible candidates for the observed effects (FIG. 2).

FIG. 2 shows that PLA2 activity and mRNA expression levels of proteins associated with PLA2 activity are elevated in senescent cells. FIG. 2*a* shows that phospholipases with PLA2 activity and secretory phospholipase A2 receptor are increased in SIPS HDFs. Premature senescence was induced in HDFs with chronic oxidative stress treatment (9 doses of $H_2O_2$ treatment over the period of 11 days). As a control for the SIPS treatment, cells were cultivated with normal growth medium, grew to confluency during the treatment and entered a quiescent state (Q). Four days after the SIPS treatment, RNA samples were prepared and RNA-seq was performed. Expression levels are displayed as Fragments Per Kilobase of transcript per Million mapped reads (FPKM). The p-values were corrected with the false discovery rate for multiple comparisons using the Benjamini-Hochberg method and error bars indicate confidence intervals (95%). FIG. 2*b* shows elevated levels of PLA2 activity in SIPS HDFs and HLFs. Premature senescence was induced in HDFs and HLFs with doxorubicin (2 subsequent treatments for 72 h with 100 nM). As a control for the SIPS treatment, cells were cultivated with normal growth medium, grew to confluency during the treatment and entered a quiescent state (Q).

Example 1B

Increased Production of Arachidonic Acid (AA) in Senescent Cells

The secretory phospholipase A2 receptor (PLA2R1), which induces cellular senescence (Augert et al. 2009) and is upregulated in our dataset (FIG. 2), is reported to induce the production of lyso PCs and the concurrent release of arachidonic acid (AA) by activation of PLA2G4A through phosphorylation by MAPKs (Fonteh et al. 2000; Pan et al. 2015; Scott et al. 2006).

Given the fact that the increase of lyso PC in senescence was robust in all examined cell strains independent of the senescence inducer indicates that the altered lipid metabolism may be used as a target for the development of a cytotoxic treatment specific for senescent cells and thereby for the prevention or therapy of senescence-associated diseases and disorders.

Increased formation of eicosanoids has been reported to be associated with cellular senescence and aging (Currais et al. 2016; Kabir et al. 2016; Li et al. 2015; Wang et al. 2016b). As shown herein, the generation of lyso PC is increased and increased generation of lyso PC leads to increased generation of AA as a byproduct (FIG. 1 and FIG. 16). AA in turn can be further metabolized to eicosanoids by enzymes such as cyclooxygenase and lipoxygenase. It has been reported that accumulation of intracellular AA could induce apoptosis at high concentrations of AA (Penzo et al. 2004).

As described herein for the first time, cell death caused by accumulation of intracellular levels of AA is observed predominantly in senescent cells as these cells have an altered lipid metabolism with a higher AA formation rate (FIG. 3). Indeed, as surprisingly shown in the examples below, novel senolytics were identified based on the senescent cell-specific alterations in the arachidonic acid metabolism and the altered arachidonic acid metabolism could be exploited to selectively eliminate senescent cells.

Example 2

Identification of Novel Senolytics

In accordance with the hypothesis established in Example 1B, inhibition of cyclooxygenases or lipoxygenases led to a cytotoxic effect, which was in general more severe in senescent cells (FIG. 4-15), indicating availability of good therapeutic windows. There was some difference between the four examined cell types (HDFs, HLFs, RPTECs and HUVECs) but inhibition of cyclooxygenases and/or lipoxygenases lead to the elimination of senescent cells in all cell lines. Differences between different inducers of senescence and different donors were less pronounced. This is in line with previous reports, showing a cell type dependent senolytic effect by other senolytic strategies (Fuhrmann-Stroissnigg et al. 2017; Schafer et al. 2017; Zhu et al. 2017; Zhu et al. 2016; Zhu et al. 2015).

The three reported prior-art senolytics Navitoclax (ABT263; Selleck Chemicals), Quercetin (Sigma-Aldrich) and the combination of Quercetin with Dasatinib (DQ; Cayman chemicals) showed no senolytic effects in HDFs (FIGS. 4 and 9). Only in HUVECs, Navitoclax was able to selectively eliminate senescent cells but not Quercetin (FIG. 5).

Example 2A

Identification of Novel Senolytics in Human Dermal Fibroblasts

First, the senolytic effect of either COX or ALOX-inhibitors alone was assessed. FIG. 4 shows the significant senolytic effects of the ALOX-5 inhibitor MK886 (Santa Cruz Biotechnology) and the COX inhibitor acetylsalicylic acid (ASA; Sigma-Aldrich) on human fibroblasts alone. These 2 drugs were also compared to prior-art senolytics Quercetin and Navitoclax.

Premature senescence was induced in HDF with chronic oxidative stress treatment (9 doses of $H_2O_2$ treatment over the period of 11 days). Quiescent cells were used as control. Treatment with senolytic substances started 11 days after completion of the SIPS treatment to allow for the establishment of a fully established senescent phenotype. Growth media were supplemented with senolytic substances for 9 days with media changes every 3 days. All samples, including the control, contained the same concentration of solvent (DMSO). Subsequently, the viability was assessed using an alamar blue assay (Thermo Fisher Scientific).

Indeed, MK886 and the COX inhibitor ASA reduced the viability of senescent cells compared to quiescent cells to a greater extent than the prior-art senolytics Quercetin and Navitoclax.

Example 2B

Identification of Novel Senolytics in HUVECs

The senolytic effect of either COX or ALOX-inhibitors as well as of a dual inhibitor was assessed on human umbilical vein endothelial cells (HUVECs). FIG. 5 shows the effect of the COX-1/2 inhibitor ASA and of the dual COX/LOX inhibitor Licofelone compared to prior-art senolytics Quercetin and Navitoclax.

Premature senescence was induced in HUVECs with doxorubicin (Sigma-Aldrich), which was supplemented to the growth media for 6 days. Treatment with senolytic substances started 8 days after completion of the SIPS treatment to allow for cells to enter senescence. Quiescent cells were used as control. Growth media was supplemented with senolytic substances for 9 days with media changes every 3 days. All samples, including the control, contained the same concentration of solvent (DMSO). Subsequently, the viability was assessed using an alamar blue assay (Thermo Fisher Scientific) (FIG. 5).

HUVECs were more susceptible to an inhibition of cyclooxygenases alone than HDFs. As expected and in line with a previous report (Zhu et al. 2016), Navitoclax did show considerable senolytic activity against HUVECs. In addition, the dual COX/LOX inhibitor Licofelone did also show a significant senolytic effect in HUVECs.

This confirmed the recent findings that different cell types react differently on senolytic compounds and indicates that cells from embryonic and neonatal origin might be more susceptible to senolytics in general (Hwang et al. 2018; Schafer et al. 2017). Surprisingly, the inhibition of AA metabolizing enzymes using cyclooxygenase and lipoxygenase inhibitors was senolytic in both cell types, HDFs and HUVECs, and, importantly, they are the only effective senolytic compounds reported for adult human dermal fibroblasts so far.

Example 3

Combined Inhibition of Cyclooxygenases and Lipoxygenases in HDFs

In order to increase the senolytic effects observed, inhibition of both cyclooxygenases and lipoxygenases using a combinatorial treatment was tested and indeed showed synergistic effects. Co-inhibition of cyclooxygenases and lipoxygenases with the combination of acetylsalicylic acid (ASA) or Diclofenac (Sigma-Aldrich) together with MK886 generated a potent senolytic effect in adult HDFs as well as in foreskin HDFs (FIG. 6-9). These results show, for the first time, that co-inhibition of cyclooxygenase and lipoxygenase effectively eliminates/destroys senescent cells.

This contradicts the findings in WO2019070407A1, where combined treatment with inhibitors of COX2 and ALOX5 resulted in an increase in the cell number of senescent cells. This increase was never observed in the experiments performed in the study for targeted elimination of senescent cells as presented herein and is actually explained by proliferation of the cells used in WO2019070407A1. This strongly indicates that the cells used in the experiments as described in WO2019070407A1 were still in the process of establishing the irreversible growth arrest associated with cellular senescence and is in line with the other results shown in WO2019070407A1. Thus, by treating the pre-senescent cells with inhibitors of COX2 and ALOX5, cells escaped the growth arrest and started to proliferate. In consequence, the secretion of SASP factors was reduced.

Premature senescence was induced in adult and foreskin HDFs with doxorubicin, which was supplemented to the growth media for 6 days. Treatment with senolytic substances started 8 days after completion of the SIPS treatment to allow for cells to enter senescence. Quiescent cells were used as control. Growth media was supplemented with senolytic substances for 9 days with media changes every 3 days. All samples, including the control, contained the same concentration of solvent (DMSO). Subsequently, the viability was assessed using an alamar blue assay (Thermo Fisher Scientific).

FIG. 6 shows the effect of single treatment on adult human dermal fibroblasts of the cell strain HDF161 using the ALOX-5 inhibitor MK886 and the COX-1/2 inhibitors ASA and Diclofenac or the COX-2 specific inhibitor Celecoxib (Sigma-Aldrich) compared to dual inhibition using either 0.4 mM ASA, 50 µM Diclofenac or 2 µM Celecoxib combined with increasing concentrations of MK886. Inhibition of COX-2 alone by Celecoxib did not show any senolytic effect, indicating that the inhibition of a single AA-metabolizing enzyme is not sufficient to reduce the cell viability in senescent cells. The $EC_{50}$ of MK886 as single treatment was 26.4 µM for senescent cells, whereas, combined with ASA, Diclofenac or Celecoxib, the $EC_{50}$ dropped to 18.8 µM, 9 µM and 17 µM respectively. More importantly, the fold changes between the $EC_{50}$ of senescent versus quiescent cells increased from 1.58 to 1.95, 2.53 and 2.55 respectively. This shows a synergistic effect of the combined inhibition of cyclooxygenase and lipoxygenase compared to inhibition of cyclooxygenase and lipoxygenase alone.

FIG. 7 shows the effect of single treatment on adult human dermal fibroblasts of the cell strain HDF164 using the COX inhibitor Diclofenac and the ALOX-5 inhibitor MK886 compared to dual inhibition using 0.4 mM ASA or 50, 100 or 200 µM Diclofenac combined with increasing concentrations of MK886. The $EC_{50}$ of MK886 as single treatment was 34.7 µM for senescent cells and dropped to 30.4 µM, 17.3 µM, 11.2 µM and 8.39 µM respectively. In addition, the fold changes between the $EC_{50}$ of senescent versus quiescent cells increased from 1.31 to 1.46, 1.61, 1.88 and 1.64 respectively, confirming the results of FIG. 7 in a cell strain derived of a different donor.

FIG. 8 shows the effect of single treatment on foreskin human dermal fibroblasts of the cell strain fHDF166 using the COX inhibitors ASA and Diclofenac as well as the ALOX-5 inhibitor MK886 compared to dual inhibition using 0.4 mM ASA or 50 µM Diclofenac combined with increasing concentrations of MK886. The $EC_{50}$ of MK886 as single treatment was 34 µM for senescent cells and dropped to 29.6 µM and 12.4 µM respectively. In line with the results obtained with adult human dermal fibroblasts as outlined above, the fold changes between the $EC_{50}$ of senescent versus quiescent cells increased from 1.49 to 1.51 and 2.52 respectively. Again, this shows the synergistic effect of the combined inhibition of cyclooxygenase and lipoxygenase compared to inhibition of cyclooxygenase and lipoxygenase alone, also in foreskin derived HDFs.

FIG. 9 shows the effect of single treatment on three cell strains of adult human dermal fibroblasts (HDF76, HDF161, HDF164) using the COX inhibitors ASA and Diclofenac and the ALOX-5 inhibitor MK886 compared to dual inhibition using 0.4 mM ASA or 50 µM Diclofenac combined with increasing concentrations of MK886. In addition, the two prior-art senolytics Navitoclax and the combination of 15 µM Quercetin with increasing concentrations of Dasatinib were tested. When combining the data of three different HDF donors, the $EC_{50}$ value of senescent cells was not significantly reduced by the single treatment with MK886, ASA and Diclofenac as well as with Navitoclax and DQ. However, when MK886 was combined with a cyclooxygenase inhibitor, the $EC_{50}$ value was significantly lower in senescent cells when compared to quiescent control cells, confirming the results of FIGS. 6 and 7.

Example 4

Inhibition of AA Recycling by Triacsin C (TrC), an Inhibitor of Long-Chain-Fatty-Acid-CoA Ligase 4 (ACSL4)

Besides the Eicosanoid synthesis, the most efficient way to regulate the levels of pro-apoptotic free AA in cells is the re-integration into phospholipids via the Lands cycle (Murphy and Folco 2019).

Indeed, key enzymes of the Lands cycle were significantly elevated in senescent cells (FIG. 10). Long-chain-fatty-acid-CoA ligase 4 (ACSL4) and long-chain-fatty-acid-CoA ligase 1 (ACSL1) are two members of the acyl-CoA synthetase family, which are required for the activation of free fatty acids with CoA, generating acyl-CoA, the precursor for the re-integration and degradation processes in the Lands cycle. In addition, lysophospholipid acyltransferase 7 (MBOAT7) was found, the enzyme responsible for the re-integration of AA-CoA into phosphatidylinositol, to be increased in senescent cells. This strongly suggests that senescent cells regulate their levels of free AA through the rapid recycling processes of the Lands cycle.

Thus, the inhibition of key enzymes of the Lands cycle should reduce the capacity of senescent cells to protect themselves from the increased formation of pro-apoptotic intracellular AA and thereby result in a senolytic effect of such inhibitors.

FIG. 11 shows the effect of single treatment on three cell strains of adult human dermal fibroblasts (HDF76, HDF161, HDF164) using the ACSL4 inhibitor Triacsin C (TrC) compared to dual inhibition using 0.5 µM TrC or 50 µM Diclofenac combined with increasing concentrations of MK886. Single inhibition of ACSL4 and dual inhibition of ACSL4 and ALOXS was already enough to induce a significant senolytic effect, whereas the effect of MK886 alone was not significant (FIG. 9). Combined inhibition of ACSL4, ALOXS and COX1/2 decreased the $EC_{50}$ value even more.

FIG. 12 shows the effect of single treatment on human lung fibroblasts (HLFs) of the cell strain HLF102 using the ACSL4 inhibitor TrC compared to dual inhibition using 1 µM MK886 or 50 µM Diclofenac combined with increasing concentrations of TrC. Again, single inhibition of ACSL4 was enough to induce a potent senolytic effect with an $EC_{50}$ fold change of 9.19 between senescent and quiescent cells. When combined with inhibition of ALOXS and COX1/2 the $EC_{50}$ fold change could be further increased to 13.75, confirming the results from experiments with dermal fibroblasts.

FIG. 13 shows the effect of single treatment on human renal proximal epithelial cells (RPTECs) of the cell strain RPTEC1 using the ACSL4 inhibitor TrC, the COX inhibitor Diclofenac as well as the ALOX-5 inhibitor MK886 compared to dual inhibition using 0.1 µM TrC or 25 µM Diclofenac combined with increasing concentrations of MK886. Again, single inhibition of ACSL4 was enough to induce a potent senolytic effect with an $EC_{50}$ fold change of around 350 between senescent and quiescent cells. Single inhibition of COX1/2 and ALOXS resulted in an $EC_{50}$ fold change of 3.02 and 2.66, respectively, which could be further increased to 5.11 by combined inhibition of ALOX5 and COX1/2. Inhibition of ACSL4, ALOX5 and COX1/2 resulted in an $EC_{50}$ fold change of around 700. These results clearly indicate the feasibility and efficacy of the present approach to selectively eliminate senescent cells by inhibition of free intracellular AA conversion.

Example 5

Combining Cyclooxygenase/Lipoxygenase Inhibition with ATP Depletion

Lowering ATP levels by inhibition of ATP synthase, ADP/ATP translocase or glycolysis potentiated AA-induced mitochondrial membrane permeability in heart mitochondria indicating that AA-induced apoptosis can be further enhanced by depleting ATP levels.

Premature senescence was induced in adult HDFs with doxorubicin, which was supplemented to the growth media for 6 days. Treatment with senolytic substances started 8 days after completion of the SIPS treatment to allow cells to enter senescence. Quiescent cells were used as control. Growth media was supplemented with senolytic substances for 9 days with media changes every 3 days. All samples, including the control, contained the same concentration of solvent (DMSO). Subsequently, the viability was assessed using an alamar blue assay (Thermo Fisher Scientific).

Indeed, addition of 5 µM Oligomycin A (OmA; Cayman Chemicals), an inhibitor of ATP synthase, to the combination treatment of 0.4 mM ASA and MK886 further increased the senolytic effect by lowering the $EC_{50}$ for senescent cells from 30.4 µM to 9.9 µM and increased the fold changes between the $EC_{50}$ of senescent versus quiescent cells from 1.46 to 4.51 (FIG. 14). This indicates that the AA-induced apoptosis in senescent cells is ATP sensitive and can thus be further enhanced by ATP depletion.

Example 6

Combining Cyclooxygenase/Lipoxygenase Inhibition with Inhibition of the Calcineurin-NFAT Pathway Lowering the expression levels of enzymes, which are metabolizing AA is also expected to have a senolytic effect and can be used as a combinatorial senolytic treatment together with the inhibition of the COX/ALOX enzymatic activity, increasing the apoptotic pressure even further in senescent cells. Pathway analysis of our RNA-seq dataset (Lämmermann et al. 2018) indicated that the calcineurin-NFAT pathway is highly upregulated in SIPS HDFs compared to quiescent cells. Cyclosporin A (CsA) is a potent inhibitor of the calcineurin-NFAT pathway and was previously shown to also downregulate COX-2 expression (Hernández et al. 2001; Lotzer et al. 2007; Yiu and Toker 2006).

In order to test this, premature senescence was induced in foreskin HDFs with doxorubicin, which was supplemented to the growth media for 6 days. Treatment with senolytic substances started 8 days after completion of the SIPS treatment to allow for cells to enter senescence. Quiescent cells were used as control. Growth media was supplemented with senolytic substances for 9 days with media changes every 3 days. All samples, including the control, contained the same concentration of solvent (DMSO). Subsequently, the viability was assessed using an alamar blue assay (Thermo Fisher Scientific).

Interestingly, adding 2 μM of CsA (Santa Cruz Biotechnology) to the combination treatment of 0.4 mM ASA and MK886 lowered the $EC_{50}$ for senescent cells from 29.6 μM to 14.9 μM and increased the fold changes between the $EC_{50}$ of senescent versus quiescent cells from 1.51 to 2.81 (FIGS. 15 and 16).

Taken together, methods and compositions targeting the lipid metabolism therefore represent a promising way to eliminate senescent cells and treat senescence-associated diseases and disorders. The present results demonstrate that the inhibition of AA utilizing enzymes results in a senolytic effect in adult HDFs and in foreskin HDFs as well as in neonatal HUVECs. The two reported senolytics Quercetin and Navitoclax did not show considerable senolytic activity, except for Navitoclax in doxorubicin-induced senescent HUVECs. In contrast to Navitoclax, there are no serious side effects reported for the inhibition of cyclooxygenases and/or lipoxygenases. In addition, the dual inhibition of cyclooxygenases and lipoxygenases showed a synergistic effect in senescent HDFs of adult origin making them uniquely qualified to treat and prevent senescence-associated diseases and disorders.

As shown herein, the senolytic effect of the inhibition of cyclooxygenases and/or lipoxygenases could additionally be enhanced by simultaneous inhibition of ATP synthase and calcineurin. Inhibiting further AA-utilizing or AA-level-manipulating enzymes and pathways such as cytochrome P450, long-chain-fatty-acid-CoA ligase 4 (ACSL4), lyso-phosphatidylcholine acyltransferases or fatty acid elongases further potentiates the senolytic effect of cyclooxygenase and/or lipoxygenase inhibitors.

Example 7

Quantitative Analysis of AA

As described herein, the senolytic effect is caused by increasing the intracellular levels of AA above a certain threshold and thereby inducing cell death. This can be verified by measuring the intracellular AA levels of quiescent and senescent cells before and after inhibiting AA utilizing metabolic pathways. This is expected to increase the intracellular AA levels of senescent cells above a critical threshold that will not be reached by quiescent cells under the same conditions. Intracellular AA levels can be quantified using quantitative analytical methods such as ELISA, mass spectrometry or HPLC.

In order to verify, whether novel senolytics can be identified in an efficient screen measuring the intracellular levels of AA, an ELISA test (Novus Biologicals; NBP2-66372) was used according to the manufacturer's instructions to first, confirm that novel senolytics identified in the examples above indeed lead to an accumulation of intracellular AA, and second, to screen for compounds, which cause an increase of intracellular levels of AA in senescent HDFs.

As expected, the intracellular concentration of AA was higher in senescent cells compared to quiescent control cells and by blocking the production of eicosanoids for 6 hrs with the COX-1/2 inhibitor Diclofenac and the ALOX-5 inhibitor MK886 the intracellular AA levels could be increased (FIG. 17).

The senolytic effect of compounds identified in the ELISA screen is then tested using a dose response assay in adult and foreskin HDFs as described for COX and ALOX inhibitors above. Such compounds will also be used as senolytic drugs that target the AA metabolism.

Example 8

Rescue of Senolytic Effect by Manipulating cPLA$_2$-activity

As the senolytic effect of inhibitors against AA converting enzymes is based on the elevated PLA$_2$-activity of senescent cells, either increasing the PLA$_2$-activity in quiescent cells or decreasing the PLA$_2$-activity in senescent cells should ablate the differential susceptibility to cell death induced by inhibition of AA converting enzymes. Doxorubicin-induced premature senescent HDF76, HDF85, HDF161 (SIPS) and quiescent control cells (Q) were either treated for 72 hours with the combination of 1 μM ACSL4 inhibitor Triacsin C (TrC) and 1 μM ALOXS inhibitor MK886 alone or in addition with either 2.5 μM A23187 (cPLA2 activator) or 12.5 μM ASB14780 (cPLA2 inhibitor). ACSL4 inhibition combined with ALOX5 alone showed a significant senolytic effect in HDFs as seen in FIG. 11.

In line with the model presented herein, FIG. 18 shows a senolytic effect in HDFs after the combinatorial treatment with 1 μM Trc (ACSL4 inhibitor) and 1 μM MK886 (ALOX5 inhibitor), as was already observed in FIG. 11. When the senolytic treatment was combined with 2.5 μM A23187 (Cayman Chemicals, Cay11016-1), a known activator of the cytosolic phospholipase A$_2$, the viability of both, senescent as well as quiescent cells, was reduced and reached a similar level, thereby abolishing the senolytic effect of the treatment. This was also the case, when the enzymatic activity of the cytosolic phospholipase A$_2$ was reduced by the small molecule inhibitor ASB14780 (Sigma Aldrich, SML1913). Treatment with 12.5 μM ASB14780 reduced the cytotoxic effect of TrC and MK886 on senescent cells, whereas the viability of quiescent cells was only affected to a minor extent. This indicates that the increased PLA$_2$-activity of senescent cells is responsible of the observed senolytic effect of inhibitors of AA converting enzymes.

REFERENCES

Acosta J C, Banito A, Wuestefeld T, Georgilis A, Janich P, Morton J P, et al. A complex secretory program orchestrated by the inflammasome controls paracrine senescence. Nat. Cell Biol. 2013; 15(8):978-90 Available from: http://www.pubmedcentral.nih.gov/articlerenderfcgi?artid=3732483&tool=pmcentrez&rendertype=abstract Askari B, Kanter J E, Sherrid A M, Golej D L, Bender A T, Liu J, et al. Rosiglitazone inhibits acyl-CoA synthetase activity and fatty acid partitioning to diacylglycerol and triacylglycerol via a peroxisome proliferator-activated receptor-gamma-independent mechanism in human arterial smooth muscle cells and macrophages. Diabetes. NIH Public Access; 2007; 56(4):1143-52 Available from: http://www.ncbi.nlm.nih.gov/pubmed/17259370

Augert A, Payre C, de Launoit Y, Gil J, Lambeau G, Bernard D. The M-type receptor PLA2R regulates senescence through the p53 pathway. EMBO Rep. European Molecular Biology Organization; 2009; 10(3):271-7 Available from: http://www.ncbi.nlm.nih.gov/pubmed/19197340

Baar M P, Brandt R M C, Putavet D A, Klein J D D, Derks K W J, Bourgeois B R M, et al. Targeted Apoptosis of Senescent Cells Restores Tissue Homeostasis in Response to Chemotoxicity and Aging. Cell. 2017; 169(1):132-147.e16 Available from: http://linkinghub.elsevier.com/retrieve/pii/S0092867417302465

Baker D J, Childs B G, Durk M, Wijers M E, Sieben C J, Zhong J, et al. Naturally occurring p16 Ink4a -positive cells shorten healthy lifespan. Nature. Nature Publishing Group; 2016; 1-20 Available from: http://dx.doi.org/10.1038/nature16932

Baker D J, Wijshake T, Tchkonia T, LeBrasseur N K, Childs B G, van de Sluis B, et al. Clearance of p16Ink4a-positive senescent cells delays ageing-associated disorders. Nature. Nature Publishing Group; 2011; 479(7372):232-6 Available from: http://www.pubmedcentral.nih.gov/articlerenderfcgi?artid=3468323&tool=pmcentrez&rendertype=abstract Braun H, Schmidt B M W, Raiss M, Baisantry A, Mircea-Constantin D, Wang S, et al. Cellular Senescence Limits Regenerative Capacity and Allograft Survival. J. Am. Soc. Nephrol. 2012; 23(9):1467-73 Available from: http://www.ncbi.nlm.nih.gov/pubmed/22797186

Brideau C, Kargman S, Liu S, Dallob A L, Ehrich E W, Rodger I W, et al. A human whole blood assay for clinical evaluation of biochemical efficacy of cyclooxygenase inhibitors. Inflamm. Res. Birkhauser-Verlag; 1996; 45(2):68-74 Available from: http://link.springer.com/10.1007/BF02265118

Bussian T J, Aziz A, Meyer C F, Swenson B L, van Deursen J M, Baker D J. Clearance of senescent glial cells prevents tau-dependent pathology and cognitive decline. Nature. 2018; Available from: http://www.ncbi.nlm.nih.gov/pubmed/30232451

Campisi J, d'Adda di Fagagna F. Cellular senescence: when bad things happen to good cells. Nat. Rev. Mol. Cell Biol. 2007; 8(9):729-40

Chang J, Wang Y, Shao L, Laberge R-M, Demaria M, Campisi J, et al. Clearance of senescent cells by ABT263 rejuvenates aged hematopoietic stem cells in mice. Nat. Med. Nature Publishing Group; 2016; 22(1):78-83 Available from: http://www.nature.com/doifinder/10.1038/nm.4010%5Cnhttp://www.ncbi.nlm.nih.gov/pubmed/26657143

Childs B G, Baker D J, Wijshake T, Conover C A, Campisi J, van Deursen J M. Senescent intimal foam cells are deleterious at all stages of atherosclerosis. Science. 2016; 354(6311):472-7 Available from: http://www.sciencemag.org/cgi/doi/10.1126/science.aaf6659

Choi J, Zhang W, Gu X, Chen X, Hong L, Laird J M, et al. Lysophosphatidylcholine is generated by spontaneous deacylation of oxidized phospholipids. Chem. Res. Toxicol. 2011; 24(1):111-8 Available from: http://pubs.acs.org/doi/abs/10.1021/tx100305b Coppé J-P, Desprez P-Y, Krtolica A, Campisi J. The Senescence-Associated Secretory Phenotype: The Dark Side of Tumor Suppression. Annu Rev Pathol. 2010; 5:99-118

Currais A, Quehenberger O, M Armando A, Daugherty D, Maher P, Schubert D. Amyloid proteotoxicity initiates an inflammatory response blocked by cannabinoids. npj Aging Mech. Dis. 2016; 2(1):16012 Available from: http://www.ncbi.nlm.nih.gov/pubmed/28721267

Demaria M, Ohtani N, Youssef S, Rodier F, Toussaint W, Mitchell J, et al. An essential role for senescent cells in optimal wound healing through secretion of PDGF-AA. Dev. Cell. 2014; 31(6):722-33

Dörr J R, Yu Y, Milanovic M, Beuster G, Zasada C, Däbritz J H M, et al. Synthetic lethal metabolic targeting of cellular senescence in cancer therapy. Nature. 2013; 501 (7467):421-5 Available from: http://www.nature.com.sire.ub.edu/nature/journal/v501/n7467/full/nature12437.html Farr J N, Xu M, Weivoda M M, Monroe D G, Fraser D G, Onken J L, et al. Targeting cellular senescence prevents age-related bone loss in mice. Nat. Med. 2017; 23(9):1072-9 Available from: http://www.ncbi.nlm.nih.gov/pubmed/28825716

Fonteh A N, Atsumi G, LaPorte T, Chilton F H. Secretory phospholipase A2 receptor-mediated activation of cytosolic phospholipase A2 in murine bone marrow-derived mast cells. J. Immunol. 2000; 165(5):2773-82 Available from: http://www.ncbi.nlm.nih.gov/pubmed/10946309

Fuhrmann-Stroissnigg H, Ling Y Y, Zhao J, McGowan S J, Zhu Y, Brooks R W, et al. Identification of HSP90 inhibitors as a novel class of senolytics. Nat. Commun. 2017; 8(1):422 Available from: http://www.ncbi.nlm.nih.gov/pubmed/28871086

Gruber F, Ornelas C M, Karner S, Narzt M-S, Nagelreiter I M, Gschwandtner M, et al. Nrf2 deficiency causes lipid oxidation, inflammation, and matrix-protease expression in DHA-supplemented and UVA-irradiated skin fibroblasts. Free Radic. Biol. Med. 2015; 88(Pt B):439-51 Available from: http://www.ncbi.nlm.nih.gov/pubmed/25981373

Hernandez G L, Volpert O V, Iniguez M A, Lorenzo E, Martinez-Martinez S, Grau R, et al. Selective inhibition of vascular endothelial growth factor-mediated angiogenesis by cyclosporin A: roles of the nuclear factor of activated T cells and cyclooxygenase 2. J. Exp. Med. 2001; 193(5):607-20 Available from: http://www.ncbi.nlm.nih.gov/pubmed/11238591

Hubackova S, Davidova E, Rohlenova K, Stursa J, Werner L, Andera L, et al. Selective elimination of senescent cells by mitochondrial targeting is regulated by ANT2. Cell Death Differ. 2018; Available from: http://www.nature.com/articles/s41418-018-0118-3

Hutchinson J H, Li Y, Arruda J M, Baccei C, Bain G, Chapman C, et al. 5-Lipoxygenase-Activating Protein Inhibitors: Development of 3-[3-tert-Butylsulfanyl-1-[4-(6-methoxy-pyridin-3-yl)-benzyl]-5-(pyridin-2-ylmethoxy)-1H -indol-2-yl]-2,2-dimethyl-propionic Acid (AM103). J. Med. Chem. American Chemical Society; 2009; 52(19):5803-15 Available from: https://pubs.acs.org/doi/10.1021/jm900945d Hwang H V., Tran D T, Rebuffatti M N, Li C-S, Knowlton A A. Investigation of quercetin and hyperoside as senolytics in adult human endothelial cells. Minamino T, editor. PLoS One. 2018; 13(1):e0190374 Available from: http://www.ncbi.nlm.nih.gov/pubmed/29315311

Jeon O H, Kim C, Laberge R-M, Demaria M, Rathod S, Vasserot A P, et al. Local clearance of senescent cells attenuates the development of post-traumatic osteoarthritis and creates a pro-regenerative environment. Nat. Med. 2017; Available from: http://www.ncbi.nlm.nih.gov/pubmed/28436958

Jeschek D, Lhota G, Wallner J, Vorauer-Uhl K. A versatile, quantitative analytical method for pharmaceutical relevant lipids in drug delivery systems. J. Pharm. Biomed.

Anal. 2016; 119:37-44 Available from: https://linkinghub.el-sevier.com/retrieve/pii/S0731708515302405

Kabir T, Leigh R, Tasena H, Mellone M, Coletta R, Parkinson E, et al. A miR-335/COX-2/PTEN axis regulates the secretory phenotype of senescent cancer-associated fibroblasts. Aging (Albany. N.Y.). 2016; 8(8):1608-35 Available from: http://www.ncbi.nlm.nih.gov/pubmed/27385366

Kim Y, George D, Prior A M, Prasain K, Hao S, Le D D, et al. Novel triacsin C analogs as potential antivirals against rotavirus infections. Eur. J. Med. Chem. 2012; 50:311-8 Available from: http://www.ncbi.nlm.nih.gov/pubmed/22365411

Kim J-H, Lewin T M, Coleman RA. Expression and Characterization of Recombinant Rat Acyl-CoA Synthetases 1,4, and 5. J. Biol. Chem. 2001; 276(27):24667-73 Available from: http://www.ncbi.nlm.nih.gov/pubmed/11319222

Krtolica A, Parrinello S, Lockett S, Desprez P Y, Campisi J. Senescent fibroblasts promote epithelial cell growth and tumorigenesis: a link between cancer and aging. Proc. Natl. Acad. Sci. U.S.A. 2001; 98(21):12072-7 Available from: http://www.pubmedcentral.nih.gov/articlerenderfcgi?artid=59769&tool=pmcentrez&rendertype=abstract Lämmermann I, Terlecki-Zaniewicz L, Weinmüllner R, Schosserer M, Dellago H, de Matos Branco A D, et al. Blocking negative effects of senescence in human skin fibroblasts with a plant extract. npj Aging Mech. Dis. 2018; 4(1):4 Available from: http://www.ncbi.nlm.nih.gov/pubmed/29675264

Lehmann M, Korfei M, Mutze K, Klee S, Skronska-Wasek W, Alsafadi H N, et al. Senolytic drugs target alveolar epithelial cell function and attenuate experimental lung fibrosis ex vivo. Eur. Respir. J. 2017; 50(2):1602367 Available from: http://www.ncbi.nlm.nih.gov/pubmed/28775044

Lewis D A, Travers J B, Machado C, Somani A-K, Spandau D F. Reversing the aging stromal phenotype prevents carcinoma initiation. Aging (Albany. NY). 2011; 3(4):407-16 Available from: http://www.ncbi.nlm.nih.gov/pubmed/21515933

Li Y, Lei D, Swindell W R, Xia W, Weng S, Fu J, et al. Age-Associated Increase in Skin Fibroblast-Derived Prostaglandin E2 Contributes to Reduced Collagen Levels in Elderly Human Skin. J. Invest. Dermatol. 2015; 135(9):2181-8 Available from: http://www.ncbi.nlm.nih.gov/pubmed/25905589

Lötzer K, Jahn S, Kramer C, Hildner M, Nosing R, Funk C D, et al. 5-Lipoxygenase/cyclooxygenase-2 cross-talk through cysteinyl leukotriene receptor 2 in endothelial cells. Prostaglandins Other Lipid Mediat. 2007; 84(3-4)108-15 Available from: http://www.ncbi.nlm.nih.gov/pubmed/17991613

Milanovic M, Fan D N Y, Belenki D, Däbritz J H M, Zhao Z, Yu Y, et al. Senescence-associated reprogramming promotes cancer stemness. Nature. 2017; 553(7686):96-100 Available from: http://www.ncbi.nlm.nih.gov/pubmed/29258294

Muñoz-Espin D, Cañamero M, Maraver A, Gómez-López G, Contreras J, Murillo-Cuesta S, et al. Programmed Cell Senescence during Mammalian Embryonic Development. Cell. Cell Press; 2013; 155(5):1104-18 Available from: https://www.sciencedirect.com/science/article/pii/S0092867413012956

Murphy R C, Folco G. Lysophospholipid acyltransferases and leukotriene biosynthesis: intersection of the Lands cycle and the arachidonate PI cycle. J. Lipid Res. American Society for Biochemistry and Molecular Biology; 2019; 60(2):219-26 Available from: http://www.jlr.org/content/60/2/219.long Nishikiori M, lizuka H, Ichiba H, Sadamoto K, Fukushima T. Determination of Free Fatty Acids in Human Serum by HPLC with Fluorescence Detection. J. Chromatogr. Sci. Oxford University Press; 2015; 53(4):537-41 Available from: https://academic.oup.com/chromsci/article-lookup/doi/10.1093/chromsci/bmu081

Pan J, Li D, Xu Y, Zhang J, Wang Y, Chen M, et al. Inhibition of Bcl-2/xl With ABT-263 Selectively Kills Senescent Type II Pneumocytes and Reverses Persistent Pulmonary Fibrosis Induced by Ionizing Radiation in Mice. Int. J. Radiat. Oncol. Biol. Phys. 2017; 99(2)

Pan Y, Wan J, Liu Y, Yang Q, Liang W, Singhal P C, et al. sPLA2 IB induces human podocyte apoptosis via the M-type phospholipase A2 receptor. Sci. Rep. 2015; 4(1):6660 Available from: http://www.ncbi.nlm.nih.gov/pubmed/25335547

Penzo D, Petronilli V, Angelin A, Cusan C, Colonna R, Scorrano L, et al. Arachidonic acid released by phospholipase A(2) activation triggers Ca(2+)-dependent apoptosis through the mitochondrial pathway. J. Biol. Chem. American Society for Biochemistry and Molecular Biology; 2004; 279(24):25219-25 Available from: http://www.ncbi.nlm.nih.gov/pubmed/15070903

Prior A M, Zhang M, Blakeman N, Datta P, Pham H, Chen Q, et al. Inhibition of long chain fatty acyl-CoA synthetase (ACSL) and ischemia reperfusion injury. Bioorg. Med. Chem. Lett. Pergamon; 2014; 24(4):1057-61 Available from: https://www.sciencedirect.com/science/article/pii/S0960894X14000353?via%3Dihub Ressler S, Bartkova J, Niederegger H, Bartek J, Scharffetter-Kochanek K, Jansen-Dürr P, et al. p16INK4A is a robust in vivo biomarker of cellular aging in human skin. Aging Cell. 2006; 5(5):379-89 Available from: http://doi-.wiley.com/10.1111/j.1474-9726.2006.00231.x Roos C M, Zhang B, Palmer A K, Ogrodnik M B, Pirtskhalava T, Thalji N M, et al. Chronic senolytic treatment alleviates established vasomotor dysfunction in aged or atherosclerotic mice. Aging Cell. 2016; 15(5):973-7 Available from: http://www.ncbi.nlm.nih.gov/pubmed/26864908

Sandoval A, Chokshi A, Jesch E D, Black P N, DiRusso C C. Identification and characterization of small compound inhibitors of human FATP2. Biochem. Pharmacol. 2010; 79(7):990-9 Available from: http://www.ncbi.nlm.nih.gov/pubmed/19913517

Schafer M J, White T A, lijima K, Haak A J, Ligresti G, Atkinson E J, et al. Cellular senescence mediates fibrotic pulmonary disease. Nat. Commun. 2017; 8

Schmitt R, Melk A. Molecular mechanisms of renal aging. Kidney Int. 2017; 92(3):569-79 Available from: http://www.ncbi.nlm.nih.gov/pubmed/28729036

Scott G A, Jacobs SE, Pentland AP. sPLA2-X Stimulates Cutaneous Melanocyte Dendricity and Pigmentation Through a Lysophosphatidylcholine-Dependent Mechanism. J. Invest. Dermatol. 2006; 126(4):855-61 Available from: http://www.ncbi.nlm.nih.gov/pubmed/16456529

Six D A, Dennis E A. The expanding superfamily of phospholipase A(2) enzymes: classification and characterization. Biochim. Biophys. Acta. 2000; 1488(1-2):1-19 Available from: http://www.ncbi.nlm.nih.gov/pubmed/11080672

Terlecki-Zaniewicz L, Lämmermann I, Latreille J, Bobbili M R, Pils V, Schosserer M, et al. Small extracellular vesicles and their miRNA cargo are anti-apoptotic members of the senescence-associated secretory phenotype. Aging (Albany. N.Y.). 2018; Available from: http://www.ncbi.nlm.nih.gov/pubmed/29779019

Trapnell C, Roberts A, Goff L, Pertea G, Kim D, Kelley D R, et al. Differential gene and transcript expression analysis of RNA-seq experiments with TopHat and Cufflinks. Nat. Protoc. 2012; 7(3):562-78 Available from: http://www.ncbi.nlm.nih.gov/pubmed/22383036

Valentijn F A, Falke L L, Nguyen T Q, Goldschmeding R. Cellular senescence in the aging and diseased kidney. J. Cell Commun. Signal. Springer; 2018; 12(1):69-82 Available from: http://www.ncbi.nlm.nih.gov/pubmed/29260442

Wang Y, Chang J, Liu X, Zhang X, Zhang S, Zhang X, et al. Discovery of piperlongumine as a potential novel lead for the development of senolytic agents. Aging (Albany. N.Y.). 2016a; 8(11):2915-26 Available from: http://www.ncbi.nlm.nih.gov/pubmed/27913811

Wang X-F, Huang Y-F, Wang L, Xu L-Q, Yu X-T, Liu Y-H, et al. Photo-protective activity of pogostone against UV-induced skin premature aging in mice. Exp. Gerontol. 2016b; 77:76-86 Available from: http://www.ncbi.nlm.nih.gov/pubmed/26929999

Wang H, Nair M G, Strasburg G M, Booren A M, Gray I, Dewitt D L. Cyclooxygenase active bioflavonoids from Balaton™ tart cherry and their structure activity relationships. Phytomedicine. Urban & Fischer; 2000; 7(1):15-9 Available from: https://www.sciencedirect.com/science/article/pii/S0944711300800161?via%3Dihub Xu M, Palmer A K, Ding H, Weivoda M M, Pirtskhalava T, White T A, et al. Targeting senescent cells enhances adipogenesis and metabolic function in old age. Elife. 2015; 4(December):e12997 Available from: http://elifesciences.org/lookup/doi/10.7554/eLife.12997

Yiu G K, Toker A. NFAT induces breast cancer cell invasion by promoting the induction of cyclooxygenase-2. J. Biol. Chem. 2006; 281(18):12210-7 Available from: http://www.jbc.org/lookup/doi/10.1074/jbc.M600184200

Yosef R, Pilpel N, Tokarsky-Amiel R, Biran A, Ovadya Y, Cohen S, et al. Directed elimination of senescent cells by inhibition of BCL-W and BCL-XL. Nat. Commun. 2016; 7:11190 Available from: http://www.nature.com/doifinder/10.1038/ncomms11190

Zhang X, Zhang S, Liu X, Wang Y, Chang J, Zhang X, et al. Oxidation resistance 1 is a novel senolytic target. Aging Cell. 2018; e12780 Available from: http://doi.wiley.com/10.1111/acel.12780

Zhu Y, Doornebal E J, Pirtskhalava T, Giorgadze N, Wentworth M, Fuhrmann-Stroissnigg H, et al. New agents that target senescent cells: the flavone, fisetin, and the BCL-XL inhibitors, A1331852 and A1155463. Aging (Albany. N.Y.). 2017; 9(3):955-63 Available from: http://www.aging-us.com/article/101202

Zhu Y, Tchkonia T, Fuhrmann-Stroissnigg H, Dai H M, Ling Y Y, Stout M B, et al. Identification of a novel senolytic agent, navitoclax, targeting the Bcl-2 family of anti-apoptotic factors. Aging Cell. 2016; 15(3):428-35

Zhu Y, Tchkonia T, Pirtskhalava T, Gower A C, Ding H, Giorgadze N, et al. The Achilles' heel of senescent cells: From transcriptome to senolytic drugs. Aging Cell. 2015; 14(4):644-58

The invention claimed is:

1. A method of selectively eliminating senescent skin fibroblasts, senescent lung fibroblasts, senescent umbilical vein endothelial cells, and senescent renal proximal tubule endothelial cells comprising administering a composition comprising an inhibitor of long-chain-fatty-acid-CoA ligase (ACSL) 4 to treat idiopathic pulmonary fibrosis, osteoarthritis, skin wounds, and skin aging in a patient, wherein the ACSL4 inhibitor is triacsin C, and wherein senescent cells are characterized by an increased intracellular level of lysophosphatidylcholine, arachidonic acid and/or phospholipase A2 activity compared to a non-senescent cell of the same type or age.

2. The method of claim 1, wherein the composition further comprises at least one inhibitor of cyclooxygenase-1 (COX-1), cyclooxygenase-2 (COX-2) or lipoxygenase selected from the group consisting of diclofenac, MK886, licofelone.

3. The method of claim 2, wherein the inhibitor of COX-1, COX-2, or lipoxygenase is diclofenac.

4. The method of claim 2, wherein the inhibitor of COX-1, COX-2, or lipoxygenase is MK886.

5. The method of claim 2, wherein the inhibitor of COX-1, COX-2, or lipoxygenase is licofelone.

6. The method of claim 1, wherein the composition further comprises a compound capable of inhibiting intracellular conversion of arachidonic acid, wherein said compound is cycloate.

7. The method of claim 1, wherein the composition further comprises a compound capable of manipulating intracellular ATP levels, wherein said compound is oligomycin.

8. The method of claim 1, wherein the patient has idiopathic pulmonary fibrosis.

9. The method of claim 1, wherein the patient has osteoarthritis.

10. The method of claim 1, wherein the patient has a skin wound.

11. The method of claim 1, wherein skin aging is treated.

* * * * *